US010993983B2

(12) United States Patent
Kritzer et al.

(10) Patent No.: US 10,993,983 B2
(45) Date of Patent: May 4, 2021

(54) CYCLIC PEPTIDE EPITOPES AND SMALL-MOLECULE MIMICS FOR INDUCING AUTOPHAGY

(71) Applicants: TRUSTEES OF TUFTS COLLEGE, Medford, MA (US); BOARD OF REGENTS OF THE UNIVERSITY OF TEXAS SYSTEM, Austin, TX (US)

(72) Inventors: Joshua Kritzer, Medford, MA (US); Beth Levine, Austin, TX (US); Leila Peraro, Medford, MA (US)

(73) Assignees: Trustees of Tufts College, Medford, MA (US); Board of Regents of the University of Texas System, Austin, TX (US)

( * ) Notice: Subject to any disclaimer, the term of this patent is extended or adjusted under 35 U.S.C. 154(b) by 53 days.

(21) Appl. No.: 16/085,913

(22) PCT Filed: Mar. 17, 2017

(86) PCT No.: PCT/US2017/022974
§ 371 (c)(1),
(2) Date: Sep. 17, 2018

(87) PCT Pub. No.: WO2017/161274
PCT Pub. Date: Sep. 21, 2017

(65) Prior Publication Data
US 2019/0382443 A1 Dec. 19, 2019

Related U.S. Application Data

(60) Provisional application No. 62/310,448, filed on Mar. 18, 2016, provisional application No. 62/424,934, filed on Nov. 21, 2016.

(51) Int. Cl.
*A61K 38/08* (2019.01)
*A61K 38/00* (2006.01)
*C07K 7/06* (2006.01)

(52) U.S. Cl.
CPC ................ *A61K 38/08* (2013.01); *C07K 7/06* (2013.01)

(58) Field of Classification Search
None
See application file for complete search history.

(56) References Cited

U.S. PATENT DOCUMENTS

2015/0133633 A1 5/2015 Rushala et al.
2015/0359840 A1 12/2015 Levine et al.

OTHER PUBLICATIONS

Chan, et al., "Modification of N-Terminal alpha-Amino Groups of Peptides and Proteins Using Ketenes," J. Am. Chem. Soc., vol. 134, pp. 2589-2598 (2012).
International Search Report and Written Opinion for Corresponding PCT/US2017/022974, dated Aug. 25, 2017 (9 pages).

*Primary Examiner* — Thomas S Heard
(74) *Attorney, Agent, or Firm* — Melissa Hunter-Ensor; Leslie A. Serunian; Greenberg Traurig, LLP

(57) ABSTRACT

Disclosed herein are cyclic peptides that induce cellular autophagy and have significant cell penetration activity. Methods for inducing autophagy and thereby treating various diseases and conditions associated with impaired autophagy are provided.

5 Claims, 30 Drawing Sheets
Specification includes a Sequence Listing.

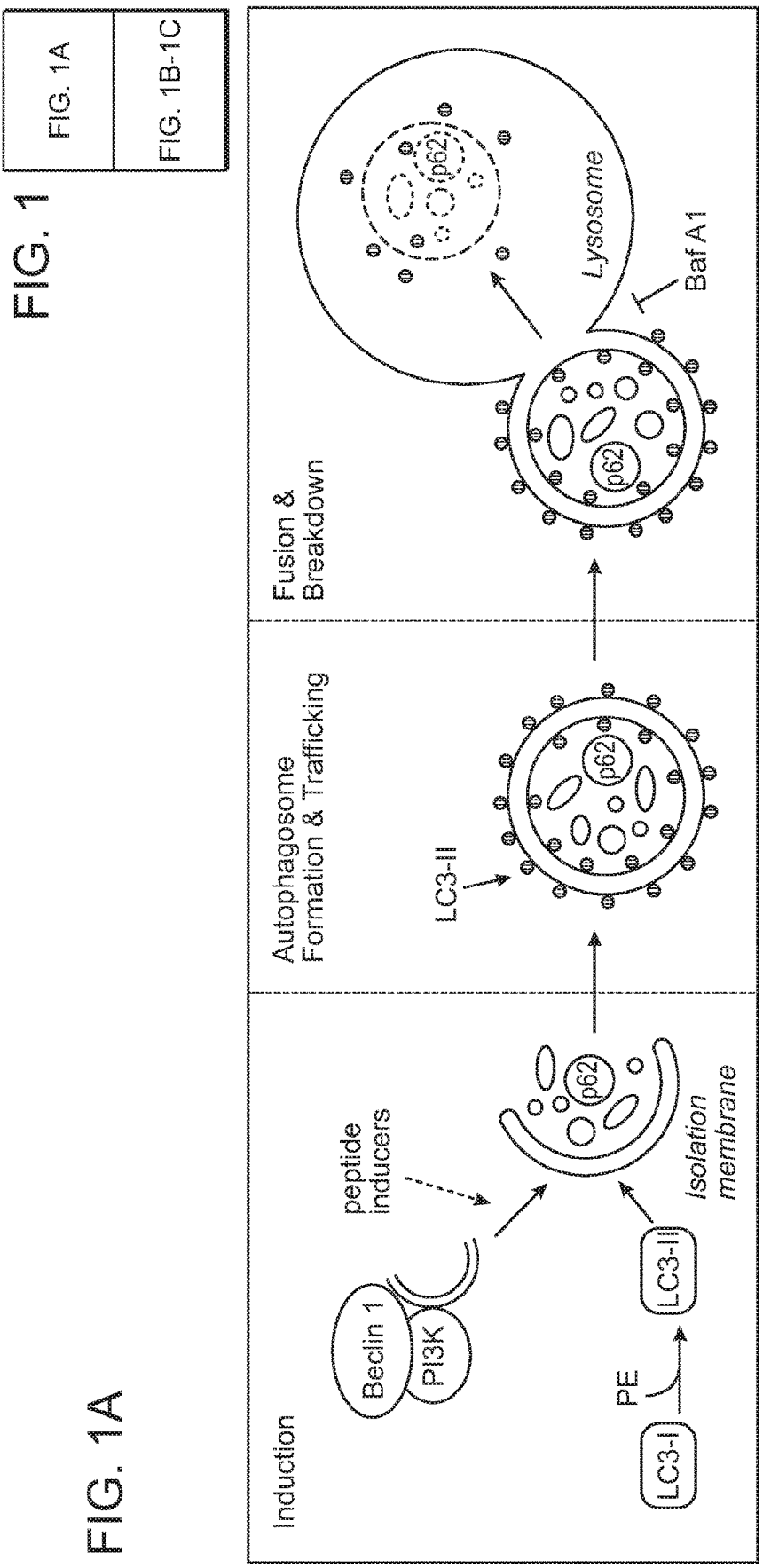

```
                    1          11
Tat-11mer   Tat-GG-VWNATFHIWHD
     N3A    Tat-GG-VWAATFHIWHD
     T5A    Tat-GG-VWNAAFHIWHD
     F6A    Tat-GG-VWNATAHIWHD
     H7A    Tat-GG-VWNATFAIWHD
     I8A    Tat-GG-VWNATFHAWHD
     W9A    Tat-GG-VWNATFHIAHD
    H10A    Tat-GG-VWNATFHIWAD
     W2A    Tat-GG-VANATFHIWHD
```

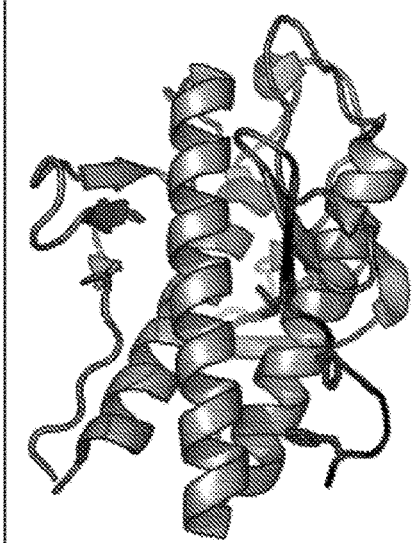

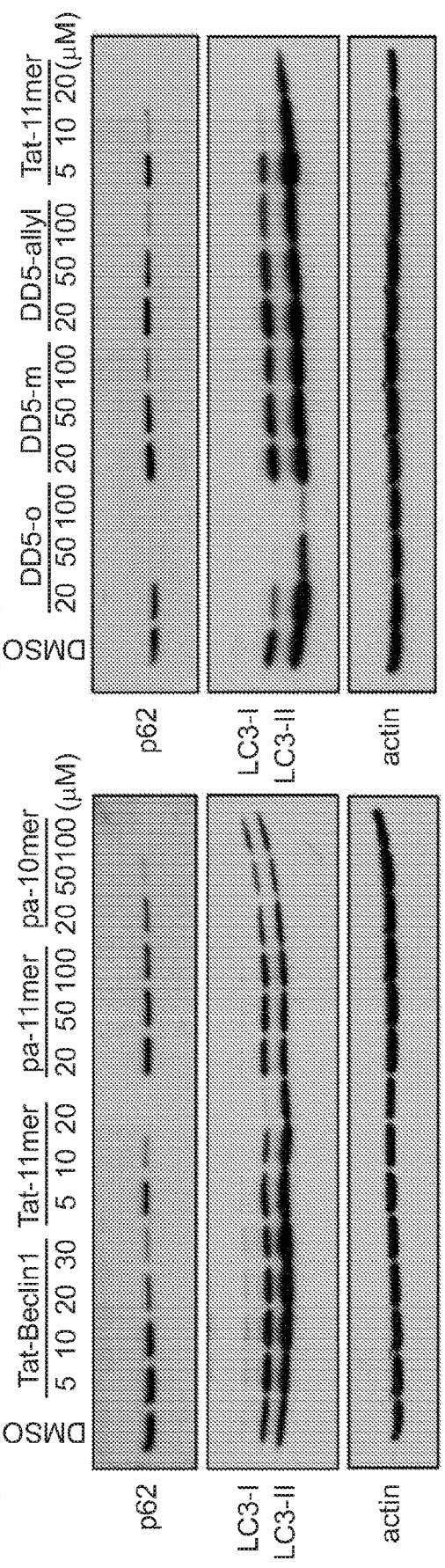
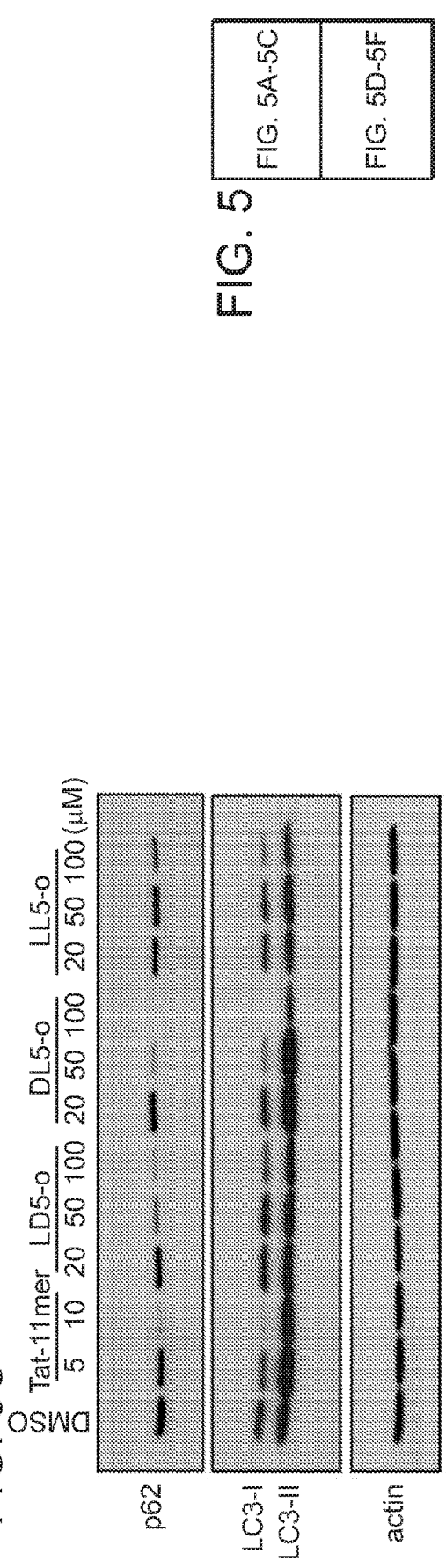
FIG. 5A
FIG. 5B
FIG. 5C
FIG. 5

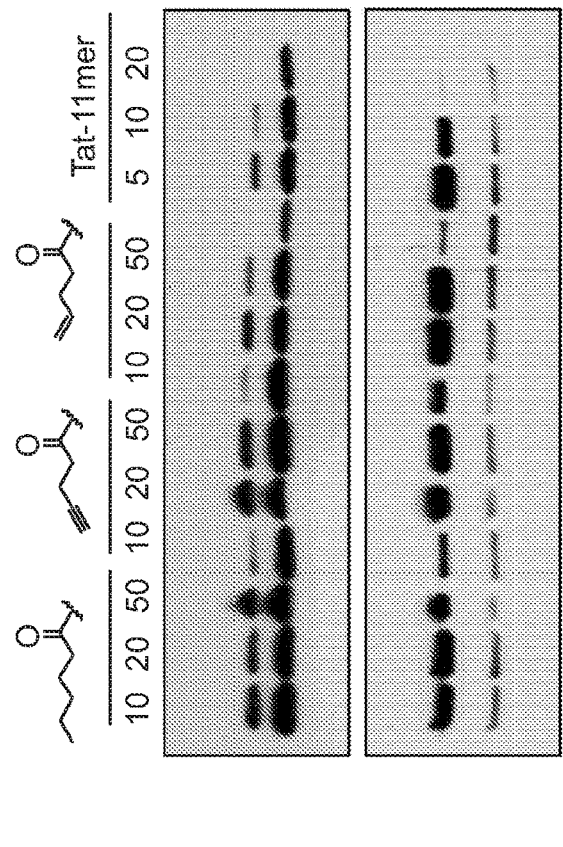
FIG. 8
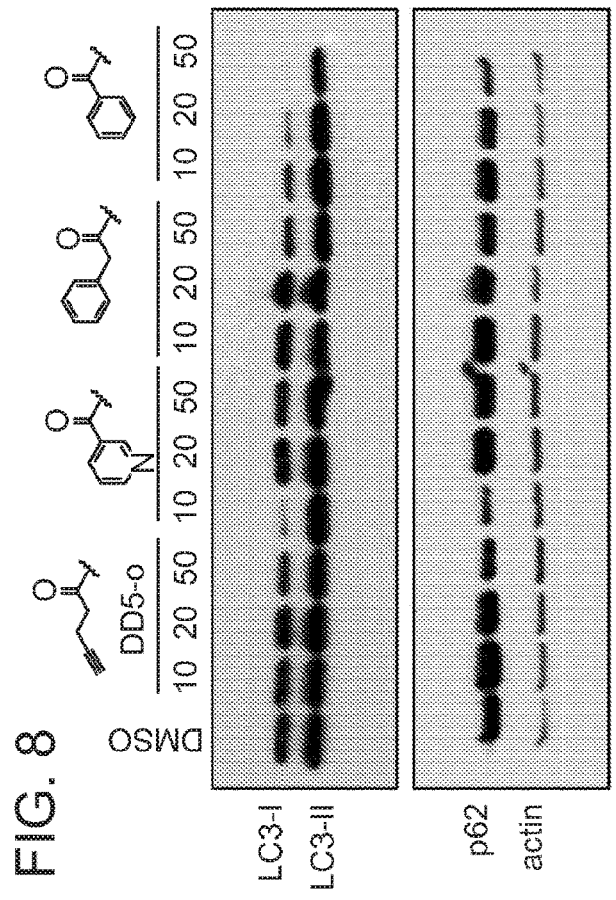
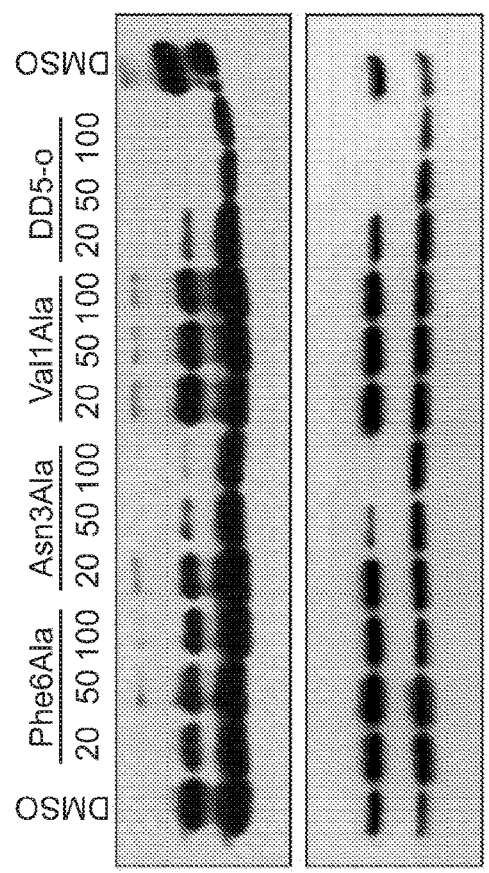
FIG. 9

FIG. 10C
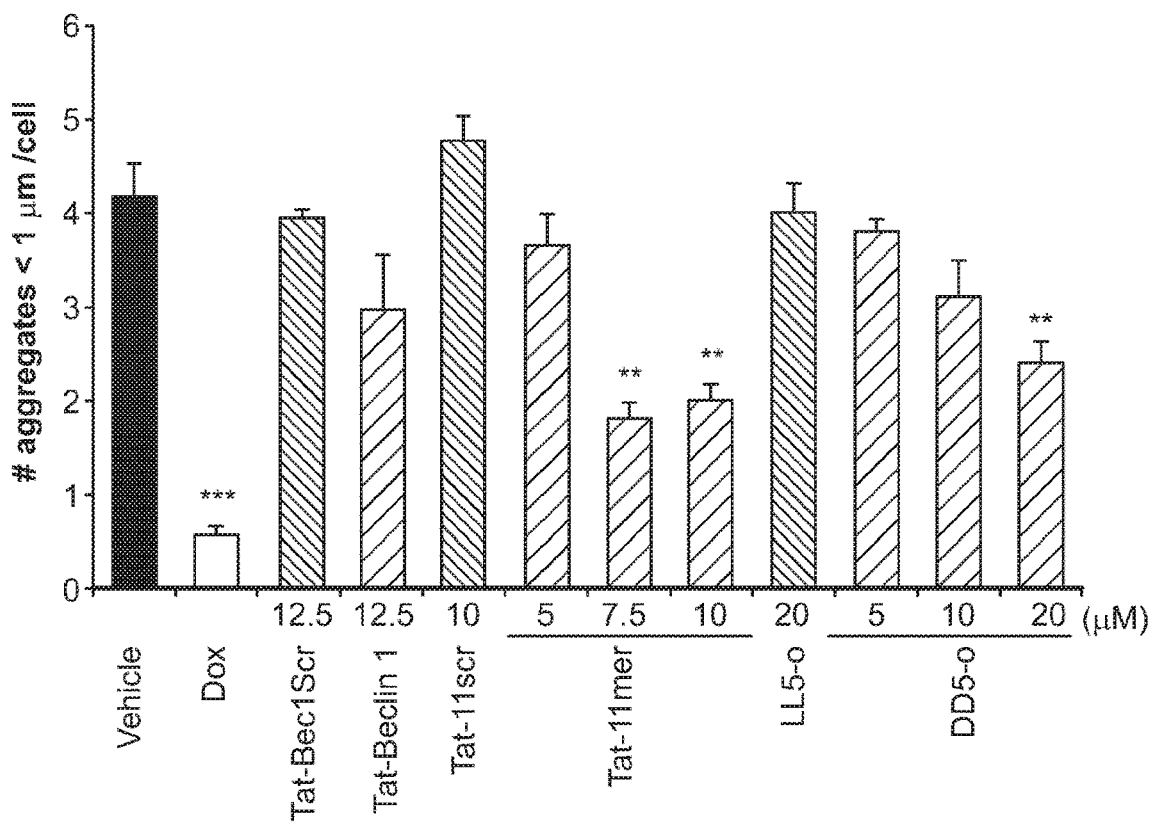
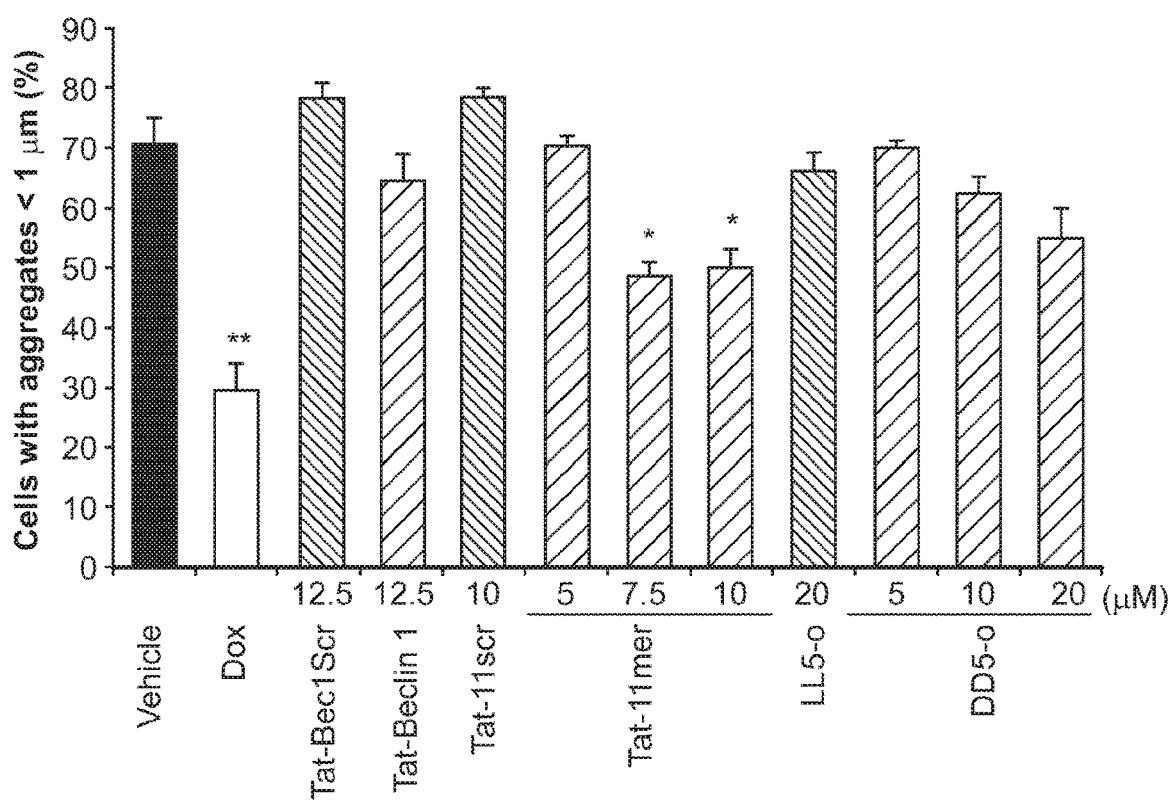

Front view          Back view

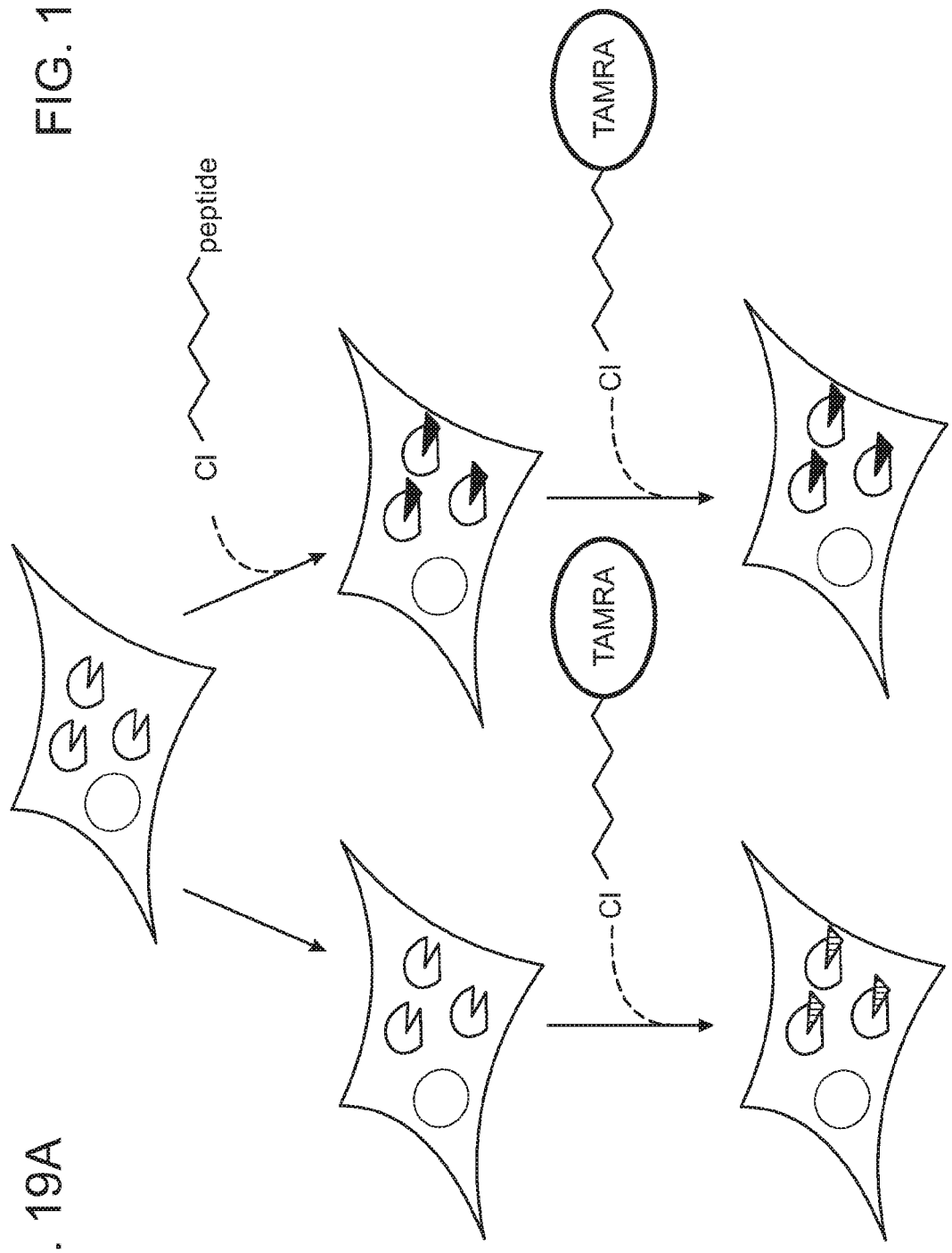

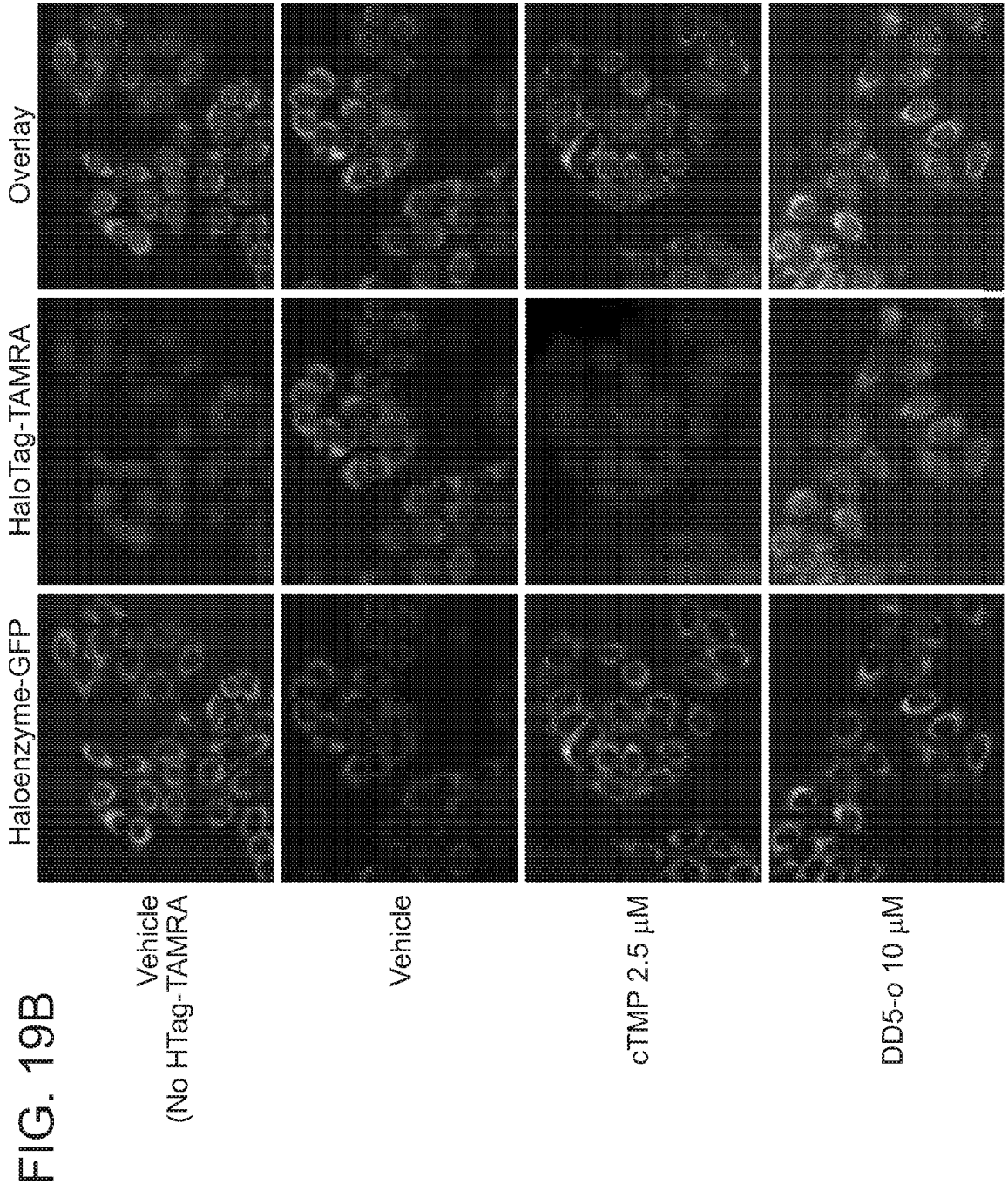

CYCLIC PEPTIDE EPITOPES AND SMALL-MOLECULE MIMICS FOR INDUCING AUTOPHAGY

CROSS-REFERENCE TO RELATED APPLICATIONS

This application is the U.S. national phase application, pursuant to 35 U.S.C. § 371, of PCT International Application Serial No.: PCT/US2017/022974, filed Mar. 17, 2017, designating the United States and published in English, which claims priority to and the benefit of the following U.S. Provisional Application No. 62/310,448, filed Mar. 18, 2016 and 62/424,934, filed Nov. 21, 2016, the disclosure of which applications are incorporated herein by reference in their entirety.

GOVERNMENT LICENSE RIGHTS

This invention was made with government support under contract number U19AI109725 awarded by the National Institutes of Health. The government has certain rights in the invention.

SEQUENCE LISTING

The instant application contains a Sequence Listing which has been submitted electronically in ASCII format and is hereby incorporated by reference in its entirety. The ASCII copy, created on Feb. 11, 2019, is named 167774_010404_US_SL.txt and is 30,864 bytes in size.

BACKGROUND

In the last two decades, early-stage drug discovery has expanded to include targets outside the traditionally druggable classes of enzymes and cell surface receptors. Classically "undruggable" protein-protein interactions can make viable drug targets, but often have large interaction surfaces that are difficult for small molecules to bind with high affinity. Peptides are an attractive option for targeting protein-protein interactions, as they are intermediate in size between small molecules and large biologics and offer many advantages over both. Peptides are synthetically tractable, they can be optimized to high affinity and selectivity, and they often have good safety and tolerability profiles in animals and humans. However, short peptides are often poorly structured in aqueous solution, which can limit their affinity for their targets. One of the largest limitations of peptide drugs is poor membrane penetration, making delivery to intracellular targets difficult. Therefore, a need exists for peptides having effective cell penetration.

Macroautophagy (hereafter referred to as autophagy) is a coordinated process by which eukaryotic cells recycle material, including bulk cytosol, damaged organelles, protein aggregates, and invading organisms. It is an evolutionarily conserved pathway in all eukaryotes and is fundamental for cellular survival and development. Autophagy is initiated in the cytosol, where cellular or foreign material becomes engulfed by a double-membrane vesicle called the autophagosome (FIG. 1, panel a). Autophagosomes are then trafficked to the lysosome, where they fuse with the lysosomal membrane and release their contents for enzymatic breakdown. Autophagy is a basic function of all eukaryotic cells, and thus plays important roles in all areas of human health and disease.

The molecular pathways that control autophagy are an intense area of current study. Some of the upstream signaling events that trigger autophagy, such as mTOR inhibition and Akt activation, have been elucidated. However, the molecular mechanisms of cargo recognition, autophagosome initiation, remodeling of the double membrane, autophagosome trafficking, and lysosomal fusion are just starting to be revealed. The protein Beclin 1 is a master regulator of autophagy. When autophagy is triggered, Beclin 1 forms a large multiprotein complex with a class III phosphatidylinositol 3-kinase, and this complex nucleates autophagosomes. Beclin 1 interacts with several known positive and negative regulators of autophagy, including Bcl-2/Bcl-$x_L$, AMBRA1, Rubicon, DAPK, AKT, EGFR, MAPAPK2/3, Golgi-Associated Plant Pathogenesis-Related protein 1 (GAPR-1), and HIV-Nef, highlighting its critical role in the control of autophagy initiation.

Impaired autophagy is a hallmark of diverse human diseases. Protein aggregation, a common feature of many neurodegenerative disorders including Alzheimer's, Parkinson's, and Huntington's, has been linked to reduced initiation of autophagy and impaired fusion of autophagosomes to lysosomes. Down-regulation of autophagy, including decreased expression of Beclin 1, has also been implicated in tumorigenesis. Mutations or polymorphisms in several different autophagy genes have also been linked to familial neurodegenerative disorders, muscular diseases, inflammatory bowel disease and other autoimmune and/or inflammatory disorders, and enhanced susceptibility to certain infectious diseases. Loss-of-function studies in mice and other model organisms demonstrate a crucial role for the autophagy pathway in protein and organelle quality control, metabolism, innate and adaptive immunity, protection against aging and a wide range of diseases. Since impaired autophagy is prominent in the pathogenesis and pathology of so many conditions, pharmacological activation of autophagy has been proposed as a promising avenue for new treatments. As proof-of-principle for this concept, tissue-specific autophagy gene delivery in liver, muscle, brain or lung improves hepatic insulin resistance/diabetes, lysosomal storage disorders, muscular dystrophy, neurodegenerative diseases, and cystic fibrosis in mouse models. However, such gene therapy approaches are not readily translatable to patients. While many existing FDA-approved drugs enhance autophagy, they have pleiotropic effects and it is not known whether their clinical benefits are mediated by autophagy. Thus, potent and selective molecules are highly sought after to test autophagy activation as a therapeutic mode for these and other conditions.

To date, one of the most potent, selective inducers of autophagy is the peptide Tat-Beclin 1, which was derived from the sequence of Beclin 1 (FIG. 1, b,c). Tat-Beclin 1 activates Beclin 1 and the core autophagy initiation complex, in a manner that antagonizes the effects of the negative regulator GAPR-1. Tat-Beclin 1 significantly increases autophagic flux at 10 μM in cell culture, and also induces autophagy when administered to mice at 20 mg/kg. It has also been shown to be effective in several in vitro and in vivo models of human disease. In cultured cells, Tat-Beclin 1 inhibits the replication of several intracellular pathogens (including West Nile virus, chikungunya virus, *Listeria monocytogenes*, and *Mycobacterium tuberculosis*), reduces lung fibroblast expression of fibrotic markers, increases human renal cell ciliogenesis, and increases pancreatic β-cell secretion of insulin. In mice, intraperitoneal delivery of Tat-Beclin I inhibits viral replication and reduces mortality during West Nile virus and chikungunya virus infection, improves pressure overload-induced heart failure, enhances immune-dependent chemotherapy responses, and restores bone growth in the setting of FGF signaling mutations. Transcatheter intravesicular delivery of Tat-Beclin 1 markedly reduces bacterial burden in *E. coli*-infected bladders. Thus, in diverse tissues and model systems, Tat-Beclin 1 has become a powerful tool to explore the mechanism of autophagy initiation and the effect of autophagy on disease. However, it has inherent liabilities for drug development, including its large size, its composition as a peptide with all natural amino acids, and its inability to enter cells without the polycationic Tat sequence. Like many Tat-linked peptides, Tat-Beclin 1 is cytotoxic at high concentrations or following prolonged treatment. While Tat-linked peptides have been explored as potential therapeutics, decades of study have raised concerns with their overall distribution properties, efficacy and safety. Thus, despite the broad adoption of Tat-Beclin 1 as a tool compound, the development of Tat-independent autophagy inducers represents a fundamental milestone for the translation of recent discoveries in the field of autophagy into potential human therapeutics.

Thus, a need exists for the development of new autophagy inducing compounds and compositions.

SUMMARY

Provided herein are cyclic peptides and small-molecule mimics that are cell penetrating, and methods of using the same to induce cellular autophagy in vitro and in vivo. In some embodiments, the cyclic peptide is a compound selected from Formulae I, II, IIIa, IIIb, and IIIc:

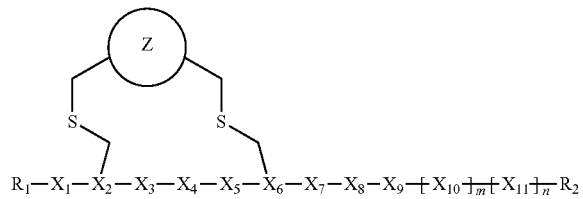

Formula I

Formula II

Formula IIIa $R_1-X_1-X_2-X_3-X_4-X_5-X_6-X_7-X_8-X_9-(X_{10})_m-(X_{11})_n-R_2$, Formula IIIb $R_1-X_1-X_2-X_3-X_4-X_5-X_6-X_7-X_8-X_9-(X_{10})_m-(X_{11})_n-R_2$, and Formula IIIc $R_1-X_1-X_2-X_3-X_4-X_5-X_6-X_7-X_8-X_9-(X_{10})_m-(X_{11})_n-R_2$, wherein:

$R_1$ is selected from

A)

B)

C)

D)

E)

F)

G)
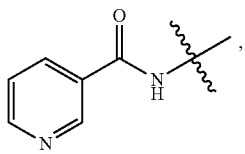
H) H₂N—,
I) MeC(O)—, and
J) c(FΦRRRRE) (SEQ ID NO: 14);
$R_2$ is —C(O)$_2$NH$_2$,
Z is selected from:
A)
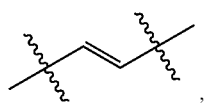
OP)
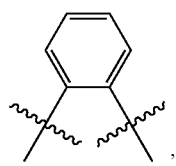
MP)
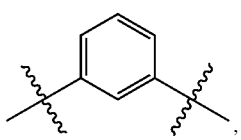
PP)
PY)
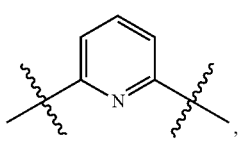
ON)
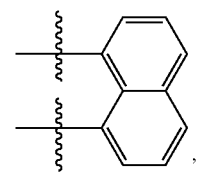
MN)
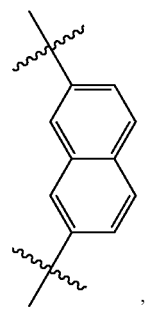
PN)
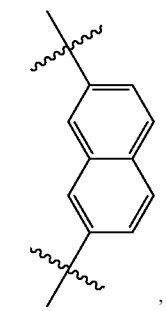
OPB)
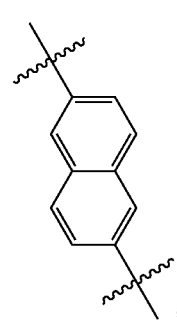
MPB)
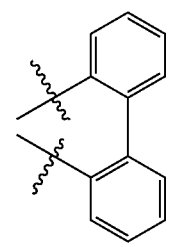
PBP)
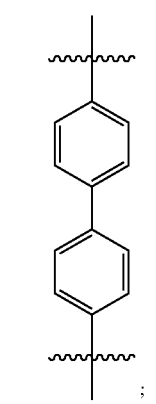
, and
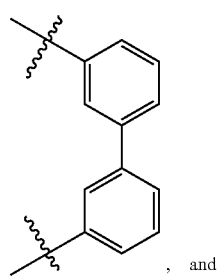

$X_1$ is selected from C, D, G, T, V and W,
$X_2$ is selected from C, $\underline{C}$, F, H, L, N, W, and Y,
$X_3$ is selected from A, D, N, and W,
$X_4$ is selected from A, I, S and T,
$X_5$ is selected from A, C, $\underline{C}$, F, H, and T,
$X_6$ is selected from C, $\underline{C}$, F, H, and W,
$X_7$ is selected from A, D, E, H, I, and T,
$X_8$ is selected from A, F, I, L, M, R, V, W, and Y,
$X_9$ is selected from A, F, H, N, and W,
$X_{10}$ is selected from A, C, $\underline{C}$, D, H, R, W, and Y, and
$X_{11}$ is selected from D, E, and V;
$X_1$-$X_{11}$ are all in the L configuration, except for $\underline{C}$ which is in the D configuration;
m is 0 or 1, and
n is 0 or 1,
or a pharmaceutically acceptable salt thereof.

In some embodiments, $R_1$ is

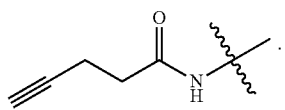 [SMILES: *NC(=O)CCC#C]

In other embodiments, $R_1$ is

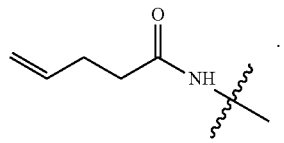 [SMILES: *NC(=O)CCC=C]

In some embodiments, $R_1$ is $H_2N$—.
In some embodiments, Z is

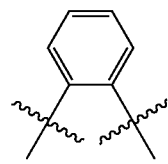

In some embodiments, Z is

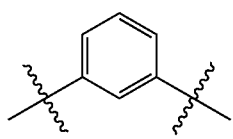

In some embodiments, Z is

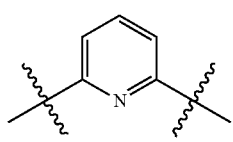

In other embodiments, Z is

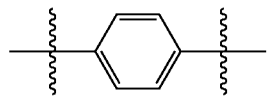

In some embodiments, $X_2$ is $\underline{C}$ and $X_6$ is $\underline{C}$. In some embodiments, $X_2$ is C and $X_6$ is $\underline{C}$. In other embodiments, $X_2$ is $\underline{C}$ and $X_5$ is $\underline{C}$. In some embodiments, $X_1$-$X_{10}$ is V$\underline{C}$NAT$\underline{C}$HIWH (SEQ ID NO: 1), and m is 1. In some embodiments, $X_1$-$X_{10}$ is V$\underline{C}$NATCHIWH (SEQ ID NO: 2), and m is 1. In some embodiments, $X_1$-$X_{10}$ is VCNAT$\underline{C}$HIWH (SEQ ID NO: 9), and m is 1. In some embodiments, $X_1$-$X_{10}$ is V$\underline{C}$NAT$\underline{C}$HIWR (SEQ ID NO: 3), and m is 1. In some embodiments, $X_1$-$X_{10}$ is VWNAT$\underline{C}$HIW$\underline{C}$ (SEQ ID NO: 4), and m is 1. In some embodiments, $X_1$-$X_{10}$ is VWNATFHIWHD (SEQ ID NO: 5), m is 1 and n is 1. In some embodiments, $X_1$-$X_{10}$ is VWNAT$\underline{C}$HIWC (SEQ ID NO: 11), and m is 1.

In some embodiments, the compound is Formula I. In some embodiments, $R_1$ is A and Z is selected from MP and OP. In some embodiments, $R_1$ is $H_2N$ and Z is selected from MP. In other embodiments, $R_1$ is MeC(O) and Z is selected from MP. In still other embodiments, $R_1$ is c(FΦRRRRE) (SEQ ID NO: 14) and Z is selected from MP.

In some embodiments, the compound is Formula II. In some embodiments, $R_1$ is A and Z is selected from PP, MP and OP. In some embodiments, Z is OP.

In other embodiments, the compound is Formula Ma. In some embodiments, $R_1$ is A. In some embodiments, $R_1$ is $H_2N$. In other embodiments, $R_1$ is c(FΦRRRRE) (SEQ ID NO: 14). In some embodiments, the compound is Formula IIIb. In some embodiments, $R_1$ is A. In some embodiments, the compound is Formula IIIc. In some embodiments, $R_1$ is C.

Disclosed herein are compounds, and pharmaceutically acceptable salts thereof, that include those of Formula I, II, Ma, and Mb such as:

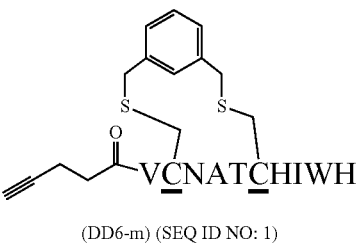

(DD6-m) (SEQ ID NO: 1)

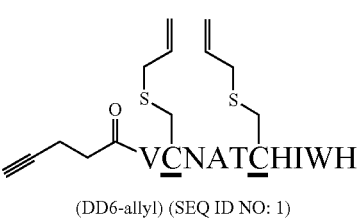

(DD6-allyl) (SEQ ID NO: 1)

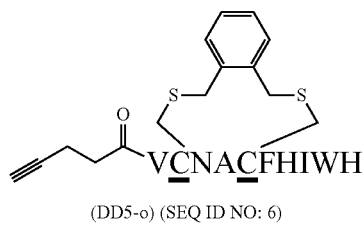

(DD5-o) (SEQ ID NO: 6)

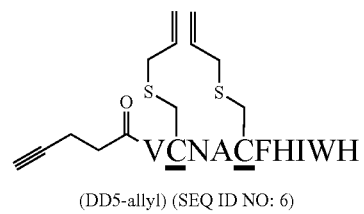

(DD5-allyl) (SEQ ID NO: 6)

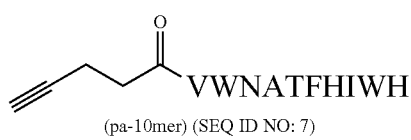

(pa-10mer) (SEQ ID NO: 7)

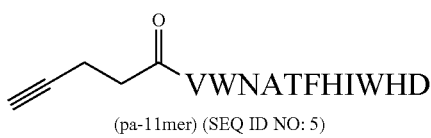

(pa-11mer) (SEQ ID NO: 5)

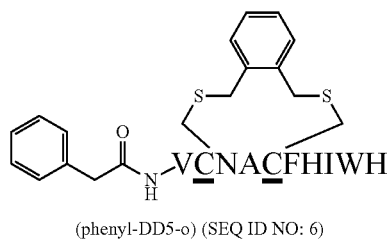

(phenyl-DD5-o) (SEQ ID NO: 6)

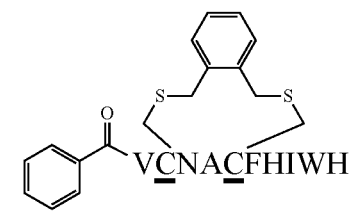

(benzo-DD5-o) (SEQ ID NO: 6)

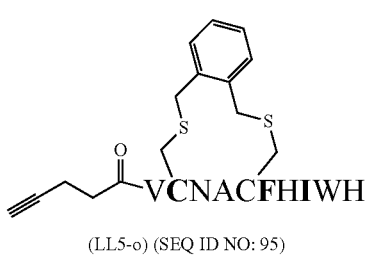

(LL5-o) (SEQ ID NO: 95)

In a further aspect, provided herein is a modified peptide, or pharmaceutically acceptable salt thereof, comprising a linker of formula VI covalently bonded at two amino acids (e.g., at the alpha-carbon), Xa and Xb of formula VII:

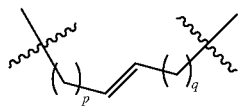

Formula VI

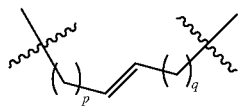

Formula VII $R_1-X_1-X_2-X_3-X_4-X_5-X_6-X_7-X_8-X_9+X_{10}\overline{)_m}+X_{11}\overline{)_n}R_2$ wherein:
a is an integer selected from 1-7, inclusive;
b is an integer selected from 4-10, inclusive;
Xa and Xb are 3, 4, or 7 amino acid residues apart;
the alpha-carbon on Xa and/or Xb optionally contains a methyl group substitution;
p and q are each independently an integer selected from 2, 3, and 4;
$R_1$ is selected from

A)

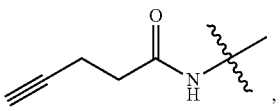

B)

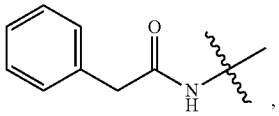

C)

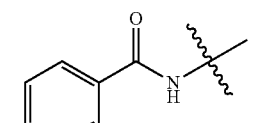

D)

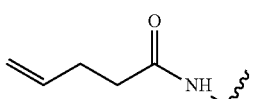

E)

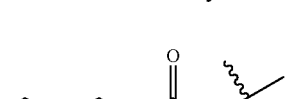

F)

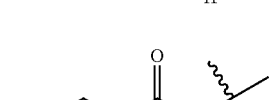

G)

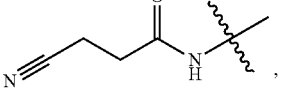

H) H$_2$N—,
I) MeC(O)—, and
J) c(FΦRRRRE) (SEQ ID NO: 14);
R$_2$ is —C(O)$_2$NH$_2$;
X$_1$ is selected from C, D, G, T, V, and W,
X$_2$ is selected from C, C̲, F, H, L, N, W, and Y,
X$_3$ is selected from A, D, N, and W,
X$_4$ is selected from A, I, S, and T,
X$_5$ is selected from A, C, C̲, F, H, and T,
X$_6$ is selected from C, C̲, F, H, and W,
X$_7$ is selected from A, D, E, H, I, and T,
X$_8$ is selected from A, F, I, L, M, R, V, W, and Y,
X$_9$ is selected from A, F, H, N, and W,
X$_{10}$ is selected from A, C, C̲, D, H, R, W, and Y, and
X$_{11}$ is selected from D, E, and V;
X$_1$-X$_{11}$ are all in the L configuration, except for C̲ which is in the D configuration;
m is 0 or 1; and
n is 0 or 1.

In another aspect, provided herein are methods of inducing autophagy in a cell, the method comprising contacting the cell with an effective amount of a peptide as disclosed herein. Also provided herein are methods of treating a disease or condition having impaired autophagy, including but not limited to neurodegenerative disorders, cancers, muscular diseases, inflammatory bowel disease, autoimmune and/or inflammatory disorders, infectious diseases (e.g., infection with intracellular pathogens such as virus or bacteria), metabolic disorders, innate and adaptive immune disorders, aging, hepatic insulin resistance/diabetes, lysosomal storage disorders, muscular dystrophy, and cystic fibrosis. The methods can include administering to a subject in need thereof an effective amount of a peptide as disclosed herein. In some embodiments, the subject is a mammal, such as a human, feline, canine, bovine, avian, or rodent.

Pharmaceutical compositions are also provided herein, comprising any peptide disclosed herein, as well as kits that comprise such peptide.

In addition to modified peptides, small-molecule helix mimics are also provided, such as those disclosed in Okuyama et al., *Nature Methods* 4, 153-159 (2007); Whitby and Boger, *Acc Chem Res* 2012, 45, 1698; Arkin et al., *Chemistry & Biology* 2014, 21(9): 1102-1114; Lanning and Fletcher, *Biology* 2015, 4, 540-555; Hoggard et al., *J. Am. Chem. Soc.*, 2015, 137 (38), pp 12249-12260; Wang et al., *RSC Adv.*, 2016, 6, 61599; and Groβ et al., *Front. Bioeng. Biotechnol.*, 2016, dx.doi.org/10.3389/fbioe.2015.00211; all of which are incorporated herein by reference in their entirety.

BRIEF DESCRIPTION OF THE DRAWINGS

FIGS. 1A-1C illustrate the autophagic pathway and peptide inducers of autophagy. 1A. Overall schematic of the process of autophagy. In response to upstream signaling, Beclin 1 and its PI3K complex nucleate membrane formation. The microtubule-associated protein light chain I (LC3-I) becomes lipidated with phosphatidylethanolamine (PE). The lipidated form, LC3-II, is then incorporated in autophagosome membranes. The autophagosome matures and fully engulfs the cargo, and is trafficked to the lysosome. It then fuses with the lysosome, leading to the breakdown and recycling of the cargo, including the autophagy adaptor protein, p62. Peptide inducers appear to act during the induction phase (red dashed arrow). Bafilomycin A1 (Baf A1) is a known inhibitor of the lysosomal fusion step. 1B. Crystal structure of the ECD of human Beclin 1. The segment shown in black corresponds to the sequence of the Beclin 1-derived portion of Tat-11mer, and the red residues correspond to the required hot spots for Tat-11mer activity. 1C. Sequences of peptides, their names, and the lowest concentrations (µM) at which pro-autophagic activity was observed, as defined by an increase in both p62 degradation and LC3 lipidation (SEQ ID NOs: 8, 63, 1, 6, and 95). The conserved hot spot residues are underlined. The cysteine residues and linkers are highlighted in blue.

FIG. 3 depicts an N-terminal Tat-linked peptide and the results of substitution of other amino acids at each position (see SEQ ID NO: 105). The top substitutions are given along with activity data (p62 degradation and LC3 marker assays) as to whether they were more, less, or about equal potency to Tat-beclin-1. The bottom substitutions indicate where alanine (A) was substituted for the given amino acid to determine the relative contribution that amino acid had to the overall peptide potency. For example, substituting T for A (and no other substitutions) resulted in a peptide that had greater activity that wild-type. (Sequences are SEQ ID NOs: 20, 104-105 and 63, in order of appearance).

FIGS. 5A-5F. Peptides induce autophagy in HeLa cells and increase autophagic flux. Autophagy induction in HeLa cells was measured by treating cells with the indicated concentration of each peptide, and then analyzing p62 degradation and LC3 lipidation by immunoblot. Actin is shown as a loading control (a-e). 5A. Optimized Tat-11mer induces autophagy, at 5 µM, about 2-fold better than Tat-beclin 1 (10 µM). Removing Tat and capping the N-terminus (pa-11mer; sequence in Table 1) leads to loss of activity, but truncation of the C-terminal Asp (pa-10mer) regains some activity at 100 µM. 5B. Autophagy induction is dependent on linker conformation. DD5-o induced autophagy at 20 µM, while DD5-m, which has a meta-xylene instead of ortho-xylene, and DD5-allyl, which is not stapled and instead has an allyl group on each D-cysteine, did not induce autophagy. 5C. Autophagy induction depends on the stereochemistry of the linker cysteines. DD5-o was the most active stereoisomer, while the stereoisomer with two L-cysteines, LL5-o had no autophagy-inducing activity. 5D. The N-terminal cap affects activity. DD5-o has a 4-pentynyl cap. When this cap is changed to an acetyl cap or a free amine, almost no autophagy-inducing activity is observed. 5E. Many variants of DD5-o, with a variety of N-terminal caps, were evaluated (see FIG. 8 for additional cap variants). 5F.

GFP-LC3 puncta assay in HeLa cells provides an independent measure of autophagic flux. GFP-LC3 HeLa cells were treated with and without bafilomycin A1 (Baf A1), which leads to accumulation of autophagosomes. For a-f, similar results were obtained in at least 3 independent experiments. Bars represent mean+/−s.e.m for triplicate samples (at least 100 cells analyzed per sample).  denotes P<0.001 and * denotes P<0.001 by t-test for indicated group vs. DMSO control.

Figure 6:
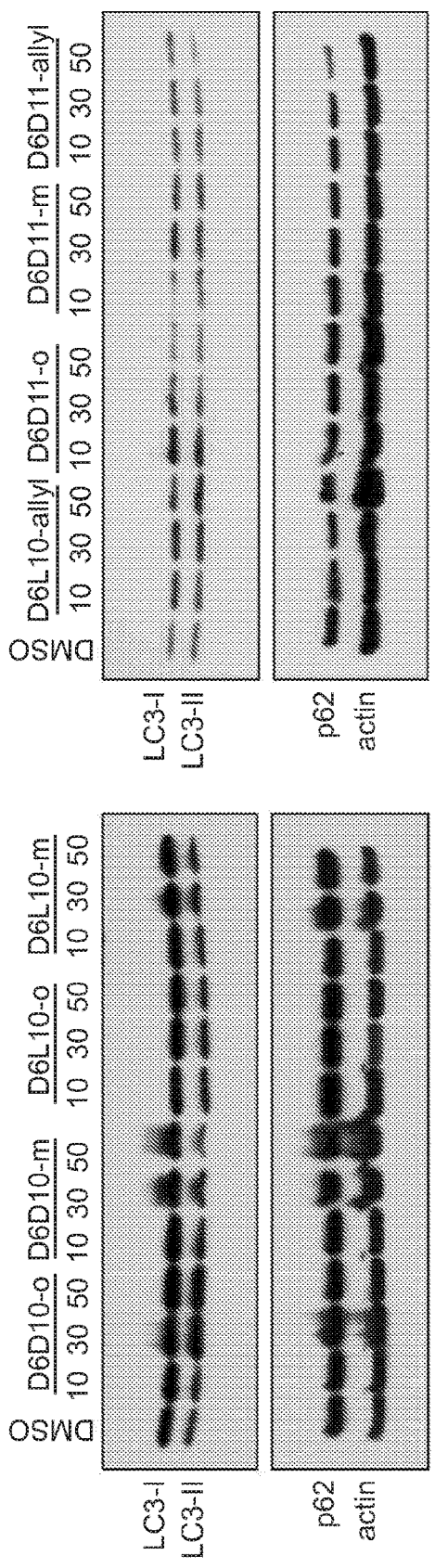

FIG. 6. Location of staple within peptide sequence affects activity. Autophagy induction in HeLa cells for additional peptides, analyzed using p62 and LC3 immunoblots. Actin is shown as a loading control. Autophagy induction is dependent on the location of the staple, which was moved to the C-terminal end of the Beclin 1-derived sequence. The stereochemistry of the cysteines was varied and three different linkers were used (ortho-xylene, meta-xylene and allyl), but for all peptides no autophagy induction was observed. Concentrations are noted in micromolar. Peptide sequences are given in Table 1.

Figure 7:
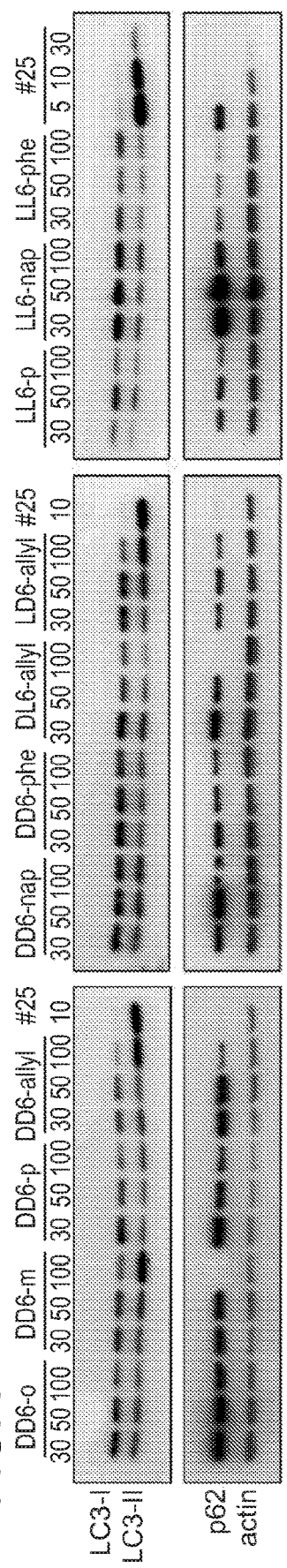

FIG. 7. Linker structure affects autophagy-inducing activity for DD6-series peptides. Autophagy induction in HeLa cells for additional peptides, analyzed using p62 and LC3 immunoblots. Actin is shown as a loading control. A variety of DD6-m analogs were tested, varying the size and type of linker as well as the stereochemistry of the cysteines. DD6-m and DL6-allyl induced autophagy at 100 µM. Concentrations are noted in micromolar. Peptide sequences are given in Table 1. Peptide #25: YGRKKRRQRRR-GG-VFNATFEIWH (SEQ ID NO: 10).

FIG. 8. N-terminal cap of DD5-o affects autophagy induction. Autophagy induction in HeLa cells for additional peptides, analyzed using p62 and LC3 immunoblots. Actin is shown as a loading control. Activity was observed for analogs of DD5-o with a benzoic acid cap, a hexanoic acid cap and a pentenoic acid cap at 50 µM. In contrast, no activity was observed for the nicotinic acid cap. Concentrations are noted in micromolar. Peptide sequences are given in Table 1.

FIG. 9. Alanine scan for DD5-o. Autophagy induction in HeLa cells for additional peptides, analyzed using p62 and LC3 immunoblots. Actin is shown as a loading control. Analogs of DD5-o with alanine substitutions in each position (except D-Cys2, Ala4, and D-Cys5) were synthesized and tested. Substitution of Ile8, Phe6, or Val1 leads to complete loss in activity. Trp9Ala has only mild activity at 100 µM. His10Ala is 5-fold worse in activity than DD5-o, with induction at 100 µM. Concentrations are noted in micromolar. Peptide sequences are given in Table 1.

Figure 10A:
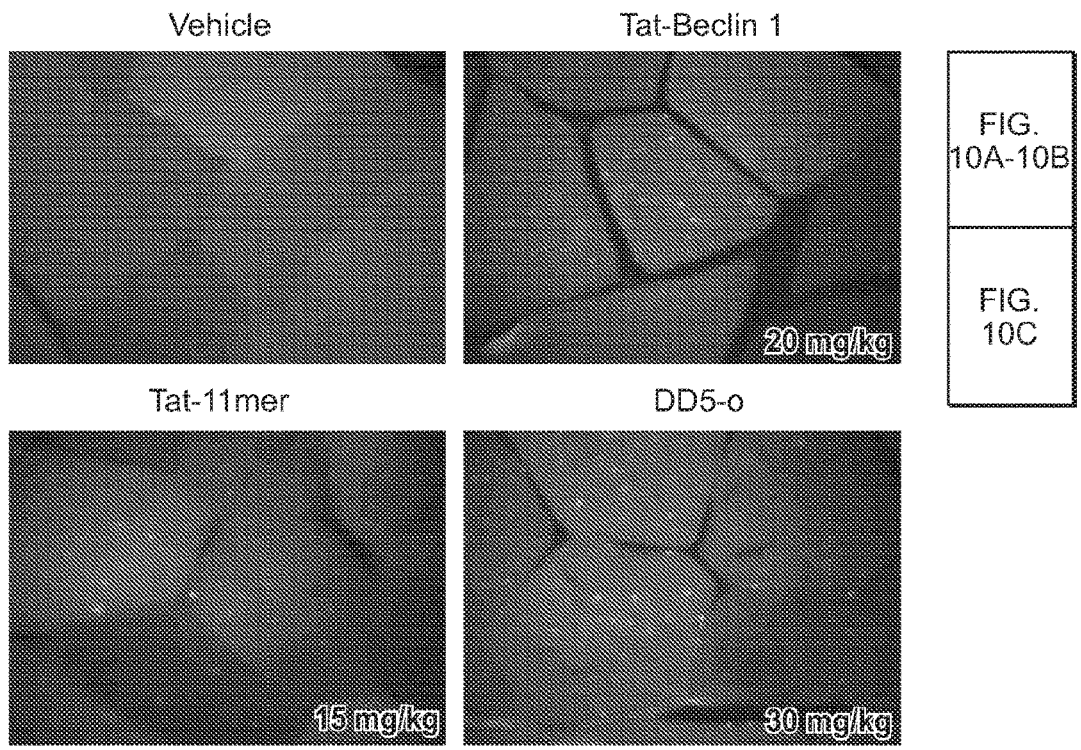
Figure 10B:
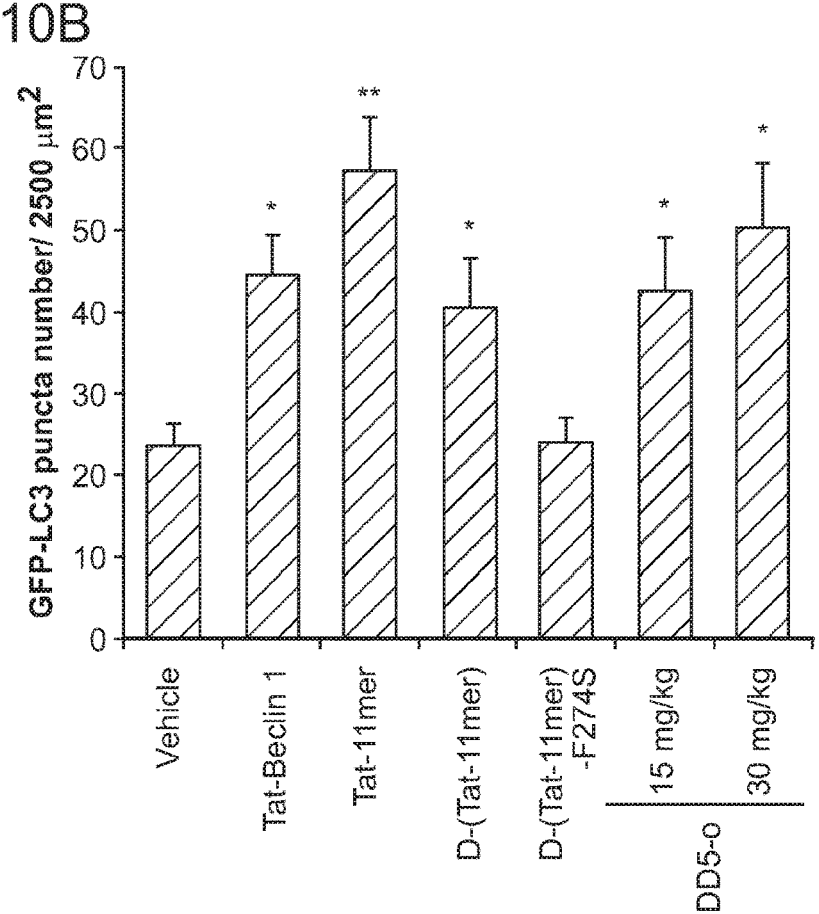

FIGS. 10A-10C. Autophagy induction observed in vivo and in Huntington's disease model. 10A. Representative images of muscle tissue sections from GFP-LC3 mice treated with vehicle or peptide at the concentration indicated. Concentrations are roughly equimolar, and tissue was analyzed 6 hours following intraperitoneal injection of peptide. 10B. GFP-LC3 puncta counted per 2500 µm$^2$ of muscle tissue. A minimum of ten fields were counted per tissue section. Bars represent mean+s.e.m. for four mice. 10C. Number of small htt103Q aggregates <1 µm per cell (top) and percentage of cells with aggregates (bottom) in HeLa cells expressing doxycycline (Dox)-repressible CFP-htt103Q. Bars represent mean±s.e.m. for triplicate samples (100-150 cells analyzed per sample). Similar results were obtained in three independent experiments. * denotes P<0.05 and ** denotes P<0.01 by t-test for indicated group versus vehicle control.

Figure 11:
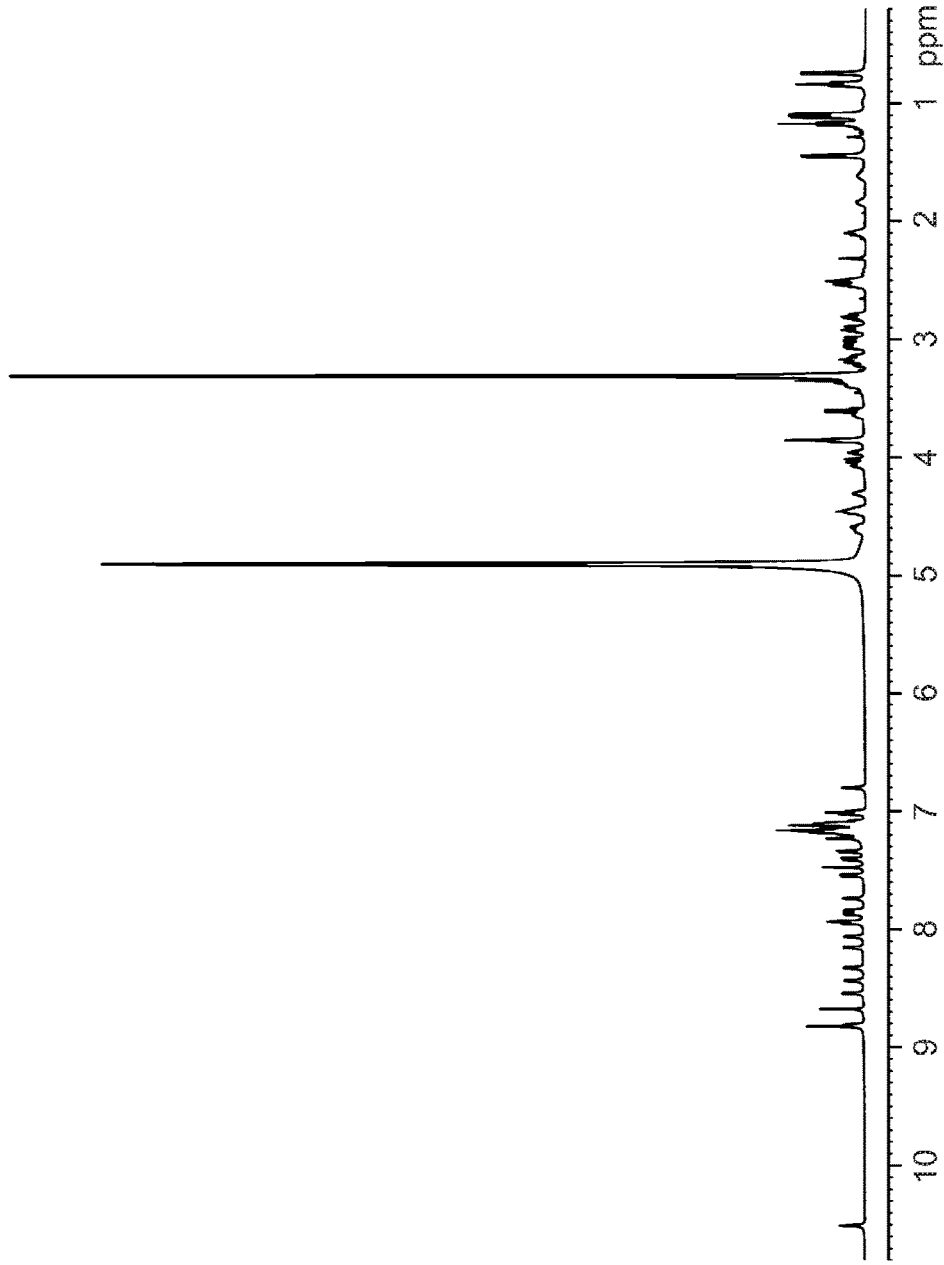

FIG. 11. $^1$H 1D NMR spectrum of DD5-o in CD$_3$OH at 289 K. The well-resolved, sharp peaks are indicative of a high degree of overall structure.

Figure 12:
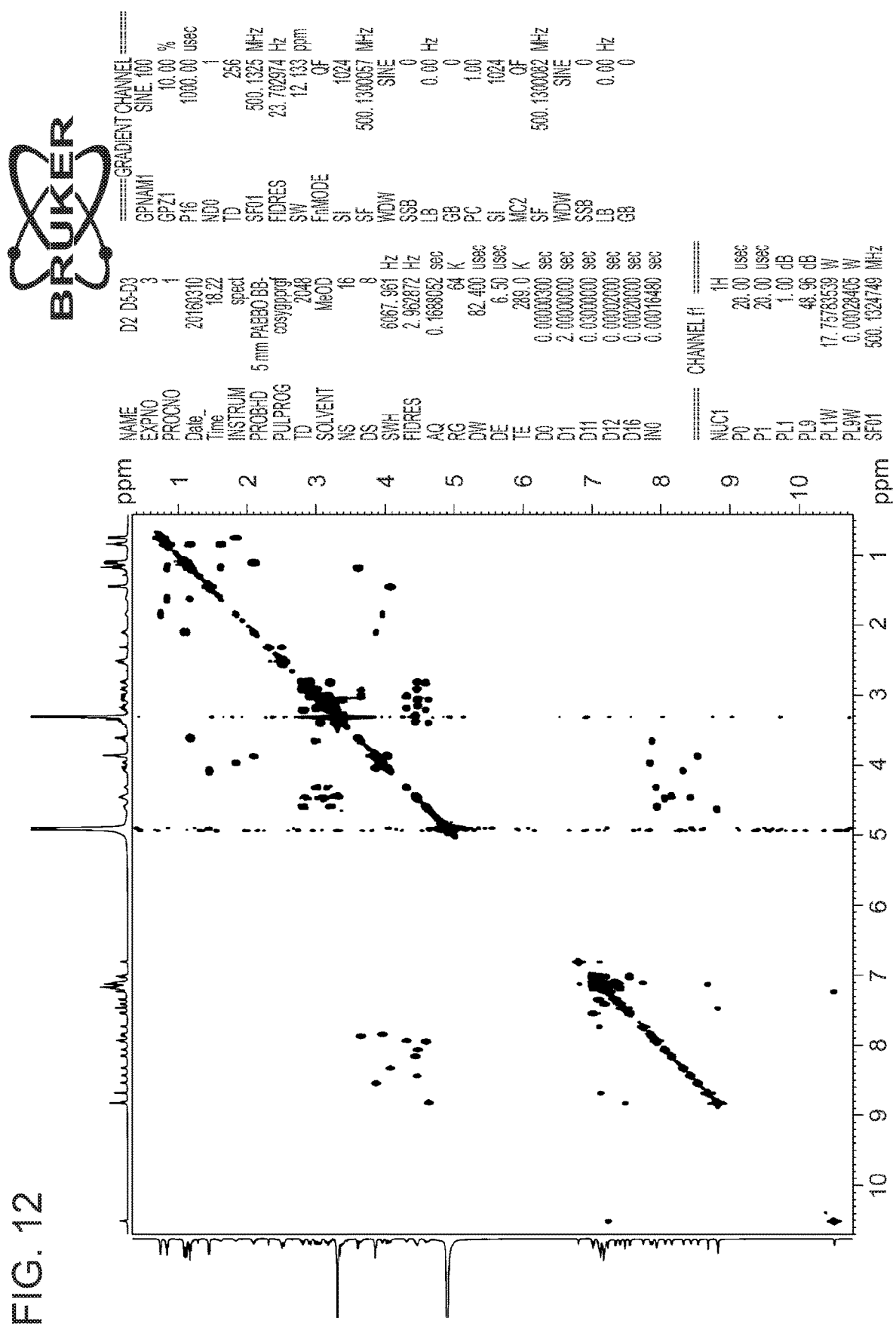

FIG. 12. $^1$H-$^1$H COSY NMR spectrum of DD5-o in CD$_3$OH at 289 K.

Figure 13:
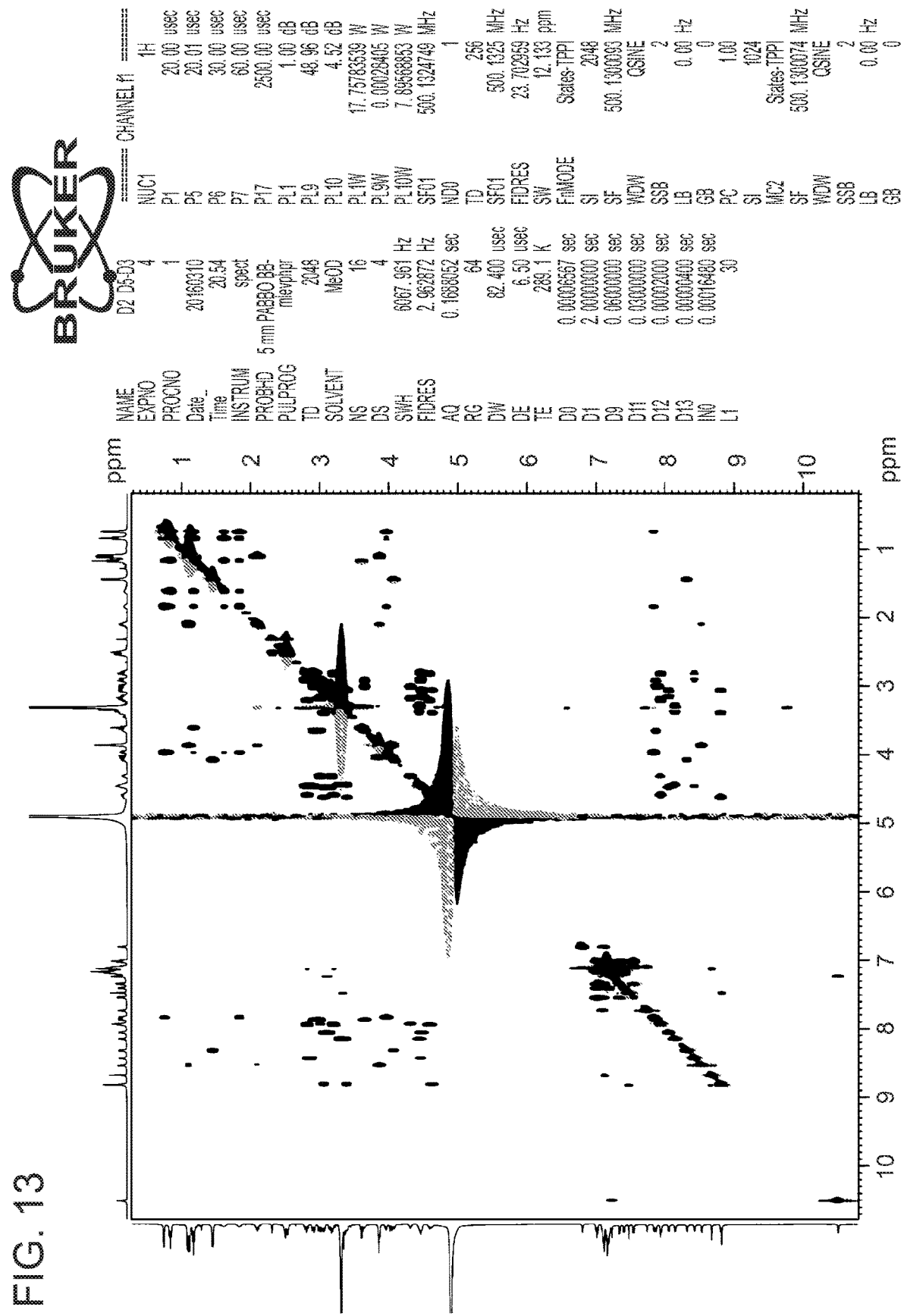

FIG. 13. $^1$H-$^1$H TOCSY NMR spectrum of DD5-o in CD$_3$OH at 289 K.

Figure 14:
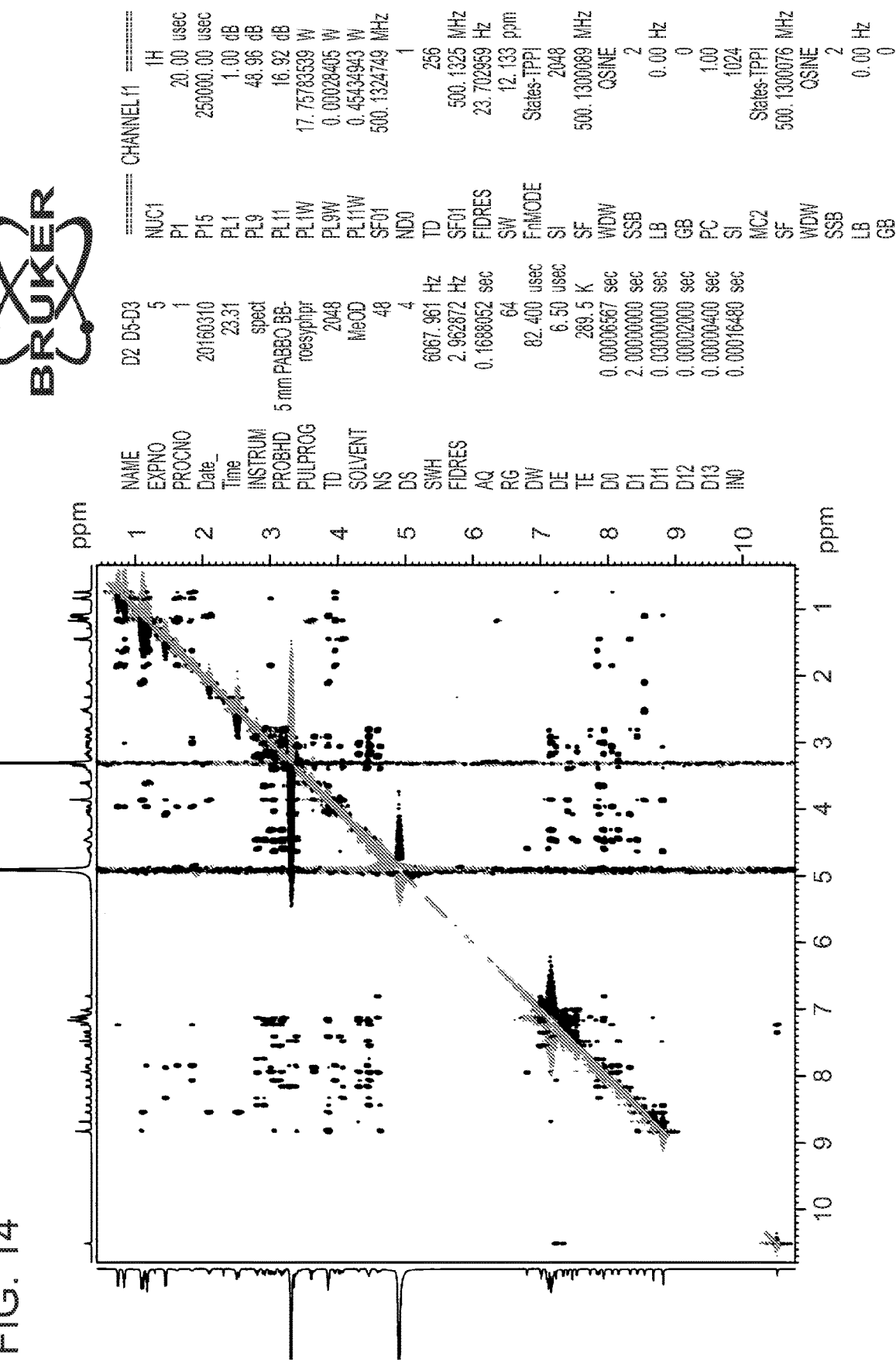

FIG. 14. $^1$H-$^1$H ROESY NMR spectrum of DD5-o in CD$_3$OH at 289 K.

Figure 15A:
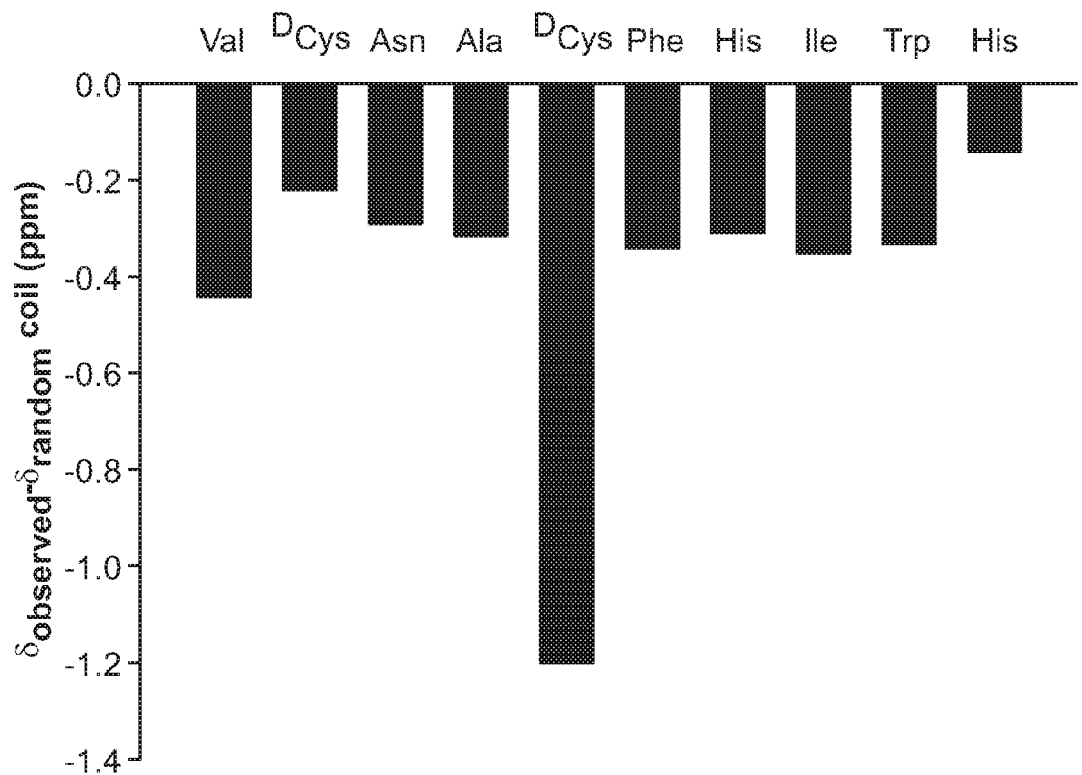
Figure 15B:
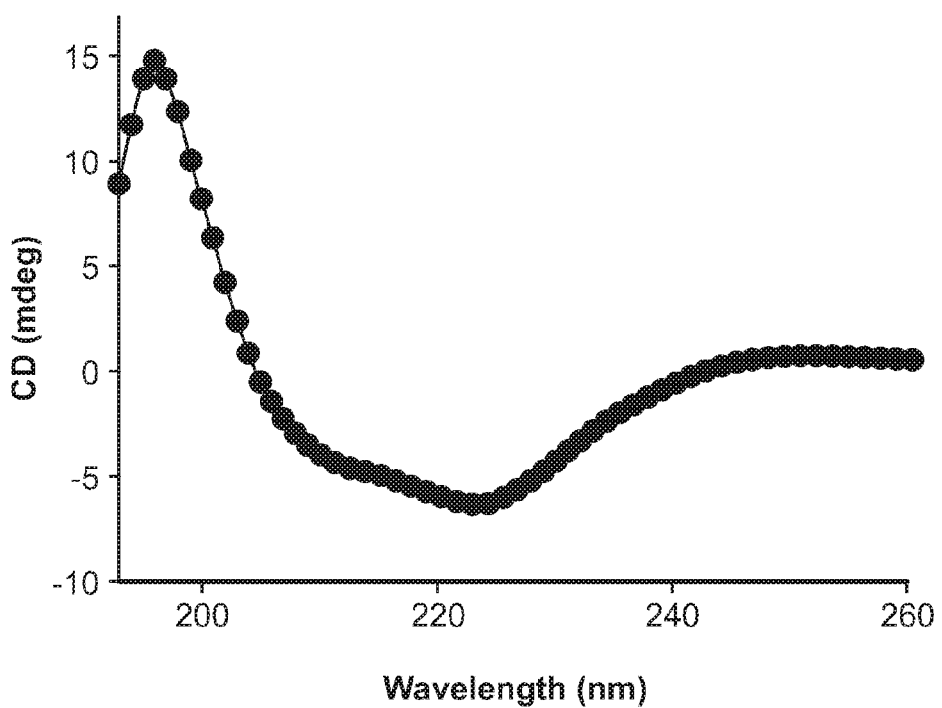

FIGS. 15A and 15B. Secondary structure analysis of DD5-o using NMR chemical shift values and CD spectroscopy. 15A. Residue-by-residue deviation of Hα chemical shifts with respect to random coil values (see SEQ ID NO: 6). Large, negative deviations across the peptide are consistent with a well-folded helical structure for DD5-o. For the alkylated D-Cys residues, the Hα chemical shift for an oxidized L-Cys was used. Random coil Hα chemical shifts were obtained from BMRB-Biological Magnetic Resonance Bank database, which are reported in water. However, a good correlation has been found between Hα chemical shifts in CD$_3$OD and those reported in water. 15B. CD spectrum of 0.1 mg/mL DD5-o in methanol showed a helical signature, and supports the NMR results. FIG. 15A discloses SEQ ID NO: 6.

Figure 16A:
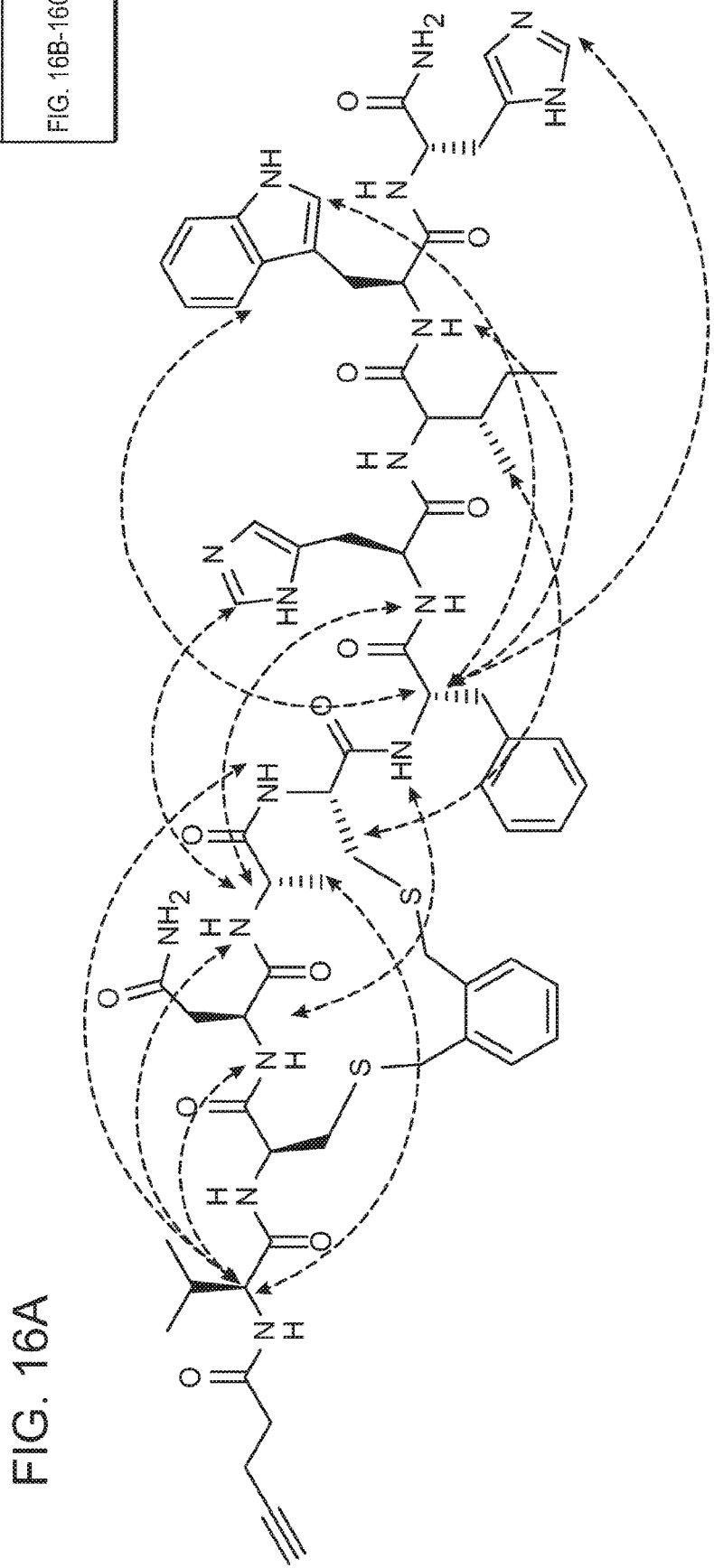
Figure 16B:
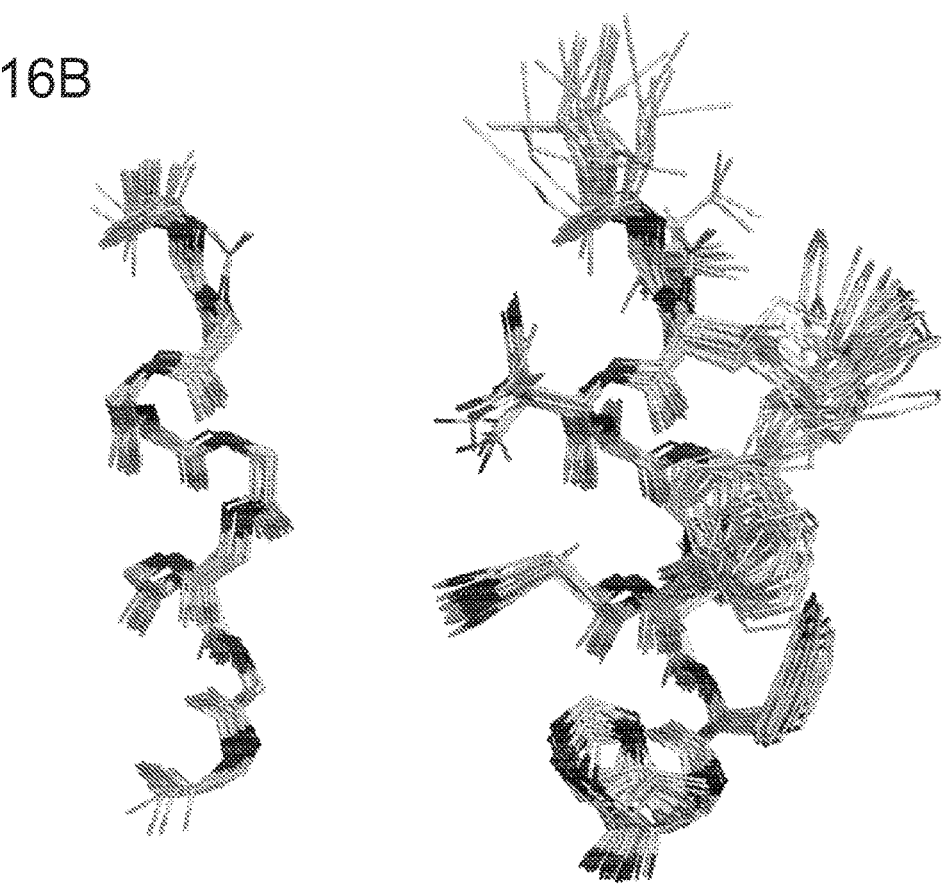
Figure 16C:
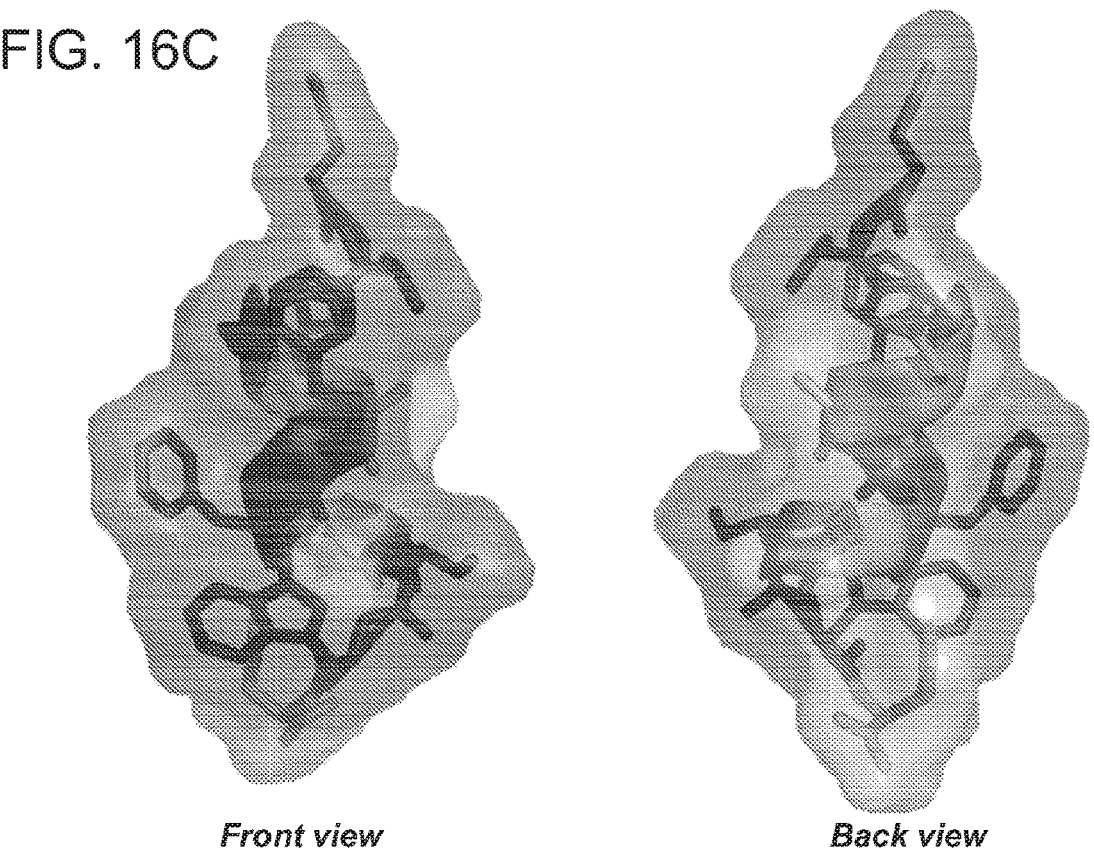

FIGS. 16A-16C. Solution structure of DD5-o. 16A. Diagram showing long-range NOEs used for structure determination of DD5-o. 16B. Ensemble of 25 lowest-energy solution structures showing the overlay of the backbone only (left) and backbone with side chains (right). Backbone RMSD for this overlay was 0.44 Å, and all-heavy-atom RMSD was 1.1 Å. 16C. Surface representation of DD5-o, where hot spot residues, linker and cap are highlighted in red. Front view (left) shows the extended hydrophobic surface on one face of the peptide, which includes the hot spot residues. Rear view (right) shows residues found to be non-essential residues for activity (gray).

Figure 17:
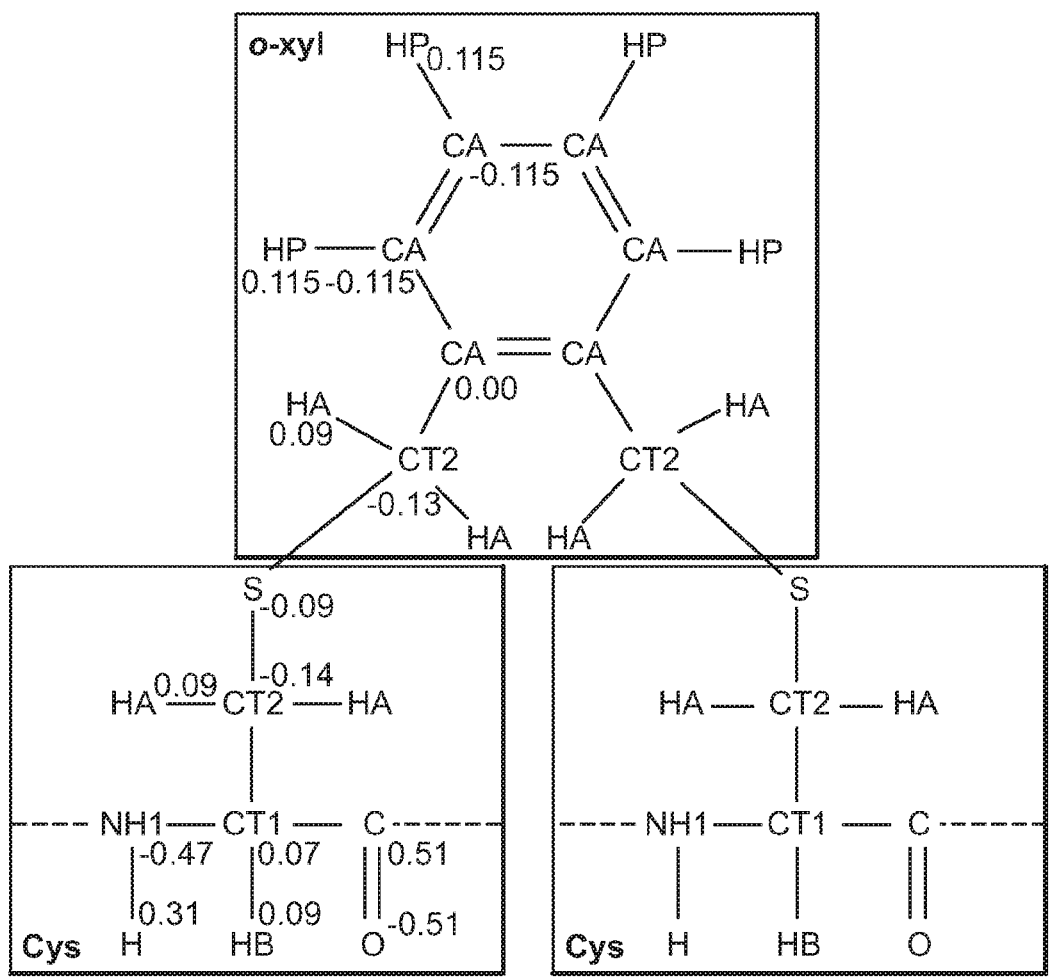

FIG. 17. Atom type definitions applied to linker atoms for molecular dynamics simulations. CHARMM atom types and charges are noted for each atom in each D-Cys residue and the ortho-xylene linker.

Figure 18:
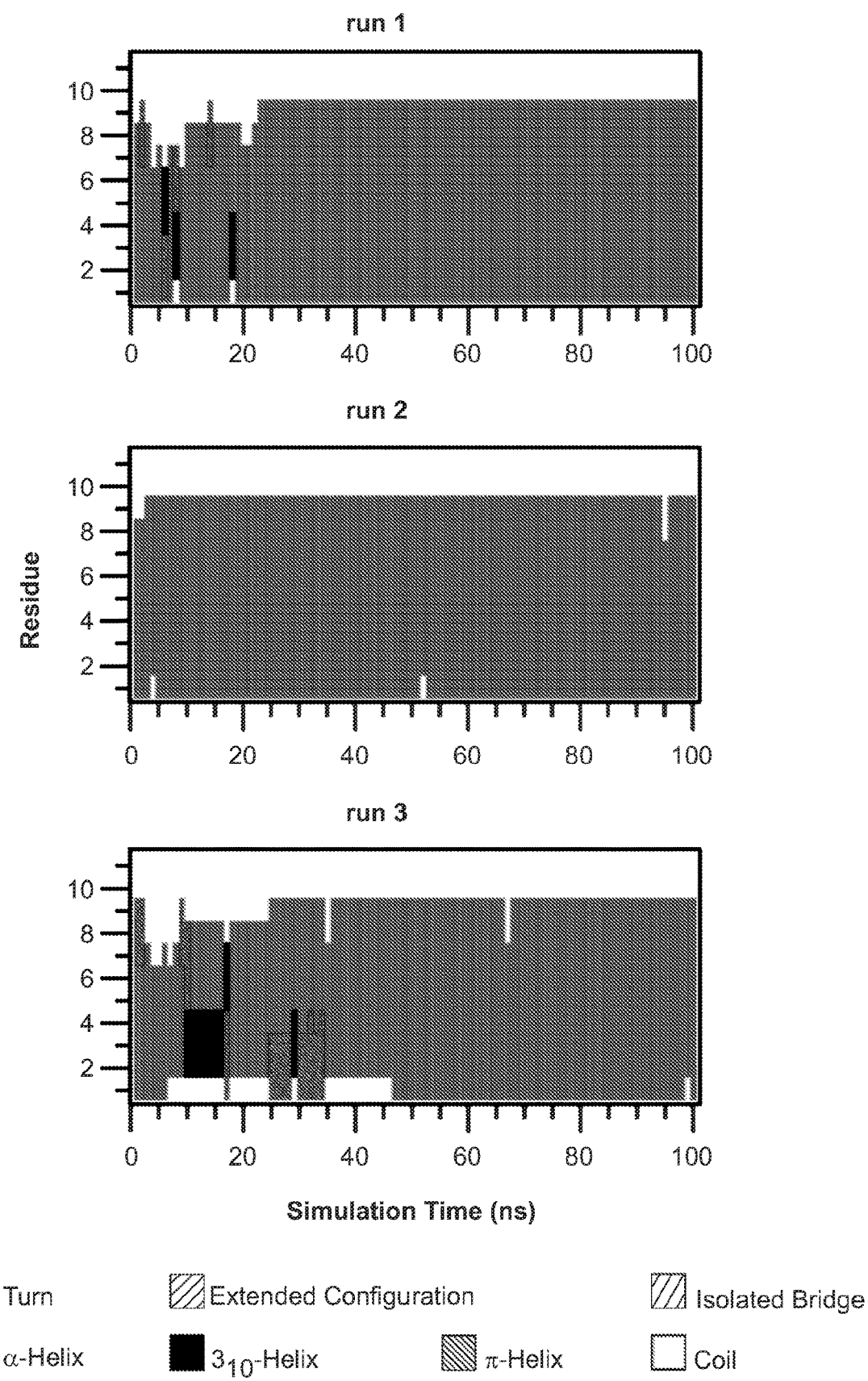

FIG. 18. Three independent 100-ns trajectories for DD5-o. These graphs illustrate overall secondary structure, as calculated using STRIDE, for residue during each 100 ns production run.

Figure 19C:
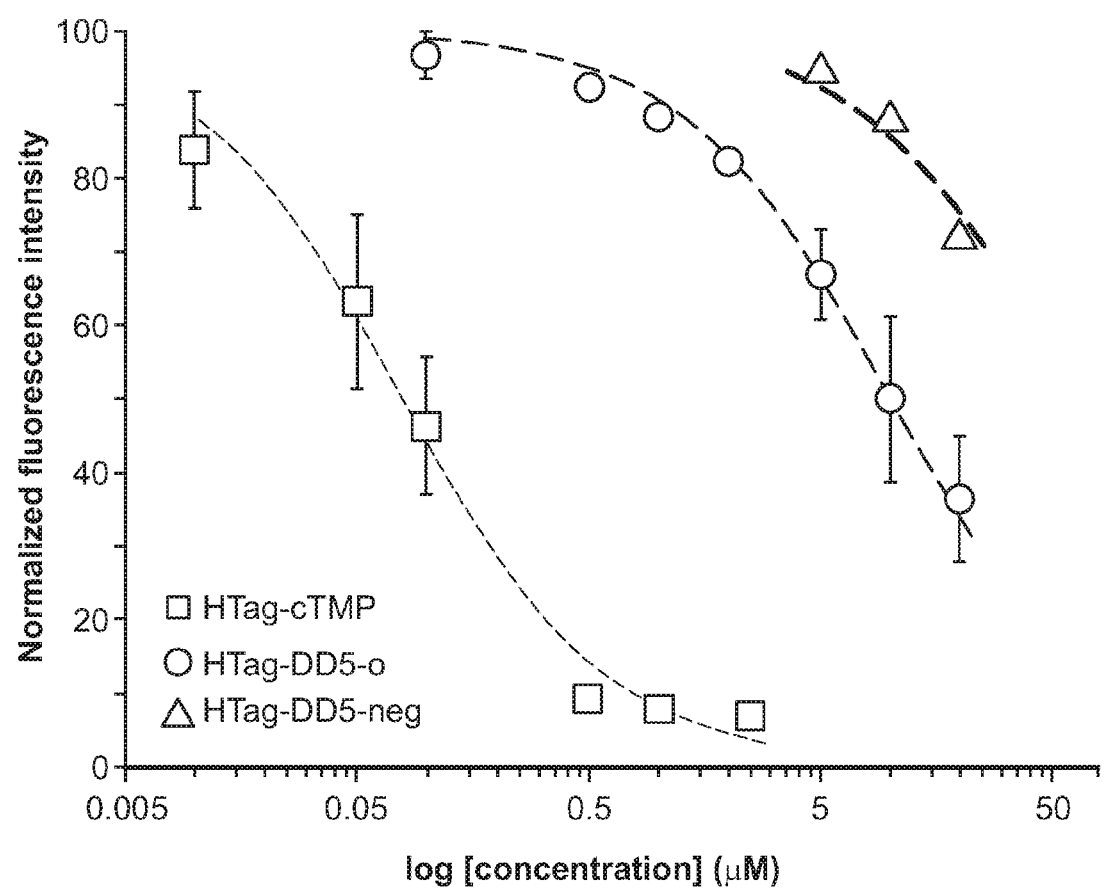
Figure 20:
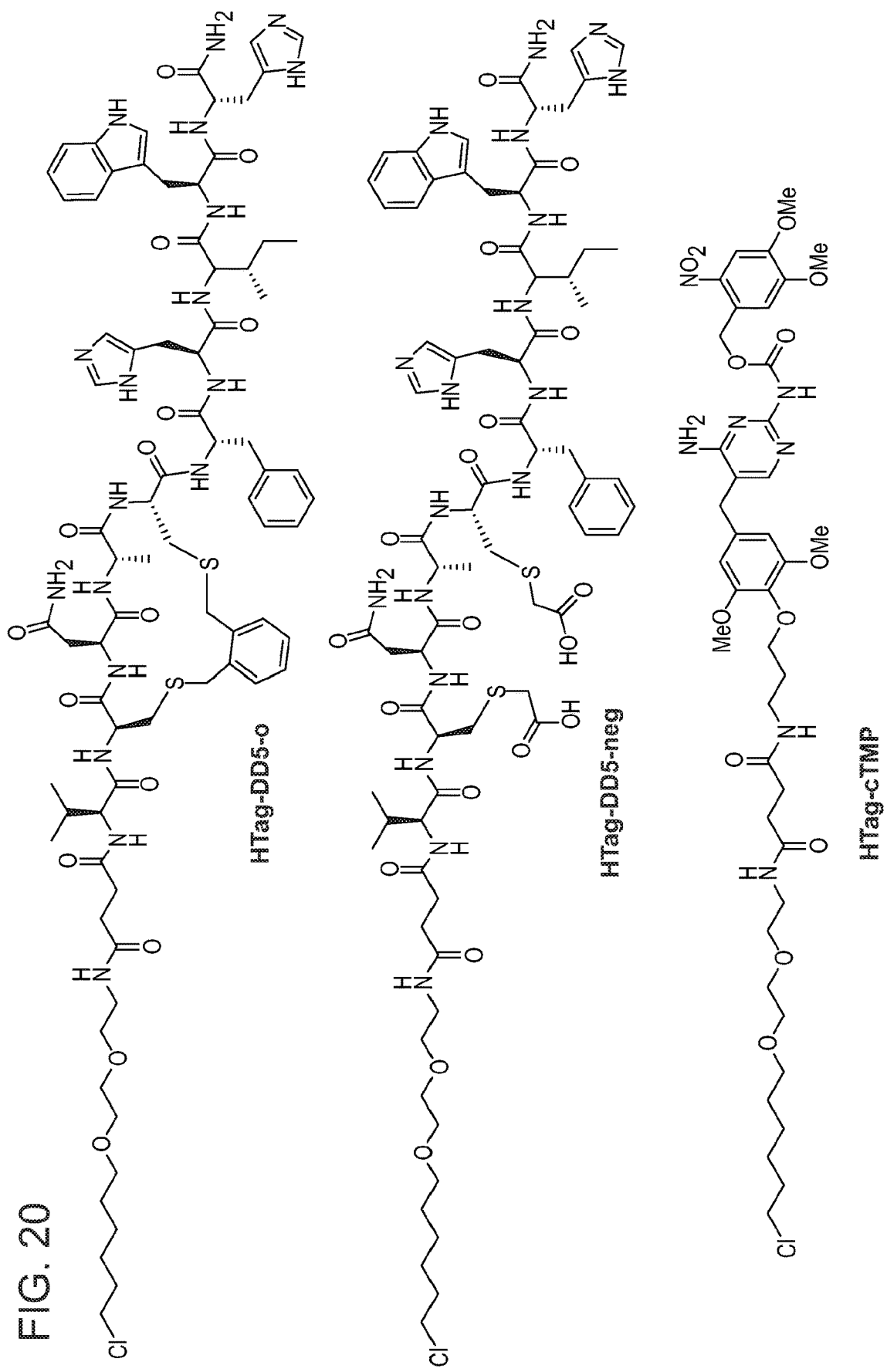

FIGS. 19A-19C. Chloroalkane Penetration Assay quantitates relative cytosolic access of exogenously added DD5-o. 19A. Schematic showing the experimental procedure of CAPA, which uses a HaloEnzyme-GFP-expressing HeLa cell line. Untreated cells labelled with HTag-TAMRA showed a large increase in red fluorescence as measured by flow cytometry. For CAPA, cells are pre-treated with vehicle or peptide, washed, and chased with HTag-TAMRA. Cells treated with cell-penetrant molecules have had their Haloenzyme blocked, thus preventing the HTag-TAMRA from covalently labeling the cells. 19B. Representative images of cells after CAPA, showing Haloenzyme-GFP fluorescence, Halotag-TAMRA fluorescence and the overlay of the two. A representative image of cells treated with HTag-cTMP at 2.5 µM shows roughly 90% inhibition of the Halotag-TAMRA signal. A representative image of cells treated with HTag-DD5-o at 10 µM shows roughly 50% inhibition of signal. 19C. Dose-dependence of Halotag-TAMRA signal after pre-incubation with different concentrations of HTag-cTMP, HTag-DD5o, and the negatively charged, linear variant HTag-DD5-neg (FIG. 20). Representative flow cytometry data are provided in FIG. 22. Data was normalized using the values obtained for vehicle (0% Halotag-TAMRA signal inhibition) and for vehicle with no Halotag-TAMRA added (100% signal inhibition). Points are means from three independent experiments and error bars show standard deviation.

FIG. 20. Chemical structures of HTag-DD5-o, HTag-DD5-neg and HTag-DD5-cTMP.

Figure 21:
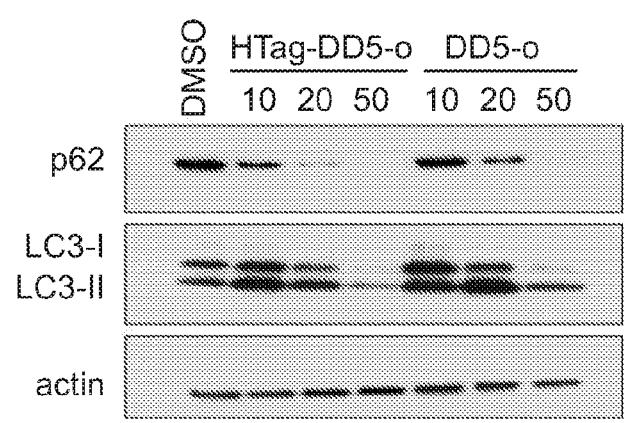
Figure 22A:
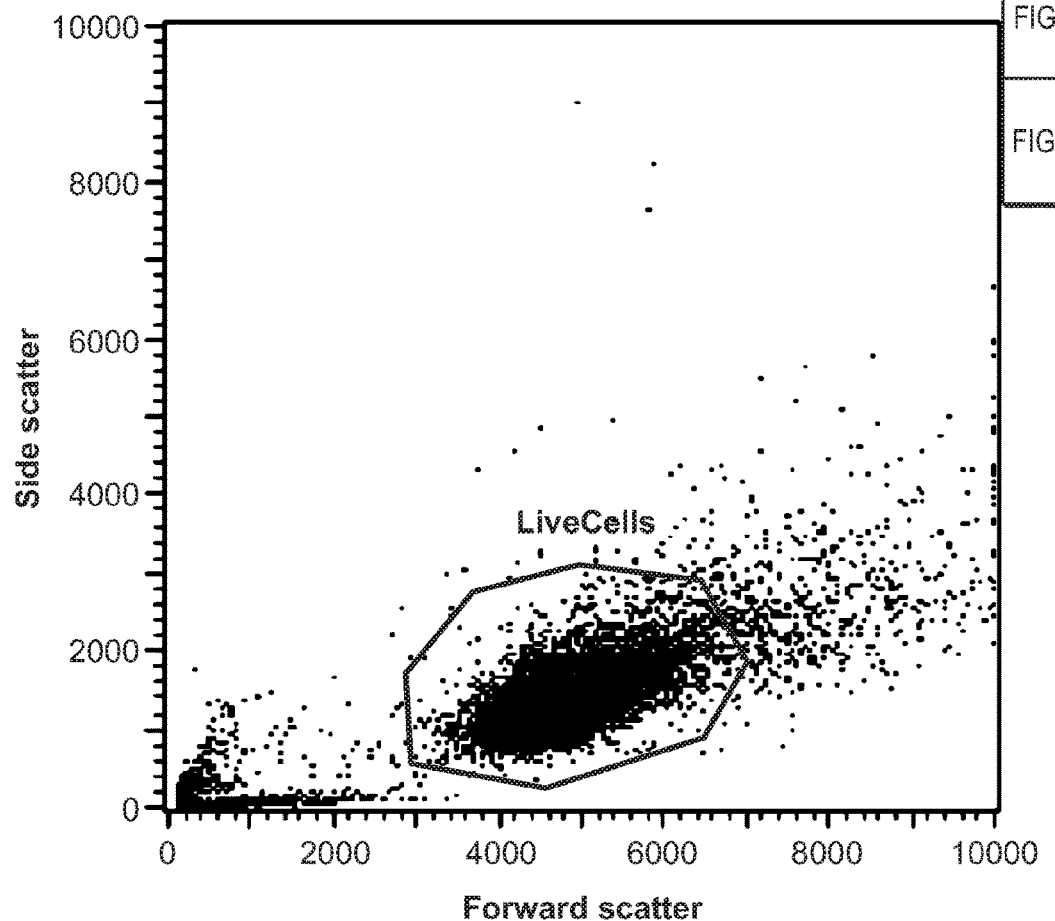
Figure 22B:
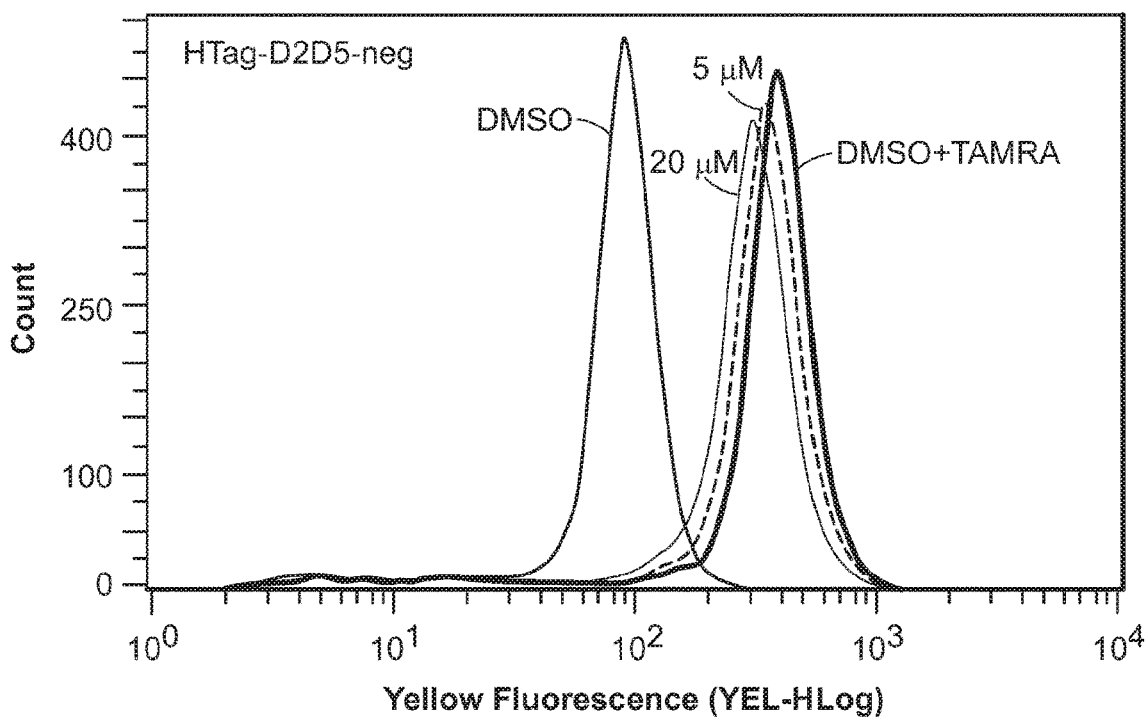
Figure 22C:
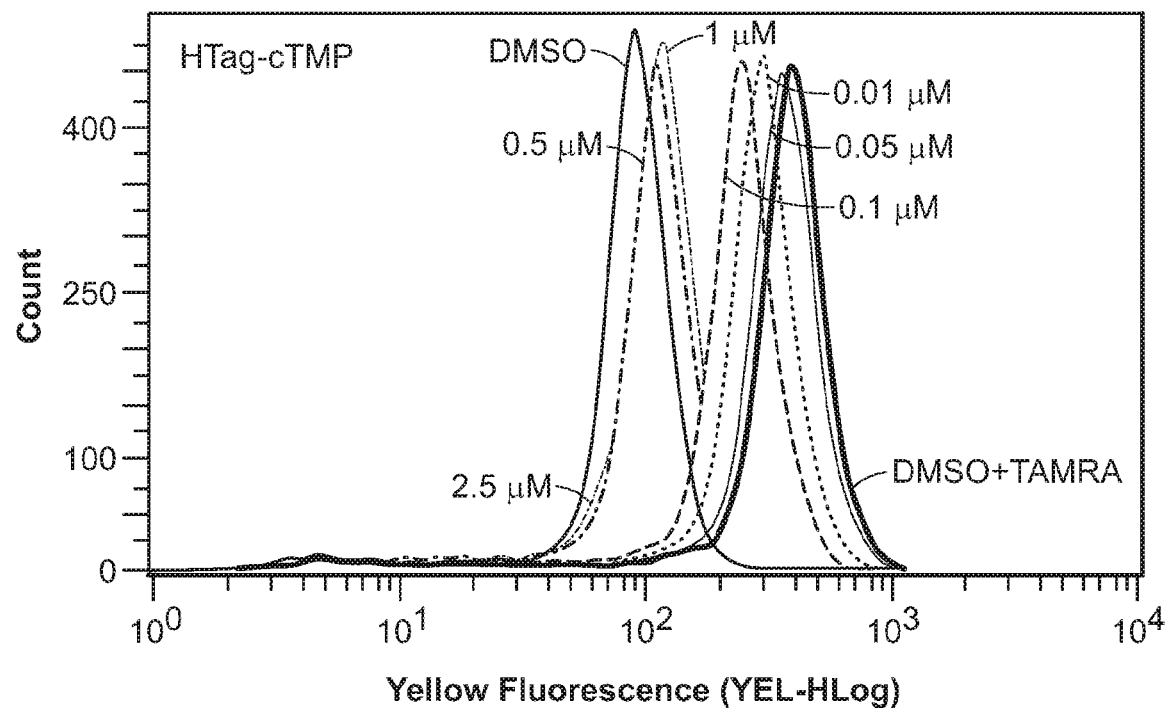
Figure 22D:
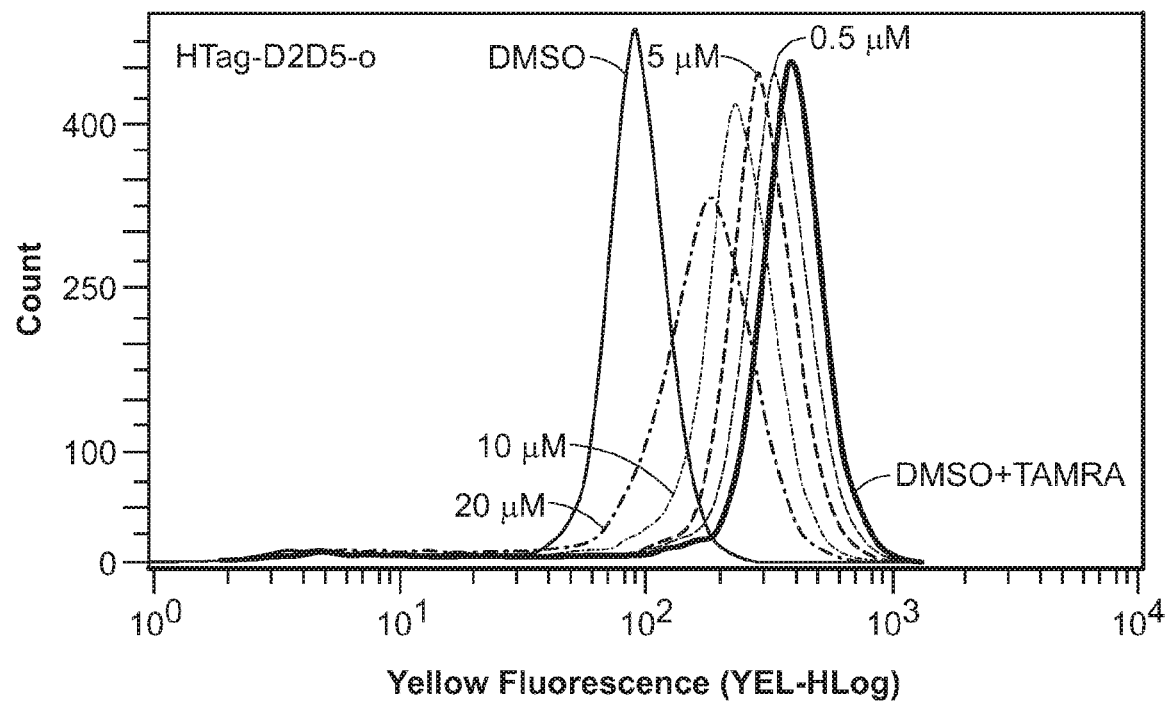

FIG. 21. HTag-DD5-o induces autophagy similarly to DD5-o. Autophagy induction in HeLa cells for additional peptides, analyzed using p62 and LC3 immunoblots. Actin is shown as a loading control. These results illustrate that HTag-DD5-o induces autophagy at 20 µM, to a similar extent as the pentynyl-capped DD5-o. Concentrations are noted in micromolar. Peptide sequences are given in Table 1.

FIGS. 22A-22D. Flow cytometry data from Chloroalkane Penetration Assay. These plots show a representative replicate of raw data obtained from Chloroalkane Penetration Assay. 22A. Each measurement involved 10,000 cells, gated as shown to count only live cells. This is the standard gating procedure for flow cytometry assays on HeLa cells. 22B. HTag-DD5neg is a negatively charged, non-cyclic variant of HTag-DD5-o. HTag-DD5neg shows little inhibition of HTag-TAMRA fluorescence, even at concentrations approaching its solubility limit. 22C. By contrast, small molecule HTag-cTMP does show dose-dependent inhibition of HTag-TAMRA fluorescence. 22D. HTag-DD5-o shows a similar trend as HTag-cTMP, but at roughly 100-fold higher concentration. This ratio is to be expected when comparing a cell-penetrant small molecule to a peptide. For each independent trial, mean fluorescence intensity values were calculated. These data were then normalized to the no-TAMRA signal (DMSO, shown in gray) as the 0% value, and the no-peptide signal (DMSO+TAMRA, shown in bright green) as the 100% value.

Figure 23:
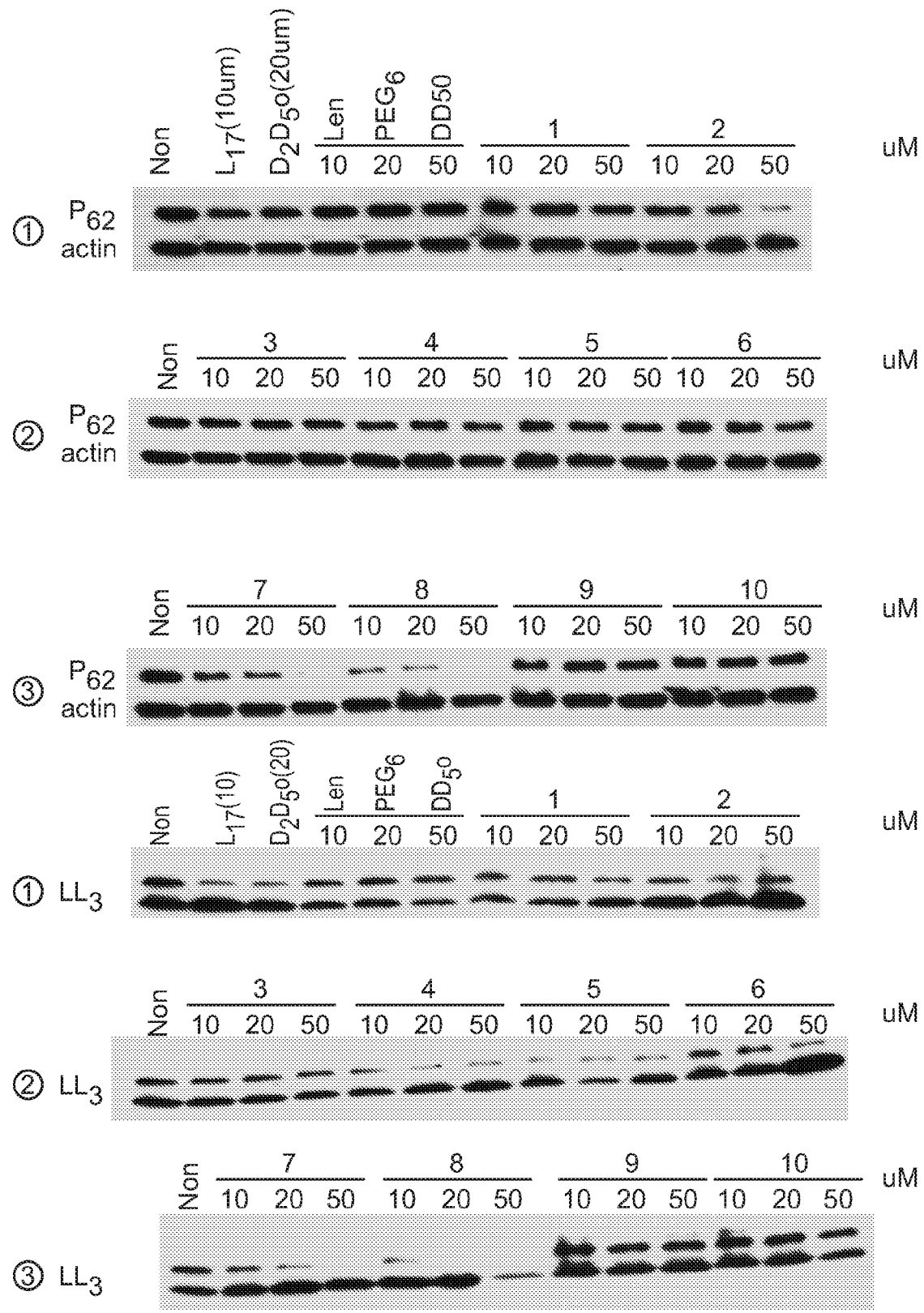
Figure 24:
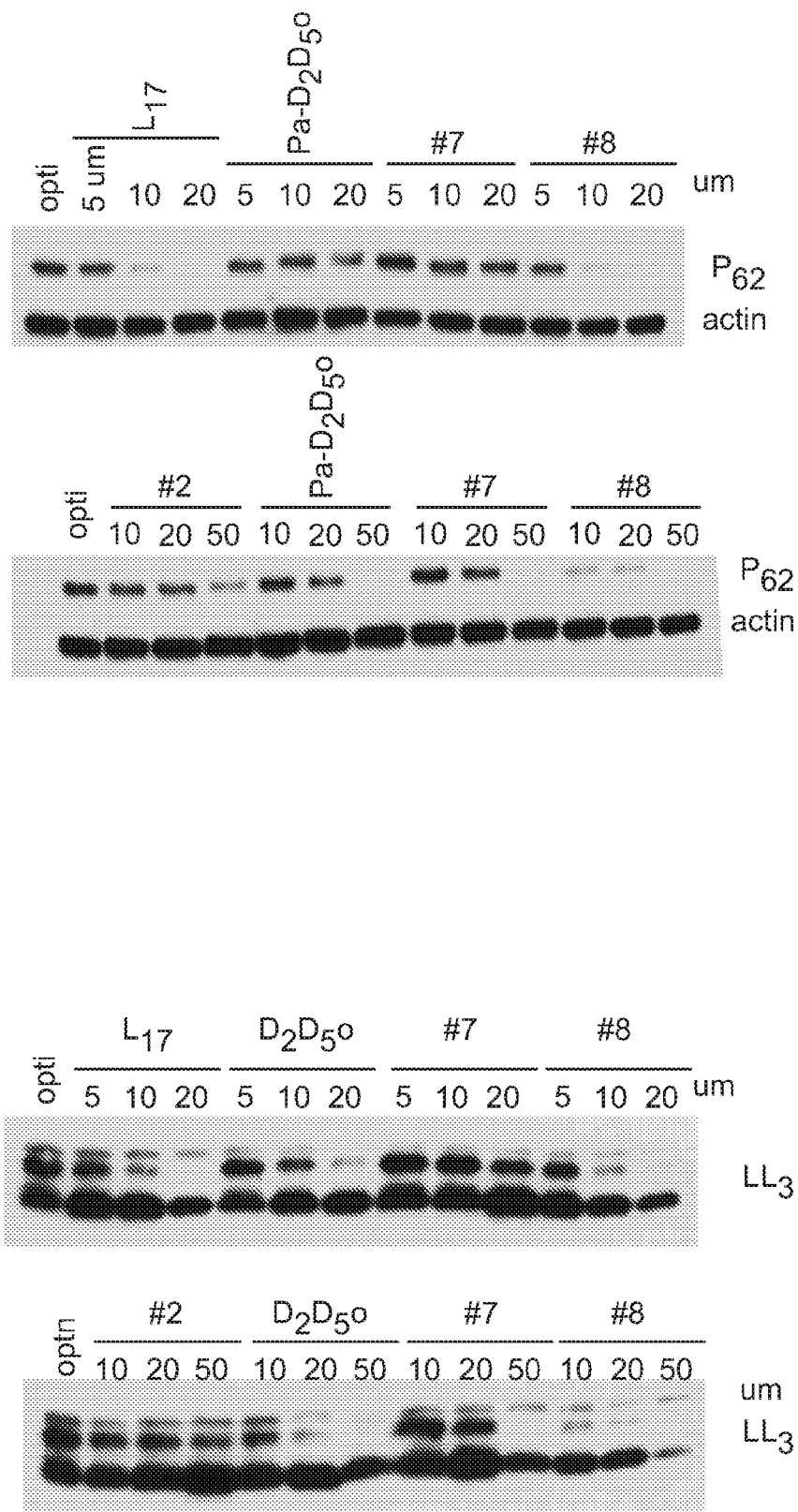

FIGS. 23 and 24 are Western blots showing p62 degradation (line labeled "p62") and LC3-I conversion to lipidated LC3-II (lines labeled "LC3") by additional peptides, using actin (line labeled "actin") as a loading control.

DETAILED DESCRIPTION

Provided herein are cell penetrating cyclic peptide, small-molecule mimics and methods of using such peptides and small-molecule mimics to induce cellular autophagy in vitro and in vivo.

In some aspects, disclosed herein are the design, synthesis and application of intrinsically cell-penetrant peptides derived from Tat-Beclin 1. Truncation and optimization of Tat-Beclin 1 produced a smaller, Tat-linked tool compound with greater potency. Then, a new, structure-independent stapling strategy is used to constrain the peptide into a stable structure that promotes activity and cell penetration. This strategy produced DD5-o, an autophagy-inducing peptide of only ten residues. DD5-o induces autophagy in vitro and in vivo as potently as Tat-Beclin 1, but DD5-o lacks Tat and has minimal overall charge at neutral pH. The solution structure of DD5-o was solved and, surprisingly, a helical conformation stabilized by a new type of (i, i+3) staple was revealed. Since Beclin 1 and its immediate effectors are all oriented towards the cytosol, the cytosolic penetration of this new class of stapled peptides was measured. Most cell penetration assays require labelling with a fluorescent dye, and often cannot distinguish between endosomal and cytosolic localization. A new assay that quantitatively measures cytosolic delivery of an exogenously added peptide was developed and described in detail in U.S. Provisional Application No. 62/424,955, filed Nov. 21, 2016, and corresponding to U.S. Pat. No. 10,620,214, which is incorporated herein by reference in its entirety. This straightforward assay demonstrates the intrinsically cell-penetrant nature of DD5-o, and will be generally applicable for quantitative measurement of cytosolic penetration of nearly any exogenously added molecule.

Thus, the cyclic/stapled peptides disclosed herein (such as DD5-o and derivatives) can present real lead for pre-clinical and clinical development. Furthermore, the DD5-o pharmacophore can be used to design and/or screen for small-molecule drugs. For example, the NMR structure of stapled peptide provides 3D search queries that can be used to search (e.g., in silico) small molecule databases to find matches, or to design small molecules with similar properties. Additionally, based on the helical confirmation of DD5-o, small-molecule helix mimics can also be designed, such as those disclosed in Whitby and Boger, *Acc Chem Res* 2012, 45, 1698, incorporated herein by reference in its entirety.

Definitions

Unless defined otherwise, all technical and scientific terms used herein have the meaning commonly understood by a person skilled in the art of the present disclosure. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant a substance selected from a protein, a peptide, an antibody, a nucleic acid molecule, or fragments thereof, and an organic, organometallic or inorganic compound, each of which can be present as free of other substances. An agent also includes compositions, such as formulations, complexes, composites, matrices and the like, that contain one or more of these substances. An agent can be the active compound or constituent in a therapeutic setting.

By "ameliorate" or "modulate" is meant to decrease, suppress, attenuate, diminish, arrest, or stabilize the development or progression of a disease or a chemical reaction.

By "amino acid" or "residue" is meant a free compound or unit in a peptide or protein that has the general structure $H_2N-C(R_aR_b)-COOH$ or $-HN-C(R_aR_b)-CO-$. $R_a$ and $R_b$ can be selected, for example, from the carbon substituents found in the 20 natural amino acids and those unnatural ones known in the art. Amino acids can be in either the L or S (natural) or D or R (unnatural) stereochemical configuration using the optical rotation D/L system of nomenclature or the Cahn-Ingold-Prelog R/S system.

By "cell penetrating" as applied to a peptide is meant that the peptide is capable of crossing the cell membrane whether by endocytosis, passively permeable and/or some other mechanism.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, the term "detect" refers to identifying the presence, absence or amount of the analyte to be detected. One of ordinary skill in the art readily appreciates that measurement methods inherently possess a limit(s) to its lowest and highest levels of detection. Thus, an indication of not detected as used herein is not to be construed to mean the analyte is not present at all. It is simply not present between the upper or lower limits of the detection method.

By "disease" is meant any condition or disorder that damages or interferes with the normal function of a cell, tissue, or organ. In one embodiment, the disease is a condition having impaired autophagy, including but not limited to neurodegenerative disorders, cancers, muscular diseases, inflammatory bowel disease, autoimmune and/or inflammatory disorders, infectious diseases (e.g., infection with intracellular pathogens such as virus or bacteria), metabolic disorders, innate and adaptive immune disorders, aging, hepatic insulin resistance/diabetes, lysosomal storage disorders, muscular dystrophy, and cystic fibrosis.

"Enantiomers" are a pair of stereoisomers that are non-superimposable mirror images of each other. A mixture of a pair of enantiomers in any proportion can be known as a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, optically substantially pure forms and intermediate mixtures. Optically active (R)- and (S)-isomers can be prepared, for example, using chiral synthons or chiral reagents, or resolved using conventional techniques.

Another system used to describe enantiomers is based on how a compound rotates plane-polarized light. "D" means the light is rotated to the right, while "L" means the light is rotated to the left. These designations do not necessarily correlate with absolute stereochemistry. For example, an S-enantiomer of one compound may be a D or L configuration, which is determined experimentally. For the natural amino acids, a correlation has been made where S-configurations correspond to L designation, while unnatural R-configurations correspond to D designations. As used herein, an underlined amino acid indicates the stereochemistry is the unnatural R and D configuration, where non-underlined residues are the natural S and L configuration.

An isomer/enantiomer can, in some embodiments, be provided substantially free of the corresponding enantiomer, and can also be referred to as "optically enriched," "enantiomerically enriched," "enantiomerically pure" and "non-racemic," as used interchangeably herein. These terms refer to compositions in which the percent by weight of one enantiomer is greater than the amount of that one enantiomer in a control mixture of the racemic composition (e.g., greater than 1:1 by weight). For example, an enantiomerically enriched preparation of the S enantiomer means a preparation of the compound having greater than about 50% by weight of the S enantiomer relative to the R enantiomer, such as at least about 75% by weight, further such as at least about 80% by weight. In some embodiments, the enrichment can be much greater than about 80% by weight, providing a "substantially enantiomerically enriched," "substantially enantiomerically pure" or a "substantially non-racemic" preparation, which refers to preparations of compositions which have at least about 85% by weight of one enantiomer relative to other enantiomer, such as at least about 90% by weight, and further such as at least about 95% by weight. In certain embodiments, the compound provided herein is made up of at least about 90% by weight of one enantiomer. In other embodiments, the compound is made up of at least about 95%, about 98%, or about 99% by weight of one enantiomer.

In some embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, the compound mixture has an (S)-enantiomeric excess of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more. In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5% or more. In some other embodiments, the compound mixture has an (R)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In other embodiments, the compound mixture contains identical chemical entities except for their stereochemical orientations, namely (S)- or (R)-isomers. For example, if a compound disclosed herein has a —CH(R)— unit, and R is not hydrogen, then the —CH(R)— is in an (S)- or (R)-stereochemical orientation for each of the identical chemical entities. In some embodiments, the mixture of identical chemical entities is a racemic mixture of (S)- and (R)-isomers. In another embodiment, the mixture of the identical chemical entities (except for their stereochemical orientations), contain predominately (S)-isomers or predominately (R)-isomers. For example, the (S)-isomers in the mixture of identical chemical entities are present at about 55%, about 60%, about 65%, about 70%, about 75%, about 80%, about 85%, about 90%, about 95%, about 96%, about 97%, about 98%, about 99%, about 99.5%, or more, relative to the (R)-isomers. In some embodiments, the (S)-isomers in the mixture of identical chemical entities are present at an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In another embodiment, the (R)-isomers in the mixture of identical chemical entities (except for their stereochemical orientations), are present at about 55%, about 60%, about 65%, about 70%, about 75%, about 80%, about 85%, about 90%, about 95%, about 96%, about 97%, about 98%, about 99%, about 99.5%, or more, relative to the (S)-isomers. In some embodiments, the (R)-isomers in the mixture of identical chemical entities (except for their stereochemical orientations), are present at a (R)-enantiomeric excess greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

Enantiomers can be isolated from racemic mixtures by any method known to those skilled in the art, including chiral high pressure liquid chromatography (HPLC), the formation and crystallization of chiral salts, or prepared by asymmetric syntheses. See, for example, Enantiomers, Racemates and Resolutions (Jacques, Ed., Wiley Interscience, New York, 1981); Wilen et al., Tetrahedron 33:2725 (1977); Stereochemistry of Carbon Compounds (E. L. Eliel, Ed., McGraw-Hill, N Y, 1962); and Tables of Resolving Agents and Optical Resolutions p. 268 (E. L. ElM, Ed., Univ. of Notre Dame Press, Notre Dame, Ind. 1972).

Optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid. The separation of the mixture of diastereoisomers by crystallization followed by liberation of the optically active bases from these salts affords separation of the isomers. Another method involves synthesis of covalent diastereoisomeric molecules by reacting disclosed compounds with an optically pure acid in an activated form or an optically pure isocyanate. The synthesized diastereoisomers can be separated by conventional means such as chromatography, distillation, crystallization or sublimation, and then hydrolyzed to deliver the enantiomerically enriched compound. Optically active compounds can also be obtained by using active starting materials. In some embodiments, these isomers can be in the form of a free acid, a free base, an ester or a salt.

By "effective amount" is meant the amount of an active agent required to ameliorate the symptoms of a disease relative to an untreated subject. In some cases, the effective amount is sufficient to palliate, ameliorate, stabilize, reverse or slow the progression of a disease or condition having impaired autophagy, including but not limited to neurodegenerative disorders, cancers, muscular diseases, inflammatory bowel disease, autoimmune and/or inflammatory disorders, infectious diseases (e.g., infection with intracellular pathogens such as virus or bacteria), metabolic disorders, innate and adaptive immune disorders, aging, hepatic insulin resistance/diabetes, lysosomal storage disorders, muscular dystrophy, and cystic fibrosis. The amount can be sufficient to effect a beneficial or desired clinical result. The effective amount of active agent(s) disclosed herein for therapeutic treatment of a disease varies depending upon a number of factors, including, but not limited to, the manner of administration, the age, body weight, and general health of the subject. A therapeutically effective amount can be administered in one or more doses. The attending physician or veterinarian can decide the appropriate amount and dosage regimen.

By "inducing" is meant to cause a chemical reaction to occur where the reagents may or may not react without the inducing agent. For example, inducing phosphorylation of a protein can involve activating a kinase and bringing it into proximity with another protein such that a residue in that protein can undergo addition of a phosphate group.

As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in J. Pharmaceutical Sciences (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecyl sulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, lactic acid, trifluoracetic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The salts can be prepared in situ during the isolation and purification of the disclosed compounds, or separately, such as by reacting the free base or free acid of the compound with a suitable base or acid, respectively. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines, including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

By "reference" is meant a standard or control condition.

The term "subject," "patient" or "individual" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Peptide Therapeutics

Peptides are synthetically tractable, they can be optimized to high affinity and selectivity, and they often have good safety and tolerability profiles in animals and humans. Nevertheless, the clinical utility of conventional peptides has been limited by a number of factors. Short peptides are often poorly structured in aqueous solution, which can limit their affinity for their targets. One of the largest limitations of peptide drugs is poor membrane permeability, making delivery to intracellular targets difficult.

One solution to the inherent limitations of peptides is macrocyclization, which is typically applied as a structure-promoting conformational constraint. Several chemistries are available that capitalize on the reactivity of cysteine residues. For example, thioether ligation was used to link a cysteine to a bromoacetylated ornithine, yielding an alternative to lactam bridge formation. Another effective result is that these cyclic peptides are generally more stable to proteolytic degradation. In some cases, cyclic peptides have increased cytosolic penetration compared to linear peptides.

Linear peptides, such as Tat-beclin-1, have been identified as inducing autophagy, a cellular lysosomal degradation pathway that defends again infection, neurodegenerative disorders, cancer and ageing. Tat-beclin-1 was identified using an epitope of the HIV-1 virulence factor Nef. This peptide has been demonstrated to bind the autophagy inhibitor GAPR-1, which negatively regulates autophagy. Other studies indicated Tat-beclin-1 decreases protein aggregates and soluble protein concentrations. Given the need in the art for more targeted and pharmacologically available therapeutics, Tat-beclin-1 is an attractive target for development of constrained peptides through macrocyclization.

Previous work on helical peptides has demonstrated the major benefits of macrocyclization for promoting peptide structure and function, but applying cyclic constraints to non-helical structures has not been as straightforward. While the results from screening large, unbiased libraries of cyclic peptides clearly indicate that this is a valuable chemical space for protein inhibitors, rational design of small, non-helical cyclic peptides is still largely trial-and-error. Therefore, the present disclosure provides, inter alia, the design and execution of synthetic cyclic peptides with the targeted approach to a molecule with increased properties for inducing autophagy.

Autophagy-Inducing Cyclic Peptides

Autophagy is a fundamental and phylogenetically conserved self-degradation process that is characterized by the formation of double-layered vesicles (autophagosomes) around intracellular cargo for delivery to lysosomes and proteolytic degradation. Tat-beclin, derived from a region of the autophagy protein, beclin 1, which binds human immunodeficiency virus (HIV)-1 Nef, is a potent inducer of autophagy, and interacts with a negative regulator of autophagy, GAPR-1 (also called GLIPR2). Beclin 1, an essential autophagy protein in the class III phosphatidylinositol-3-OH kinase (PI(3)K) complex, is involved in autophagic vesicle nucleation, and interacts with the HIV-1 virulence factor, Nef. Investigating this interaction led to the identification of Tat-beclin-1, an HIV-1 Tat protein transduction domain (YGRKKRRQRRR; SEQ ID NO: 20) attached via a diglycine linker to 18 amino acids derived from amino acids 267-284 of beclin 1 (Shoji-Kawata et al., Nature 484:201-206, 2013, US App. Pub. No. US2015/0359840; each incorporated herein by reference in its entirety). Tat-beclin-1 decreases the accumulation of polyglutamine expansion protein aggregates and the replication of several pathogens (including HIV-1) in vitro, and reduces mortality in mice infected with chikungunya or West Nile virus.

While Tat-beclin-1 has demonstrated good activity in affecting autophagy pathways and functions, it is a linear peptide susceptible to degradation and requires the Tat poly-cationic sequence for cellular permeability. Linear peptides can often fluctuate between multiple 3-dimensional orientations at any given time, such that the needed conformation to interact with the target protein may only be accessed sporadically. To gain conformer control and design, peptides can be cyclized through a wide variety of linkers. Structure-activity relationship (SAR) studies often enlarge to synthesizing hundreds of variants of a molecule to narrow in on essential features for potency, which requires significant time and resources. However, rational design can focus attention to key molecular components in a more efficient and directed fashion. The rational design approach is greatly assisted by starting with a peptide epitope derived from a known protein binding partner. Ideally, this epitope accounts for a majority of the binding energy of the interaction by comprising the most important "hot spot" residues. Cyclization of peptides, for example, translates these epitopes to effective inhibitory peptides requires replacing the entire protein tertiary structure with a synthetic linker that stabilizes the epitope's highest-affinity 3D structure.

To date, computational methods for the prediction of cyclic peptide structure have not advanced to a stage where it is possible to predict the lowest-energy structural ensemble for a given cyclic peptide. This makes it impossible to predictively design specific cross-links to stabilize a desired loop structure within a cyclic peptide. Selection of the proper linker chemistry, length and positioning can only be done in a traditional SAR process. One way to accelerate this process is to introduce diverse conformational constraints at a late stage of synthesis. Described herein is an efficient method for late-stage conformational diversification of peptide epitopes using thiol bis-alkylation chemistry. This allows for rapid preparation and screening of many conformations of a given loop using a panel of linkers, experimentally searching for the highest-affinity conformation.

Thiol linkers produced by linking cysteine residues can provide stable linkers with increased conformational rigidity. Thiol bis-alkylation has rapid kinetics and broad sequence tolerance. Late-stage conformational diversification is introduced by including two thiol-containing amino acids at positions known to be non-essential for target binding. Utilizing thiol bis-alkylation chemistry, peptides can be cross-linked using a wide variety of different linkers by incubating them in solution with a variety of dibromomethyl aryl compounds (See, FIG. 4). Both L and D-cysteines are reacted efficiently. A major advantage of using this chemistry is that it is orthogonal to all natural amino acid functional groups including lysine and free N-termini, except for methionine. Strategically varying the thiol-containing amino acids, the relative positioning of the thiol-containing amino acids, and the linkers enabled rapid preparation of a large library of peptides with diverse 3D conformations from a single peptide epitope.

Beginning with Tat-beclin-1, a set of analogs were synthesized having the Tat sequence at the N-terminus, followed by two glycine residues before the beclin-1 peptide sequence. These Tat peptides T1-T46 are linear peptides where one or two amino acids were varied at a time (shown in bold in Table 2 below) to determine which were important for potency, which alterations decreased potency, or which had little effect compared to Tat-beclin-1 itself. FIG. 3 provides a summary of alterations in certain amino acids and their effect on autophagy. The alterations shown above the sequence indicate the residue that was substituted and the effect on activity. For example, the third residue N was replaced with a D in T3. The activity of T3 was less than Tat-beclin-1, indicating that the N amino acid was likely contributing to the peptide's overall function.

Another assessment of the beclin-1 peptide activity was performed using an alanine scan shown in FIG. 3. Certain residues in the beclin-1 peptide was replaced with an A leaving all other residues the same. For example, when the W residue was substituted with an A, the activity was the same as Tat-beclin-1, indicating this amino acid was not as crucial for overall activity.

The understandings gained from SAR studies with Tat-beclin-1 analogs informed the design of a series of cyclic peptides using bis-thiol linkers. The Tat sequence was removed from most analogs and replaced with an N-terminal carbonyl cap. Without wishing to be bound by theory, the cyclic nature of the peptides is believed to contribute to successful cell penetration as born out in the Examples below. Exemplary linkers are given in FIG. 4 and all share a terminal di-bromo substitution. Some peptides were investigated where the cysteines were reacted with allyl bromide or benzyl bromide, and thus were linear. The cyclic peptide compounds disclosed herein were assayed for inducing autophagy in a p62 degradation assay and an LC3 marker assay as described below.

Disclosed herein, in some embodiments, are compounds of Formulae I, II, IIIa, Mb, and IIIc:

Formula I

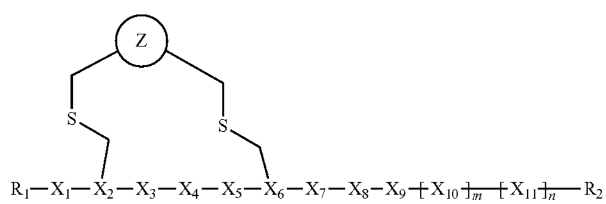

-continued
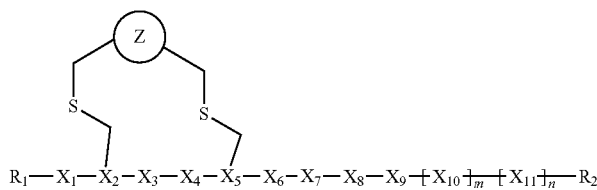
Formula II
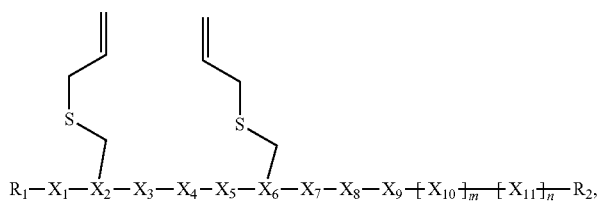
Formula IIIa
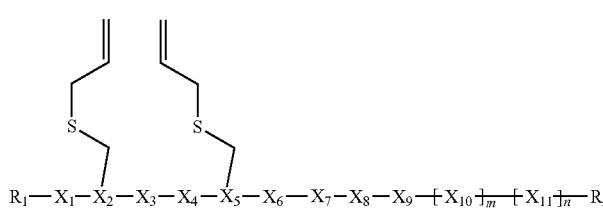
Formula IIIb
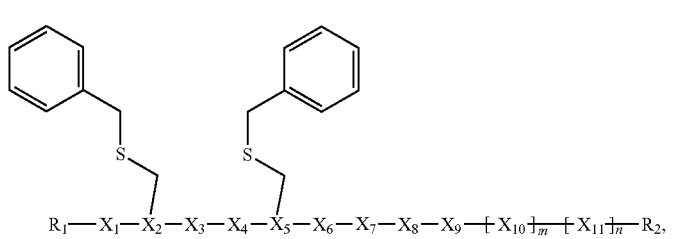 and
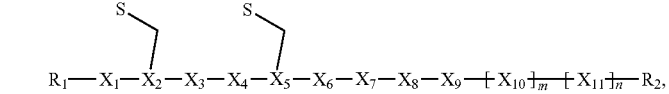
Formula IIIc
wherein:
$R_1$ is selected from
A)
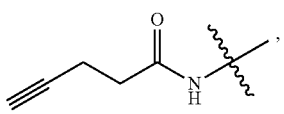
B)
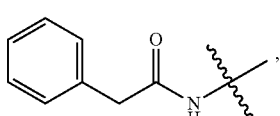
C)
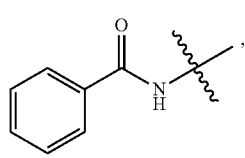
D)
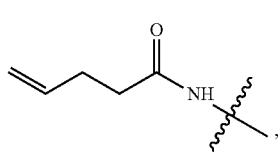
-continued
E)
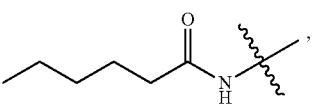
F)
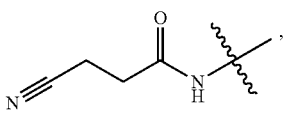
G)
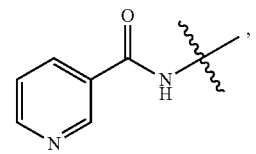

H) H₂N—,
I) MeC(O)—, and
J) c(FΦRRRRE) (SEQ ID NO: 14);
R₂ is —C(O)₂NH₂;
Z is selected from:

A)

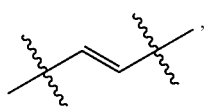

OP)

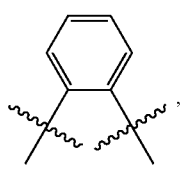

MP)

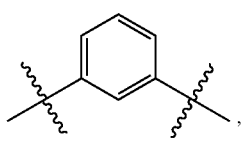

PP)

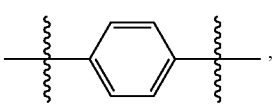

PY)

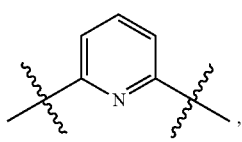

ON)

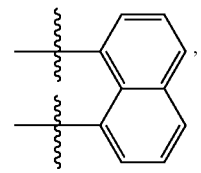

MN)

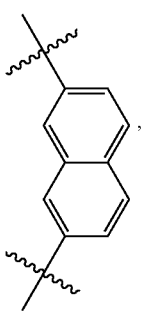

PN)

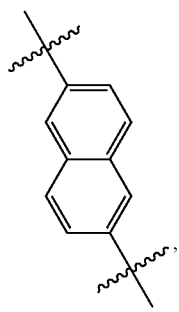

OBP)

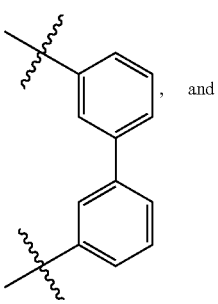

MBP)

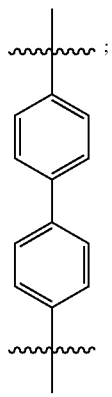

, and

PBP)

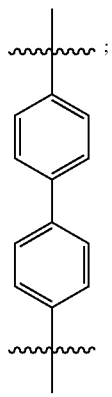

;

X₁ is selected from C, D, G, T, V and W,
X₂ is selected from C, C, F, H, L, N, W, and Y,
X₃ is selected from A, D, N, and W,
X₄ is selected from A, I, S and T,
X₅ is selected from A, C, C, F, H, and T,
X₆ is selected from C, C, F, H, and W,
X₇ is selected from A, D, E, H, I, and T,
X₈ is selected from A, F, I, L, M, R, V, W, and Y,
X₉ is selected from A, F, H, N, and W,
X₁₀ is selected from A, C, C, D, H, R, W, and Y, and
X₁₁ is selected from D, E, and V;

$X_1$-$X_{11}$ are all in the L configuration, except for C which is in the D configuration;

m is 0 or 1, and n is 0 or 1;

or a pharmaceutically acceptable salt thereof.

In some embodiments, $R_1$ is

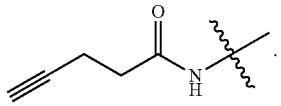 [SMILES: *NC(=O)CCC#C]

In other embodiments, $R_1$ is

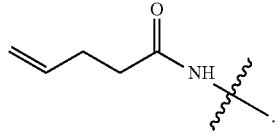 [SMILES: *NC(=O)CCC=C]

In some embodiments, $R_1$ is $H_2N$—.

In some embodiments, Z is

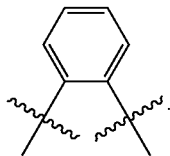 [SMILES: *c1ccccc1*]

In some embodiments, Z is

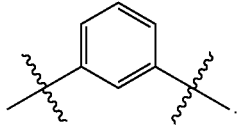 [SMILES: *c1cccc(*)c1]

In some embodiments, Z is

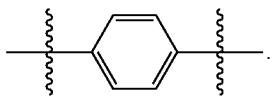

In other embodiments, Z is

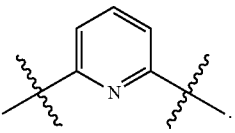 [SMILES: *c1cccc(*)n1]

In some embodiments, $X_2$ is C and $X_6$ is C. In some embodiments, $X_2$ is C and $X_6$ is C. In other embodiments, $X_2$ is C and $X_5$ is C. In some embodiments, $X_1$-$X_{10}$ is VCNATCHIWH (SEQ ID NO: 1), and m is 1. In some embodiments, $X_1$-$X_{10}$ is VCNATCHIWH (SEQ ID NO: 2), and m is 1. In some embodiments, $X_1$-$X_{10}$ is VCNATCHIWH (SEQ ID NO: 9), and m is 1. In some embodiments, $X_1$-$X_{10}$ is VCNATCHIWR (SEQ ID NO: 3), and m is 1. In some embodiments, $X_1$-$X_{10}$ is VWNATCHIWC (SEQ ID NO: 4), and m is 1. In some embodiments, $X_1$-$X_{10}$ is VWNATFHIWHD (SEQ ID NO: 5), m is 1 and n is 1. In some embodiments, $X_1$-$X_{10}$ is VWNATCHIWC (SEQ ID NO: 11), and m is 1.

In some embodiments, the compound is Formula I. In some embodiments, $R_1$ is A and Z is selected from MP and OP. In some embodiments, $R_1$ is $H_2N$ and Z is selected from MP. In other embodiments, $R_1$ is MeC(O) and Z is selected from MP. In still other embodiments, $R_1$ is c(FΦRRRRE) (SEQ ID NO: 14) and Z is selected from MP.

In some embodiments, the compound is Formula II. In some embodiments, $R_1$ is A and Z is selected from PP, MP and OP. In some embodiments, Z is OP.

In other embodiments, the compound is Formula IIIa. In some embodiments, $R_1$ is A. In some embodiments, $R_1$ is $H_2N$. In other embodiments, $R_1$ is c(FΦRRRRE) (SEQ ID NO: 14). In some embodiments, the compound is Formula IIIb. In some embodiments, $R_1$ is A. In some embodiments, the compound is Formula IIIc. In some embodiments, $R_1$ is C.

Disclosed herein are compounds, and pharmaceutically acceptable salts thereof, that include those of Formula I, II, IIIa, and IIIb, such as:

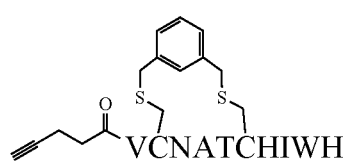

(DD6-m) (SEQ ID NO: 1)

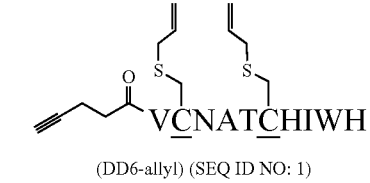

(DD6-allyl) (SEQ ID NO: 1)

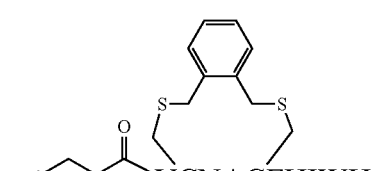

(DD5-o) (SEQ ID NO: 6)

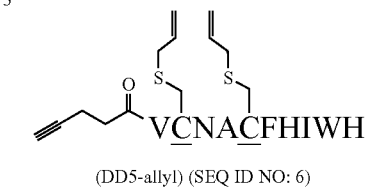

(DD5-allyl) (SEQ ID NO: 6)

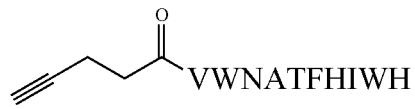
(pa-10mer) (SEQ ID NO: 7)
(pa-11mer) (SEQ ID NO: 5)
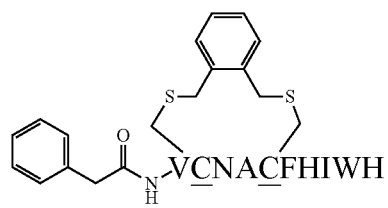
(phenyl-DD5-o) (SEQ ID NO: 6)
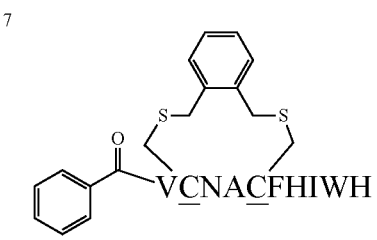
(benzo-DD5-o) (SEQ ID NO: 6)
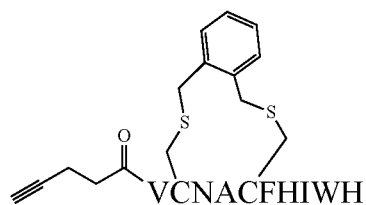
(LL5-o) (SEQ ID NO: 95)
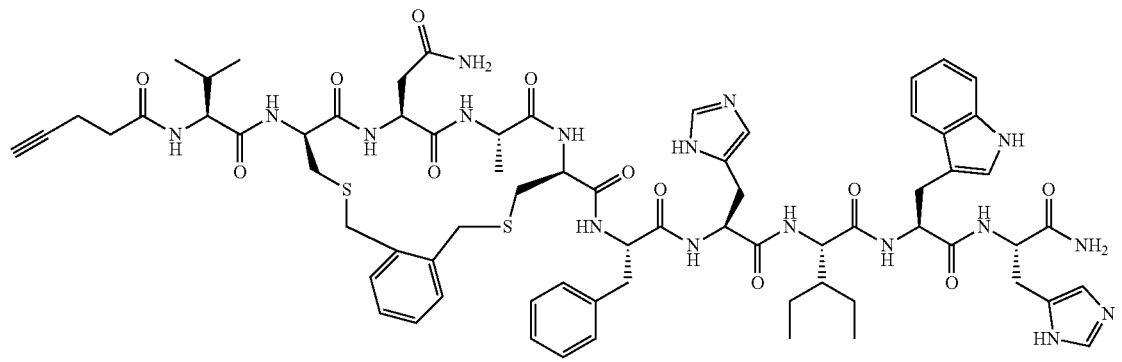
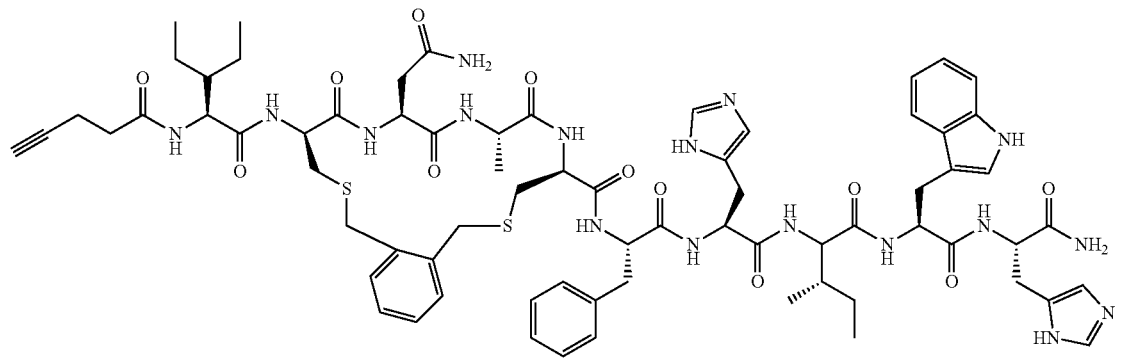

Compounds of Tables 1 and 12 are also exemplary embodiments of the present disclosure.

Disclosed herein, in certain embodiments, are compounds of Formulae IV and V:

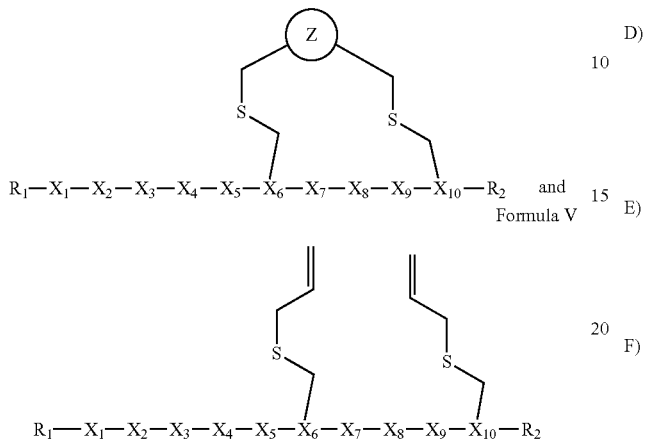

Formula IV

Formula V or a pharmaceutically salt thereof, where variables $R_1$, $R_2$ and $X_1$-$X_{10}$ are as described above.

In certain embodiments, disclosed herein are modified peptides, or pharmaceutically acceptable salt thereof, comprising a linker of formula VI covalently bonded at two amino acids (e.g., at the alpha-carbon), Xa and Xb of formula VII:

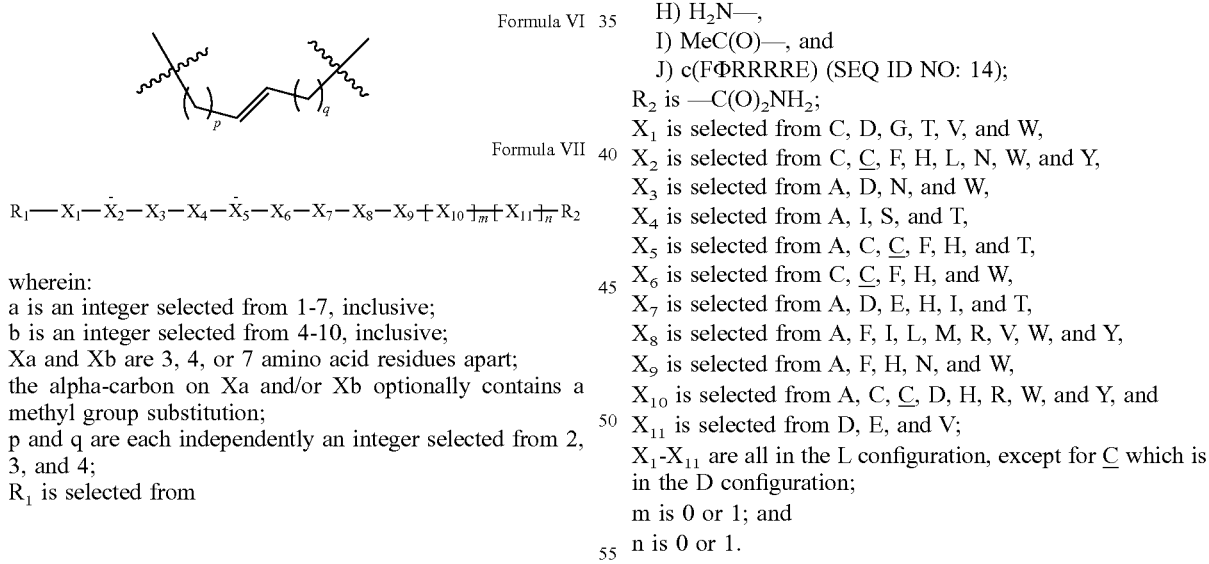

Formula VI

Formula VII wherein:
a is an integer selected from 1-7, inclusive;
b is an integer selected from 4-10, inclusive;
Xa and Xb are 3, 4, or 7 amino acid residues apart;
the alpha-carbon on Xa and/or Xb optionally contains a methyl group substitution;
p and q are each independently an integer selected from 2, 3, and 4;
$R_1$ is selected from

A)

B)

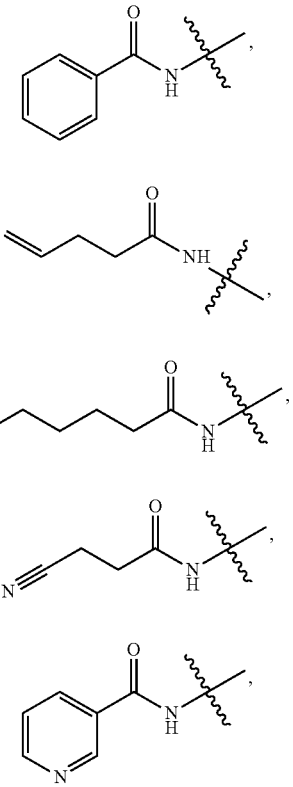

C)

D)

E)

F)

G)

H) $H_2N$—,
I) MeC(O)—, and
J) c(FΦRRRRE) (SEQ ID NO: 14);
$R_2$ is —$C(O)_2NH_2$;
$X_1$ is selected from C, D, G, T, V, and W,
$X_2$ is selected from C, C̲, F, H, L, N, W, and Y,
$X_3$ is selected from A, D, N, and W,
$X_4$ is selected from A, I, S, and T,
$X_5$ is selected from A, C, C̲, F, H, and T,
$X_6$ is selected from C, C̲, F, H, and W,
$X_7$ is selected from A, D, E, H, I, and T,
$X_8$ is selected from A, F, I, L, M, R, V, W, and Y,
$X_9$ is selected from A, F, H, N, and W,
$X_{10}$ is selected from A, C, C̲, D, H, R, W, and Y, and
$X_{11}$ is selected from D, E, and V;
$X_1$-$X_{11}$ are all in the L configuration, except for C̲ which is in the D configuration;
m is 0 or 1; and
n is 0 or 1.

As described herein below, the autophagy activity of cyclic peptides is assayed using routine methods known in the art, including but not limited to LC3 or p62/actin immunoblots, cell based quantitation of LC3-GFP puncta as measured, or by any other method known in the art.

Compounds 1, 2, and 3 induced autophagy at 50-100 µM. Most often, the 10-mer peptide sequences, such as those of Compound, showed greater activity compared to peptide that were truncated at $X_1$ or $X_{10}$. The position of the dithiol linker at $X_2$ and $X_6$ in Formula I and $X_2$ and $X_5$ in Formula II both provided useful cyclic peptides for inducing autophagy.

Small-Molecule Helix Mimics

Based on the helical confirmation of DD5-o, small-molecule helix mimics can also be designed, such as those disclosed in Okuyama et al., *Nature Methods* 4, 153-159 (2007); Whitby and Boger, *Acc Chem Res* 2012, 45, 1698; Arkin et al., *Chemistry & Biology* 2014, 21(9): 1102-1114; Lanning and Fletcher, *Biology* 2015, 4, 540-555; Hoggard et al., *J. Am. Chem. Soc.,* 2015, 137 (38), pp 12249-12260; Wang et al., RSC Adv., 2016, 6, 61599; and Groβ et al., Front. Bioeng. Biotechnol., 2016, dx.doi.org/10.3389/fbioe.2015.00211; all of which are incorporated herein by reference in their entirety.

Pharmaceutical Compositions

Cyclic peptides disclosed herein are cell penetrating and can be used to induce autophagy in a cell in need thereof (e.g., a cell infected with a bacteria or virus). The compositions disclosed herein (e.g., cyclic peptides) are useful for treating a disease or condition having impaired autophagy, including but not limited to neurodegenerative disorders, cancers, muscular diseases, inflammatory bowel disease, autoimmune and/or inflammatory disorders, infectious diseases (e.g., infection with intracellular pathogens such as virus or bacteria), metabolic disorders, innate and adaptive immune disorders, aging, hepatic insulin resistance/diabetes, lysosomal storage disorders, muscular dystrophy, and cystic fibrosis. The compositions can be administered in a pharmaceutically acceptable excipient, such as water, saline, aqueous dextrose, glycerol, or ethanol. The compositions can also contain other medicinal agents, pharmaceutical agents, adjuvants, carriers, and auxiliary substances such as wetting or emulsifying agents, and pH buffering agents. Standard texts, such as Remington: The Science and Practice of Pharmacy, 17th edition, Mack Publishing Company, incorporated herein by reference, can be consulted to prepare suitable compositions and formulations for administration, without undue experimentation. Suitable dosages can also be based upon the text and documents cited herein. A determination of the appropriate dosages is within the skill of one in the art given the parameters herein.

As a rule, the dosage for in vivo therapeutics or diagnostics will vary. Several factors are typically taken into account when determining an appropriate dosage. These factors include age, sex and weight of the patient, the condition being treated, the severity of the condition and the form of the compound being administered.

The dosage of the cyclic peptide compositions can vary from about 0.01 mg/m$^2$ to about 500 mg/m$^2$, such as about 0.1 mg/m$^2$ to about 200 mg/m$^2$, further such as about 0.1 mg/m$^2$ to about 10 mg/m$^2$. Alternatively, the dosages of the cyclic peptide compositions can vary from about 0.01 mg/kg per day to about 1000 mg/kg per day. It is expected that doses ranging from about 50 to about 2000 mg/kg will be suitable. In various embodiments, a dosage ranging from about 0.5 to about 100 mg/kg of body weight is useful; or any dosage range in which the low end of the range is any amount between 0.1 mg/kg/day and 90 mg/kg/day and the upper end of the range is any amount between 1 mg/kg/day and 100 mg/kg/day (e.g., 0.5 mg/kg/day and 5 mg/kg/day, 25 mg/kg/day and 75 mg/kg/day).

Administrations can be conducted infrequently, or on a regular daily or weekly basis until a desired, measurable parameter is detected, such as diminution of disease symptoms. Administration can then be diminished, such as to a biweekly or monthly basis, as appropriate.

Compositions disclosed herein are administered by a mode appropriate for the form of composition. Available routes of administration include subcutaneous, intramuscular, intraperitoneal, intradermal, oral, intranasal, intrapulmonary (i.e., by aerosol), intravenously, intramuscularly, subcutaneously, intracavity, intrathecally or transdermally, alone or in combination with other agents.

Compositions for oral, intranasal, or topical administration can be supplied in solid, semi-solid or liquid forms, including tablets, capsules, powders, liquids, and suspensions. Compositions for injection can be supplied as liquid solutions or suspensions, as emulsions, or as solid forms suitable for dissolution or suspension in liquid prior to injection. For administration via the respiratory tract, a suitable composition is one that provides a solid, powder, or liquid aerosol when used with an appropriate aerosolizer device. Although not required, compositions can be supplied in unit dosage form suitable for administration of a precise amount. Also contemplated herein are slow release or sustained release forms, whereby a relatively consistent level of the active compound are provided over an extended period.

Another method of administration is intralesionally, for instance by direct injection directly into a site in need of autophagy. Alternatively, the cyclic peptide or related compound is administered systemically.

Other delivery systems can include time release, delayed release or sustained release delivery systems. Such systems can avoid repeated administrations of disclosed compositions, increasing convenience to the subject and the physician. Many types of release delivery systems are available and known to those of ordinary skill in the art. They include polymer base systems such as polylactides (U.S. Pat. No. 3,773,919; European Patent No. 58,481), poly(lactide-glycolide), copolyoxalates, polycaprolactones, polyesteramides, polyorthoesters, polyhydroxybutyric acids, such as poly-D-(−)-3-hydroxybutyric acid (European Patent No. 133, 988), copolymers of L-glutamic acid and gamma-ethyl-L-glutamate (Sidman, K. R. et al., Biopolymers 22: 547-556), poly (2-hydroxyethyl methacrylate) or ethylene vinyl acetate (Langer, R. et al., J. Biomed. Mater. Res. 15:267-277; Langer, R. Chem. Tech. 12:98-105), and polyanhydrides.

Other examples of sustained-release compositions include semi-permeable polymer matrices in the form of shaped articles, e.g., films, or microcapsules. Delivery systems also include non-polymer systems that are: lipids including sterols such as cholesterol, cholesterol esters and fatty acids or neutral fats such as mono- di- and tri-glycerides; hydrogel release systems such as biologically-derived bioresorbable hydrogel (i.e., chitin hydrogels or chitosan hydrogels); sylastic systems; peptide based systems; wax coatings; compressed tablets using conventional binders and excipients; partially fused implants; and the like. Specific examples include, but are not limited to: (a) erosional systems in which the agent is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832, 253, and 3,854,480.

Analogs

Analogs can differ from the cyclic peptides provided herein by alterations in primary sequence. Amino acids and analogs are well known in the art. Amino acids may be referred to herein by either their commonly known three letter symbols or by the one-letter symbols recommended by the IUPAC-IUB Biochemical Nomenclature Commission. One substitution is to change the absolute configuration of the amino acid, from L to D or D to L. Amino acids include naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, for example, hydroxyproline, gamma-carboxyglutamate, O-phosphoserine, and phosphothreonine. Other analogs can have a serine amino acid substituted for another thiol containing amino acid, such as homocysteine and penicillamine, as shown in FIG. 3. These analogs can be in the D or L configuration. An amino acid analog is a compound that has the same basic chemical structure as a naturally occurring amino acid, i.e., a carbon that is bound to a hydrogen, a carboxyl group, an amino group, and an R group (e.g., homocysteine, penicillamine, homoserine, norleucine, methionine sulfoxide, methionine methyl sulfonium), but that contains some alteration not found in a naturally occurring amino acid (e.g., a modified side chain); the term "amino acid mimetic" refers to chemical compounds that have a structure that is different from the general chemical structure of an amino acid, but that function in a manner similar to a naturally occurring amino acid. Amino acid analogs may have modified R groups (for example, norleucine) or modified peptide backbones, but retain the same basic chemical structure as a naturally occurring amino acid. In one embodiment, an amino acid analog is a D-amino acid, a ß-amino acid, or an N-methyl amino acid.

Chemical modifications include, but are not limited to, substituting alternative R groups and varying the degree of saturation at specific carbon atoms of a reference peptide. Such cyclic peptide analogs are relatively resistant to in vivo degradation, resulting in a more prolonged therapeutic effect upon administration. Assays for measuring functional activity include, but are not limited to, those described in the Examples below.

In some embodiments, the cyclic peptides contain a chemical tag that aids in isolation and/or identification. Such tags are well known in the art, such as biotin and fluorescent tags such as fluorescein and rhodamine. Peptides substituted with an alkyne can be reacted with azido-substituted tags to provide a triazole linker via "click chemistry". The same triazole linker can be obtained with an azido substituted peptide and alkynyl-substituted tag.

Also included are methods where the peptides contain an affinity tag. An "affinity tag" is any moiety used for the purification of a protein to which it is fixed. Virtually any affinity tag known in the art may be used in these methods, including, but not limited to, calmodulin-binding peptide (CBP), glutathione-S-transferase (GST), 6×His (SEQ ID NO: 15), Maltose Binding Protein (MBP), Green Fluorescent Protein (GFP), biotin, Strep II, and FLAG. A "detectable amino acid sequence" is a composition that when linked with the protein molecule of interest renders the latter detectable, via any means, including spectroscopic, photochemical (e.g., luciferase, GFP), biochemical, immunochemical, or chemical means. For example, useful labels include radioactive isotopes, magnetic beads, metallic beads, colloidal particles, fluorescent dyes, electron-dense reagents, enzymes (e.g., horseradish peroxidase, alkaline phosphatase), biotin, digoxigenin, or haptens.

In some embodiments, the linker can be any chemical group that is covalently bonded to two different amino acids in the peptide. The linker could be an alkene (as produced by ring-closing metathesis described in Walensky and Bird, *J. Med. Chem.*, 2014, 57 (15), pp 6275-6288 and Walensky et al., *Science* 305(56891:1466-1470, both incorporated herein by reference in their entirety), alkane (as produced by hydrogenation of an alkene linker), a benzyl thioether (as describe herein), an alkyl thioether (Wang and Chou, Angew. Chem. Int. Ed., 2015, 54, 10931-10934, incorporated herein by reference in its entirety), a disulfide bond, a lactam (as illustrated in Quartararo, Wu and Kritzer, ChemBioChem 13, 1490-1496 (2012), incorporated herein by reference in its entirety), a lactone, a triazole (as produced by the well-known "click" reaction, described in, e.g., Kolb et al., *Angew. Chem. Int. Ed. Engl.* 40 (11): 2004-2021 and Rostovtsev et al., *Angew. Chem. Int. Ed. Engl.* 41 (14): 2596-9, both incorporated herein by reference in their entirety), or any other suitable chemical group known to those skilled in the relevant art.

For example, a helix-stabilizing linker that is covalently bonded to two different amino acids in the peptide can be used to stabilize alpha-helical structure. The linker can be an alkene having formula VI below, wherein p and q are each an integer selected from 2, 3, and 4. The alkene linker can be produced by ring-closing metathesis described in Walensky and Bird, *J. Med. Chem.*, 2014, 57 (15), pp 6275-6288 and Walensky et al., *Science* 305(5689):1466-1470. In this case, the peptide can have an alkene-containing linker between amino acids Xa (a is an integer selected from 1-7, inclusive) and Xb (b is an integer selected from 4-10, inclusive), wherein Xa and Xb are 3, 4, or 7 amino acid residues apart such that distance between Xa and Xb and the length of the linker permit formation of a stable helix. For each amino acid that is used to form the alkene-containing linker, one can independently vary the side-chain length, the presence or absence of a methyl group on the backbone alpha-carbon, and the stereochemistry of the alpha-carbon, in order to produce the optimal helical geometry for target binding.

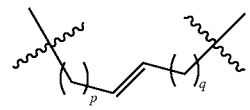

Formula VI

In some embodiments, formula VI linker can be used to staple a peptide having the following sequence, wherein variables m, n, $R_1$, $R_2$ and $X_1$-$X_{10}$ are as described above:

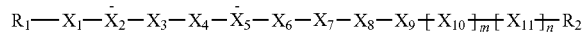

Exemplary stapled peptides having alkene helix-stabilizing linker are shown below, as compared to DD5-o.

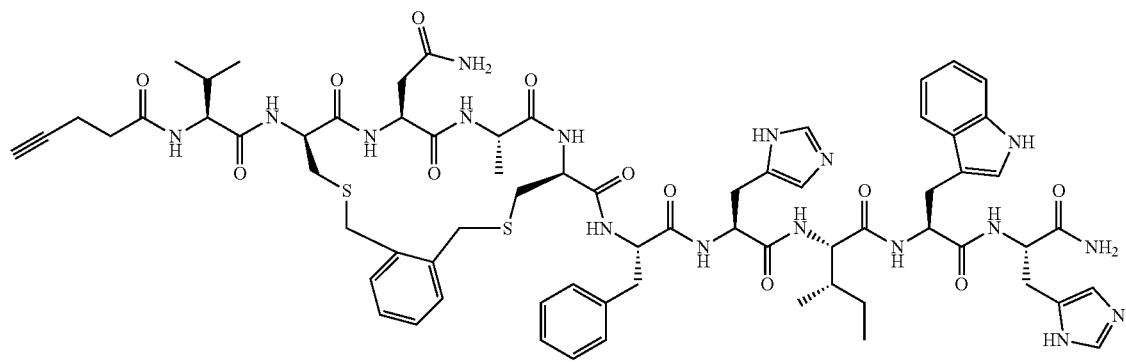
DD5-o
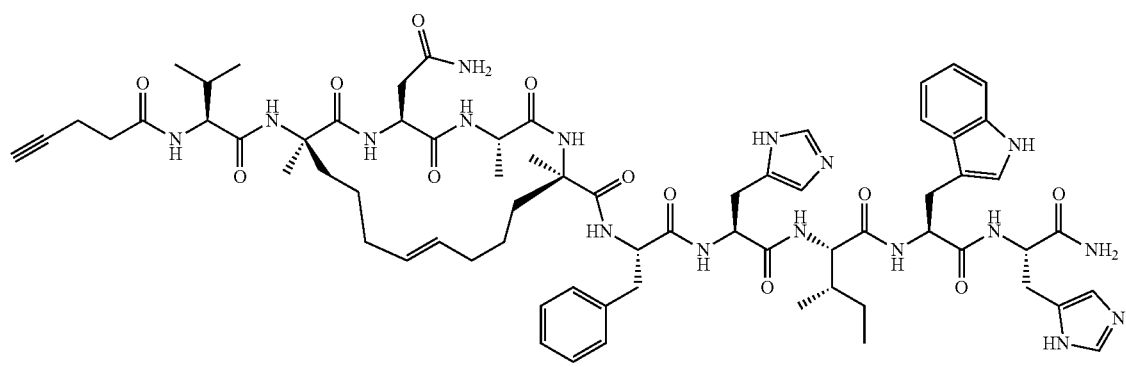
Example of an all-hydrocarbon
stapled analog, stapled at positions 2 and 5
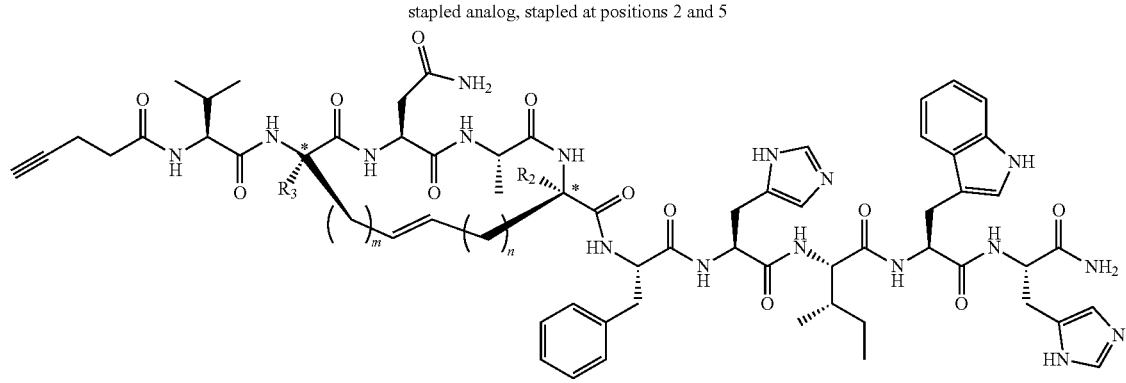
One general form of all-hydrocarbon
stapled analogs, stapled at positions 2 and 5
$R_1$ = (CH$_3$, H): $R_2$ = (CH$_3$, H): m = (2,3,4); n = (2,3,4): * denotes positions where stereochemistry could be altered to be (R) or (S)
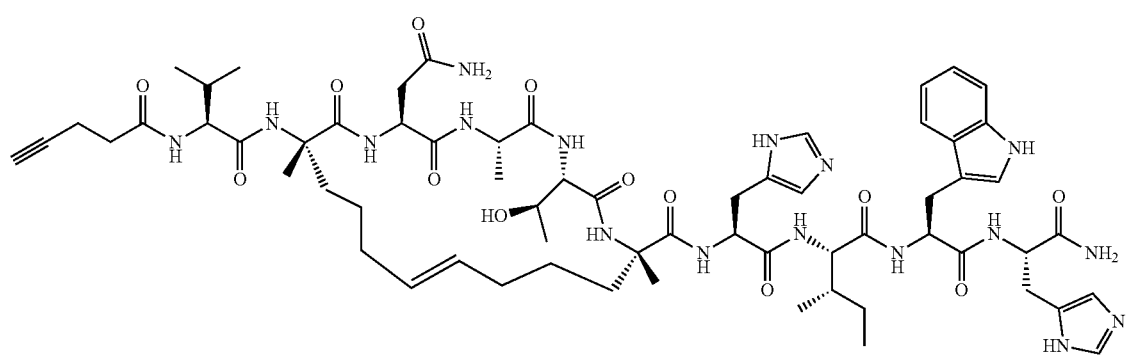
Example of an all-hydrocarbon
stapled analog, stapled at positions 2 and 6

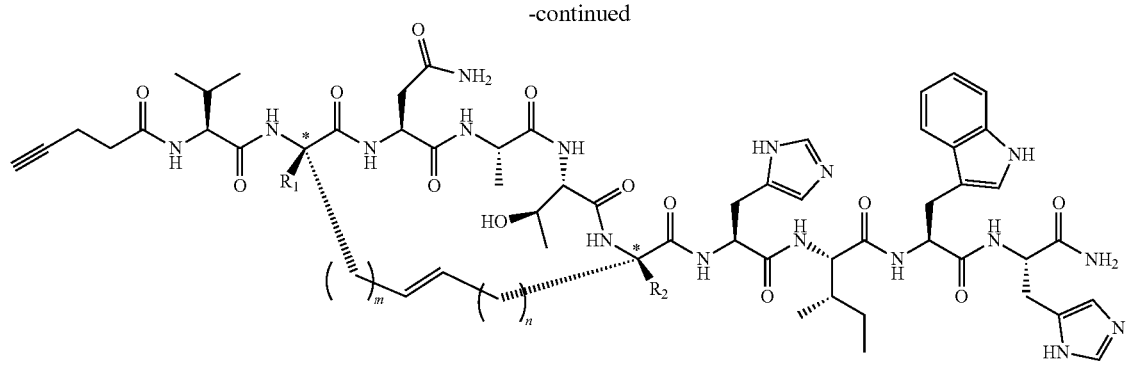

One general form of all-hydrocarbon
stapled analogs, stapled at positions 2 and 6

$R_1$ = (CH$_3$, H): $R_2$ = (CH$_3$, H): m = (2,3,4); n = (2,3,4): * denotes positions where stereochemistry could be altered to be (R) or (S)

The above peptides are examples only. It should be noted that the linker can be stapled at, for example, positions 1 and 4, 1 and 5, 3 and 6, 3 and 7, 4 and 7, 4 and 8, 5 and 8, 5 and 9, 6 and 9, 6 and 10, and 7 and 10.

Therapy

Cyclic peptides disclosed herein are cell penetrating, and provide for the induction of autophagy in a cell contacted with the peptide. Autophagy functions in metazoans in cellular and tissue homeostasis, physiology, development, and protection against disease, and abnormalities in autophagy may contribute to many different pathophysiological conditions. Thus, strategies that augment autophagy may prevent or treat human disease including, but not limited to, neurodegeneration, steatohepatitis, and cancer. Induction of autophagy is also known to be useful to reduce the replication of several pathogens, including but not limited to viruses and bacteria.

Accordingly, provided herein are methods of enhancing or inducing autophagy in persons in need of enhanced autophagy. Also provided herein are methods of treating diseases and pathologies where the upregulation of autophagy is therapeutically beneficial, including neurodegenerative disorders, cancers, muscular diseases, inflammatory bowel disease, autoimmune and/or inflammatory disorders, infectious diseases (e.g., infection with intracellular pathogens such as virus or bacteria), metabolic disorders, innate and adaptive immune disorders, aging, hepatic insulin resistance/diabetes, lysosomal storage disorders, muscular dystrophy, and cystic fibrosis. In some embodiments, the disease can be infections with intracellular pathogens, neurodegenerative diseases (such as Alzheimer's, Parkinson's, and Huntington's disease), cancers, cardiomyopathy, and aging. For example, one method of treating bacterial or viral infections or symptoms thereof, neurodegenerative diseases, cancers, cardiomyopathy, steatohepatitis, and/or aging can comprise administering a therapeutically effective amount of a pharmaceutical composition comprising a compound of the formulae disclosed herein to a subject in need thereof (e.g., a mammal such as a human).

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

Therapeutic methods (which include prophylactic treatment) in general comprise administration of a therapeutically effective amount of the compounds herein, such as a compound of the formulae herein to a subject (e.g., animal, human) in need thereof, including a mammal, such as a human. Such treatment will be suitably administered to subjects, such as humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which a need for the induction of autophagy may be implicated.

One embodiment provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with neurodegenerative disorders, cancers, muscular diseases, inflammatory bowel disease, autoimmune and/or inflammatory disorders, infectious diseases (e.g., infection with intracellular pathogens such as virus or bacteria), metabolic disorders, innate and adaptive immune disorders, aging, hepatic insulin resistance/diabetes, lysosomal storage disorders, muscular dystrophy, and cystic fibrosis, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In some embodiments, a second level of Marker in the subject is determined at a time point later than the determination of the first level, and the two levels are compared to monitor the course of disease or the efficacy of the therapy. In certain embodiments, a pre-treatment level of Marker in the subject is determined prior to beginning treatment; this pre-treatment level of Marker can then be compared to the level of Marker in the subject after the treatment commences, to determine the efficacy of the treatment.

The practice of the presently disclosed molecules, compounds, and methods employs, unless otherwise indicated, conventional techniques of molecular biology (including recombinant techniques), microbiology, cell biology, biochemistry, immunology and chemistry, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the chimeric small molecules as provided herein, and, as such, may be considered in making and practicing the disclosed embodiments. The following examples are put forth so as to provide those of ordinary skill in the art with a description of how to make and use the disclosed assay, screening, and therapeutic methods, and are not intended to limit the scope of the recited claims.

From the foregoing description, it will be apparent that variations and modifications may be made to the procedures described herein to adopt it to various usages and conditions. Such embodiments are also within the scope of the following claims.

All patents and publications mentioned in this specification are herein incorporated by reference to the same extent as if each independent patent and publication was specifically and individually indicated to be incorporated by reference.

EXAMPLES

Example 1: Linear Peptide Synthesis

The synthesis of Tat-containing linear peptides was performed as described in Shoji-Kawata 2013:

L-amino acid peptides were synthesized by the University of Texas Southwestern Medical Center (UTSW) Protein Chemistry Technology Core and purified to 0.95% by HPLC (confirmed by mass spectrometry). The Tat-beclin 1 peptide sequence, YGRKKRRQRRRGGTNVFNATFEIWHDGEFGT (SEQ ID NO: 8), consisted of 11 amino acids from the Tat PTD at the N terminus, a GG linker to increase flexibility, and at the C terminus, 18 amino acids derived from beclin 1 267-284 containing three substitutions, including H275E, S279D, Q281E. Wild-type Tat-beclin 1 peptide consisted of the Tat PTD, a GG linker, and 18 amino acids derived from the natural beclin 1 sequence (267-284) (YGRKKRRQRRRGGTNVFNATFHIWHSGQFGT; SEQ ID NO: 25). Control peptide, Tatscrambled, consisted of the Tat protein transduction domain, a GG linker, and a scrambled version of the C-terminal 18 amino acids from Tat-beclin 1 (YGRKKRRQRRRGGVGNDFFINHETTGFATEW; SEQ ID NO: 26). For experiments comparing Tat-beclin 1 and Tat-scrambled, peptides were dissolved in PBS(2), whereas in the experiment comparing Tat-beclin 1 and wild-type Tat-beclin 1, peptides were dissolved in H2O. Peptides were stored at 280 uC. For peptide treatment, cells were washed with PBS(2) and treated with peptides (10-50 mM, 1-4 h) dissolved in OPTI-MEM (Gibco) acidified with 0.15% (v/v) 6N HCl. For treatment of primary human MDMs, cells were washed with PBS and pre-treated with peptides (0.5-5 mM, 24 h) in 500 ml macrophage-SFM (serum-free media) (Gibco) before infection with HIV-1. D-amino acid peptides were synthesized at the HHMI Mass Spectrometry Laboratory at UC-Berkeley. The retro-inverso Tat-beclin 1 D-amino acid sequence was RRRQRRKKRGYGGTGFEGDHWIEFTANFVNT (SEQ ID NO: 27). Peptides were synthesized by solid-phase methodology on Wang resin of 0.44 meq g21 substitution using an ABI 431A synthesizer. Appropriate N-FMOC amino acid derivatives were coupled via dicyclohexylcarbodiimide activation in dichloromethane/N-methylpyrrolidone using user-devised extended activation, coupling and piperidine deprotection cycles. Dried resin-peptide was deprotected in reagent K 4 h at room temperature. Peptide was extracted with warm acetonitrile/water, lyophilized, and purified by RPLC. Crude peptide purity was roughly 75%; after purification, 95%. D-amino acid peptides were dissolved in H$_2$O and stored at 280 uC until use. Peptide purity was assessed by FTICR mass spectrometry.

Example 2: Synthesis of Linear Peptides without Tat

Standard fluorenylmethoxycarbonyl (Fmoc) solid-phase peptide synthesis (SPPS) was used to synthesize the linear precursor peptides. For an amidated C-terminus we used Rink Amide Resin (100-200 mesh) with a loading of 0.3-0.6 mmol/g. In order to produce a panel of cross-linked peptides, we began with the synthesis of one parent linear peptide at a scale of 50-100 μmoles. Peptides were synthesized by hand or using an automated synthesizer. After synthesizing the linear sequence, the N-terminus was capped or left as a free amine, and the peptide was cleaved off the resin. The peptide was precipitated using cold ether in order to separate it from protecting groups and cleavage reagents. The linear peptide was either purified using reverse-phase high performance liquid chromatography (RP-HPLC) or directly used in thiol bis-alkylation reactions. The linear peptide was divided into multiple reaction vessels, and reacted with different linkers in a 50:50 mixture of acetonitrile (CH$_3$CN) and water buffered at pH 8.0. The reaction was typically complete within 1 hour at room temperature. After bis-alkylation, solvents were be concentrated by lyophilizing the reaction and resuspending in a smaller volume of CH3CN/H2O. The reaction mixture was purified by RP-HPLC to obtain the final cyclic product. An abbreviated procedure is provided below:

a. Swell resin in 5-10 mL of DMF for at least 30 min with shaking.
b. Deprotect the resin using 5-10 mL of 20% piperidine in DMF for 2×7 min.
c. Wash the resin with 5-10 mL of DMF, 2×30 sec, DCM 2×30 sec, DMF 2×30 sec. The presence of a free amine can be confirmed using a Kaiser Test.
d. Dissolve 5 equiv. of the Fmoc-AA-OH, 5 equiv. of coupling reagent, 1-[bis(dimethylamino) methylene]-1H-1,2,3-triazolo[4,5-b]pyridinium 3-oxid hexafluorophosphate (HATU) and 5 equiv. of the coupling additive 1-hydroxy-7-azabenzotriazole (HOAt) in 5-10 mL of DMF or NMP. Add to resin and also add 13 equiv. of DIPEA. Shake at room temp for 30 mins. The completion of the reaction can also be checked with a negative Kaiser Test.
e. Wash the resin extensively as in step c.
f. Repeat Fmoc deprotection and coupling steps b-e until the final amino acid has been coupled to the growing peptide chain.
g. After coupling the last amino acid, remove the last Fmoc group as described in step b. Then, if an acetylated N-terminus is desired, cap the resin using 5-10 mL 10% acetic anhydride/10% 2,6-lutidine/80% DMF for 2×10 min h. Wash the resin extensively using DMF and DCM, finishing with a methanol wash. Dry out the resin completely using vacuum or dry nitrogen or argon gas.

i. For global deprotection and cleavage, use a standard cleavage cocktail: 95% trifluoroacetic acid (TFA), 2.5% 1,2-ethanedithiol (EDT), 2.5% H2O, and 1% triisipropylsilane (TIPS). Use a minimal amount to cover the resin, typically 1-2 mL. Allow to deprotect for 3-4 hours depending on the amino acids in the sequence.

j. Chill 40 mL of diethyl ether on dry ice for 15 min.

k. Once the cleavage is complete, filter the cleavage solution to separate it from the resin and add dropwise to chilled ether. The peptide precipitates in the ether and the solution should become opaque.

l. Centrifuge at 3,500 rpm for 10 mins. Decant the ether and wash the pellet with 40 mL of freshly chilled diethyl ether. Centrifuge again at 3,500 rpm for 10 mins.

m. Decant the ether and dry the pellet under dry argon or nitrogen gas.

Example 3: Bis-Alkylation of Linear Peptide Synthesized in Example 2 a. Dissolve the ether-precipitated pellet (or purified linear peptide) in 50:50 $CH_3CN/H_2O$.

b. If the linear peptide has a Tyr or Trp, determine the concentration by UV-vis spectrophotometry using UV absorbance at 280 nm. If the concentration cannot be determined estimated by UV, assume a 100% yield of the overall solid-phase synthesis.

c. Prepare a 1 mM solution of peptide in 50:50 solution of $CH_3CN$ and $H_2O$ buffered with 20 mM ammonium bicarbonate, pH 8.0.

d. Check the pH of the solution before the linker is added. The pH should be about 8.

e. Dissolve 1.5 equiv. of linker in 1-2 mL of $CH_3CN$ and add to the peptide. The reaction is typically complete in under 1 hour. the formation of the product can be monitored using mass spectrometry. For instance, adding the OP, MP or PP linker will result in a cyclic peptide product that is 102 Daltons higher in mass than the linear peptide. For most peptides, the appearance of the product peak by MALDI-TOF coincides with the disappearance of the starting material, and that the mass spectrometry peak for the starting material frequently becomes unobservable after 1 hour.

f. The reaction can be stopped by lowering the pH with HCl or TFA, and can be immediately purified. Freeze the reaction, lyophilize, and re-dissolve in a smaller volume prior to purification.

g. Once the cyclic peptide is purified, it can be stored as lyophilized powder at −20° C. or directly used in assays.

Example 4: Peptide Synthesis and Thioether Stapling

Peptides were synthesized on Rink Amide resin (0.53 mmol/g) using standard Fmoc chemistry. For each coupling 5 eq. of Fmoc-amino acid, 5 eq. of 2-(7-aza-1H-benzotriazole-1-yl)-1,1,3,3-tetramethyluronium hexafluorophosphate (HATU), 5 eq. of 1-hydroxy-7-azabenzotriazole (HOAt), and 13 eq. of diisopropylethylamine (DIPEA) were dissolved in N,N-Dimethylformamide (DMF) and added to the resin. The reaction was allowed to proceed for 30 mins. For the N-terminal caps double coupling was required. For HaloTag-peptides, HaloTag-COOH (kindly obtained from the Chenoweth Lab at University of Pennsylvania) was appended to the N-terminus by reacting 3 eq. with 3 eq. benzotriazol-1-yl-oxytripyrrolidino phosphonium hexafluorophosphate (PyBOP), 3 eq. 1-hydroxybenzotriazole (HOBt), and 6 eq. DIPEA for 1 hour at room temperature. The peptides were globally deprotected and cleaved off the resin by treatment with 94:2.5:2.5:1 (v/v) TFA/ethanedithiol/water/triisipropylsilane for 3 hour. The peptides were triturated in cold diethyl ether and washed two times. The crude pellet was then dissolved in 50:50 acetonitrile/water, and after confirming the identity of the peptide by MALDI-TOF mass spectrometry, was subjected to bis-alkylation conditions as previously shown.[52] All peptides were purified by reserved-phase HPLC on a $C_8$ preparative column. Purity of the final product was confirmed on a $C_{18}$ analytical column.

Figures 1B, 1C:
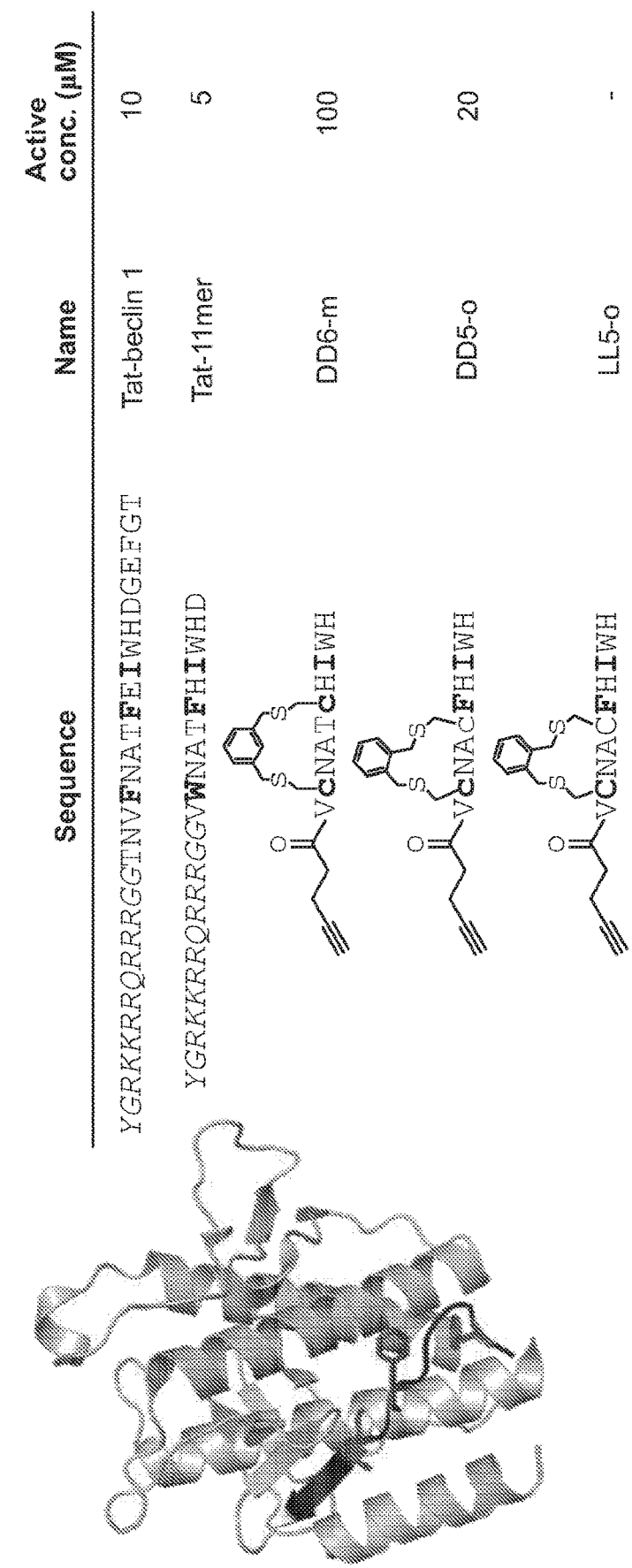
Figures 2, 2A, 2B, 2C:
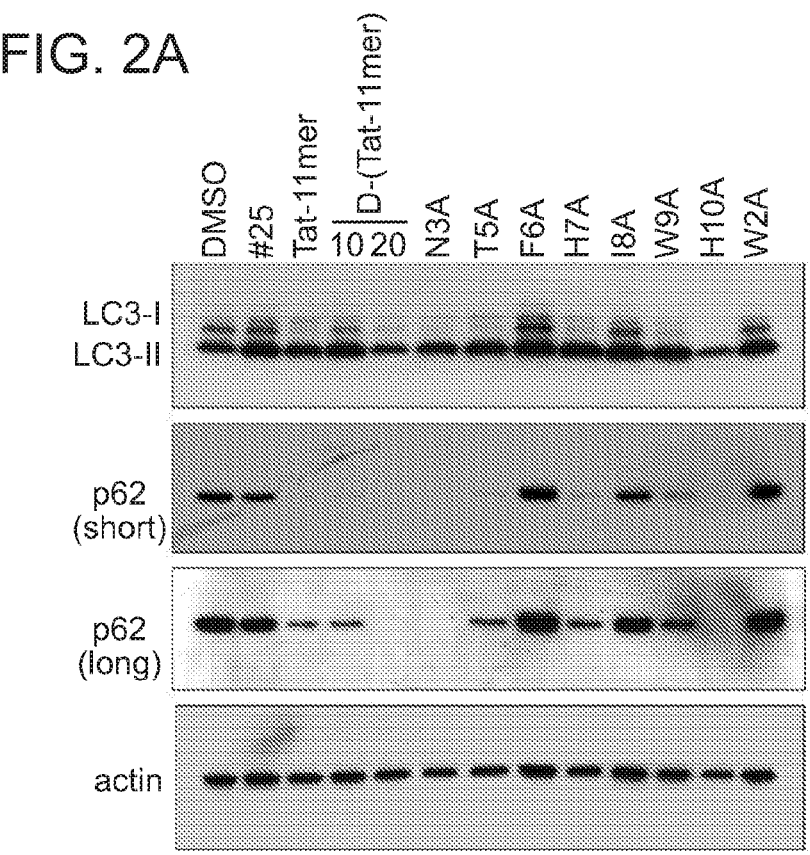
FIG. 2. Identification of key residues for Tat-11mer. 2A. Autophagy induction in HeLa cells for additional peptides, analyzed using p62 and LC3 immunoblots. Two exposures are shown for p62 blots, short and long. Actin is shown as a loading control. Alanine scan peptides for Tat-11mer were tested alongside peptide #25: YGRKKRRQRRR-GG-VFNATFEIWH (SEQ ID NO: 10), and the retro inverso of Tat-11mer, D-(Tat-11mer). All peptides were tested at 10 µM, except for D-(Tat-11mer) tested at 10 and 20 µM. 2B. Sequences of Tat-11mer alanine scan peptides tested in a. (SEQ ID NOs: 63 and 96-103, in order of appearance). 2C. Two key Phe to Ser substitutions tested for Tat-11mer, alongside Tat-11mer and a scrambled version of Tat-11mer, Tat-11scr. All peptides were tested at 10 µM.
Figure 2C:
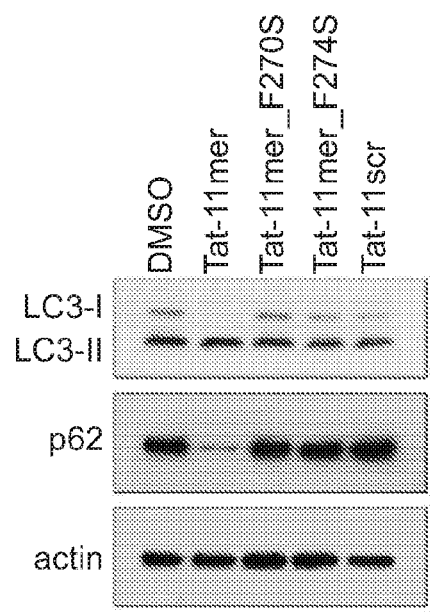

Example 5: Design and Synthesis of Improved Tat-Linked Peptides and Stapled Peptides The autophagy-inducing peptide Tat-Beclin 1 (FIG. 1, *c*) was derived from the sequence of the evolutionarily conserved domain (ECD) of Beclin 1 (FIG. 1, *b*).[10] First, we improved the potency of Tat-Beclin 1 by iteratively designing, synthesizing and testing peptides in p62 degradation and LC3 conversion assays analyzed by Western blot.[44] An alanine scan was used to determine the key residues for activity, and conservative substitutions and truncations revealed the optimal sequence and minimal length required to observe autophagy induction (FIG. 1, *c*). The optimized peptide, called Tat-11mer, consisted of only eleven residues derived from Beclin 1, with a Gly-Gly linker and Tat sequence of the N-terminus. Structure-activity relationships (SAR) for Tat-11mer revealed that the increased potency was due to specific substitutions within the Beclin 1-derived sequence (Phe2 to Trp, and Glu7 to His); the Glu7 to His substitution restores the amino acid at this position in full-length Beclin 1. A direct alanine scan of Tat-11mer revealed that Trp2, Phe6, and Ile8 in the Beclin 1-derived region were absolutely necessary for activity (FIG. 2). This correlates with previous data for full-length Tat-Beclin 1, where altering the residues that correspond to Trp2 and Phe6 completely abolished activity.[10] Tat-11mer is approximately 2- to 4-fold more potent than the previously reported Tat-Beclin 1, with an increase in autophagy observed in cell culture at concentrations as low as 5μM. This is the most potent Beclin 1-derived autophagy-inducing peptide discovered to date.

Figure 4:
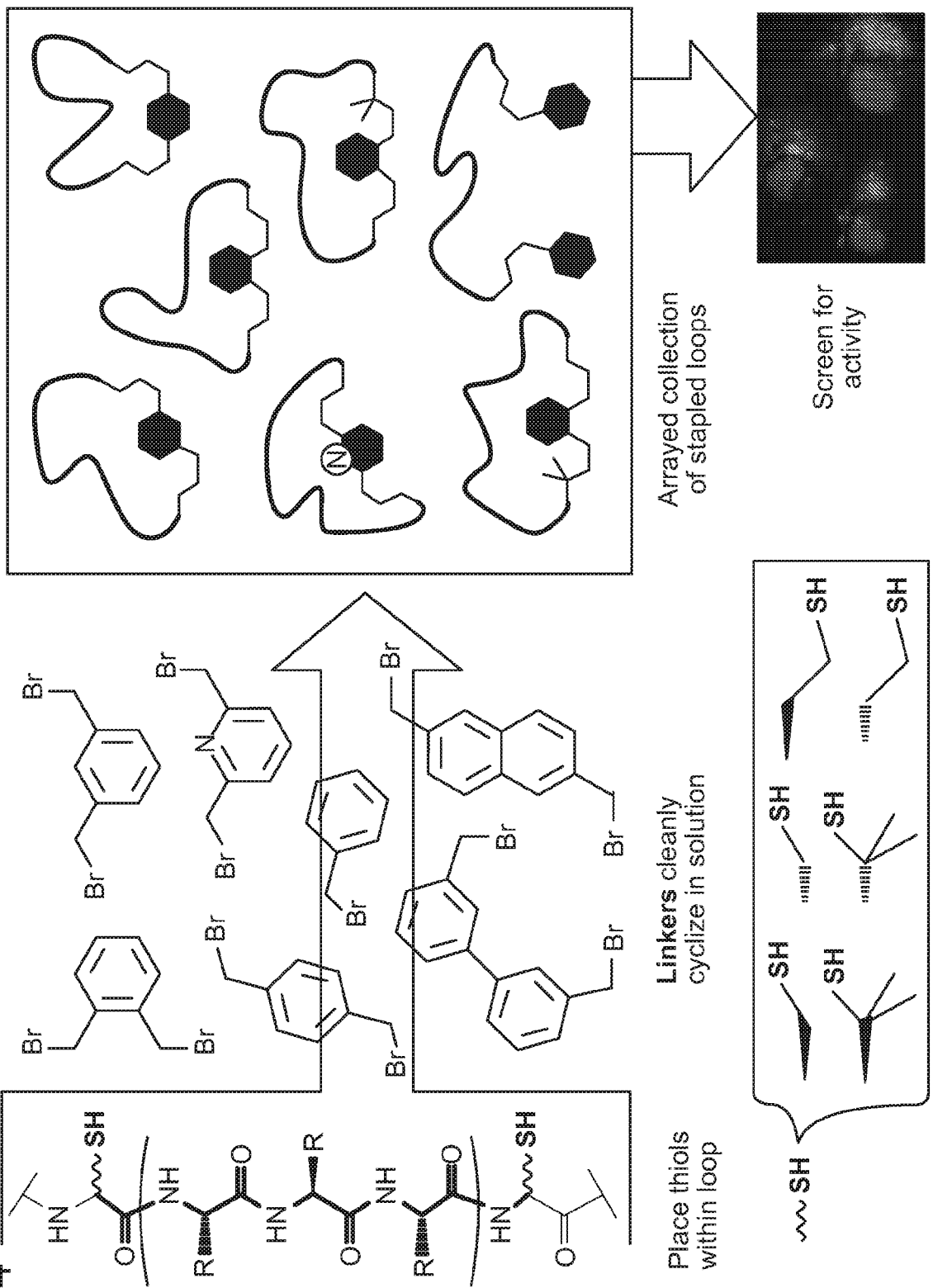
FIG. 4 depicts a general strategy for structure-independent stapling, here applied to producing stapled analogs of Beclin 1-derived sequences and testing them in cell-based autophagy assays. Two thiol-containing amino acids were introduced within the epitope of interest and reacted with a variety of dibromide linkers to yield an array of conformationally diverse peptides, which were then screened for activity.

Once we narrowed down the necessary sequence to just eleven residues, we next sought to render the peptide intrinsically cell-penetrant. Our laboratory and others have shown that conformationally constraining peptides can increase potency, metabolic stability and cell penetration.[45-48] Many successful strategies have employed side-chain-to-side-chain covalent cross-linking, or "stapling." Current stapling approaches include ring-closing olefin metathesis, lactam formation, oxime linkages, and click chemistry,[49] but the low-yielding nature of many macrocyclization reactions can limit the throughput and conformational diversity available to these strategies.[50] Moreover, the Beclin 1-derived sequence had no evidence of defined secondary structure from structural or modeling data, so it was not possible to predict which stapled conformations would yield peptides with increased potency. We therefore devised a structure-independent stapling strategy (FIG. 4). In this approach, we introduced two thiol-containing amino acids within the sequence and used thiol bis-alkylation chemistry to cross-link them.[51] This cross-linking reaction can be performed in solution under mild aqueous conditions and has proven to be very robust, with almost quantitative yields and little formation of dimer or other side products.[52] Its high efficiency and versatility is highlighted by several applications,[53-55] including our recent application to macrocyclization of loop epitopes to produce inhibitors of protein-protein interactions.[56] The location of the staple was varied (FIG. 6) and included locations that cross-linked residues that are proximal to each other in the crystal structure of the ECD of Beclin 1 (FIG. 1, b). For each staple position, all permutations of L- and D-cysteines were tested, along with a variety of different linkers. In this manner, a synthetic library of peptides with varied conformational constraints was produced for testing in cell-based autophagy assays. A unique aspect of this strategy is that it does not presume a specific target structure, which allowed us to search broadly for the stapled conformation that yields the most potent molecule.

Example 6: Stapled Peptides Induce Autophagic Flux In Vitro

Figure 5D:
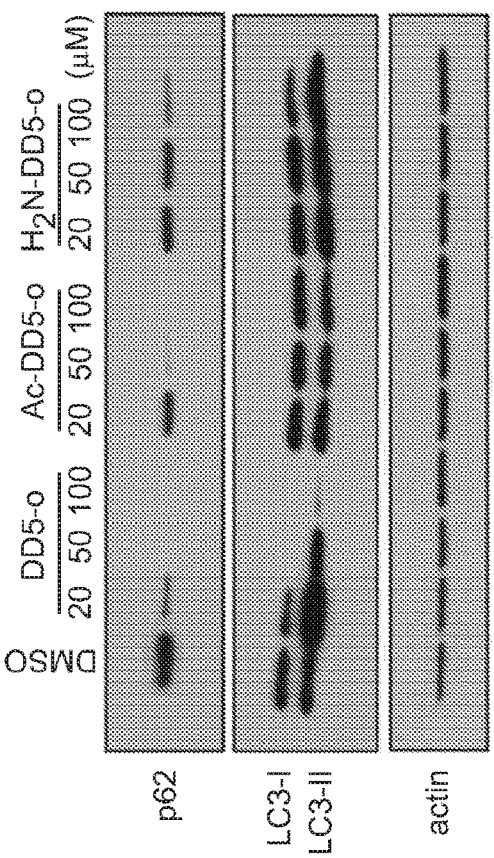
Figure 5E:
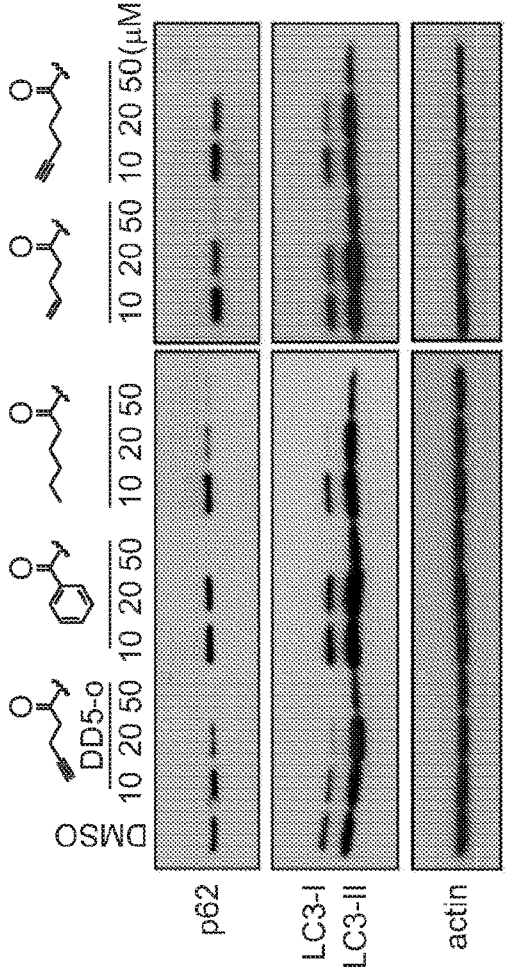
Figure 5F:
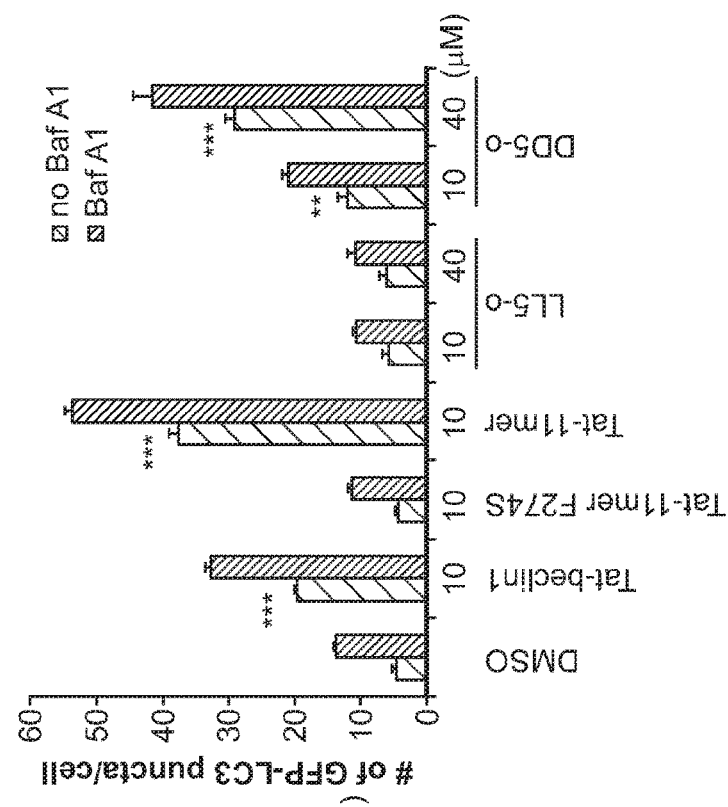

Stapled peptides were tested in phenotypic assays in HeLa cells, using the accepted measurements of p62 degradation and LC3-II conversion to assess autophagy induction.[44] Removing Tat and capping the N-terminus (peptide pa-11mer; sequence in Table 1) produced a peptide that did not increase autophagic activity (FIG. 5, a). Further removing the C-terminal aspartate, which we judged would likely impair cell penetration, produced pa-10mer, which has barely detectable activity. This 10-mer sequence was substituted with various thiol-containing amino acids at various positions, and then cross-linked with various linkers as described above (FIG. 5, a and FIG. 6). Substituting Trp2 and Phe6 with D-cysteines and cross-linking with meta-xylene yielded a peptide with improved activity (peptide DD6-m, which showed strong autophagy induction at 100 µM; see FIG. 7). A significant improvement in activity was observed when the staple was altered from an (i, i+4) spacing to an (i, i+3) spacing by substituting Trp2 and Thr5 with D-cysteines, and cross-linking with ortho-xylene. This peptide, DD5-o, has potent in vitro activity at 20 µM, which is nearly equal in potency to the original, full-length Tat-Beclin 1 (FIG. 5, b).

TABLE 1

Peptide sequences and observed masses following HPLC purification.

| Name | Peptide structure (cap)-Sequence | Linker | Calculated [M + H$^+$] | Observed [M + H$^+$] |
|---|---|---|---|---|
| pa-11mer | (pa)-VWNATFHIWHD (SEQ ID NO: 12) | — | 1504.68 | 1504.04 |
| pa-10mer | (pa)-VWNATFHIWH (SEQ ID NO: 13) | — | 1389.59 | 1388.49 |
| DD5-o | (pa)-VcNAcFHIWH (SEQ ID NO: 70) | ortho-xylene | 1410.68 | 1410.82 |
| DD5-m | (pa)-VcNAcFHIWH (SEQ ID NO: 70) | meta-xylene | 1410.68 | 1411.16 |
| DD5-p | (pa)-VcNAcFHIWH (SEQ ID NO: 70) | para-xylene | 1410.68 | 1410.83 |
| DD5-allyl | (pa)-VcNAcFHIWH (SEQ ID NO: 70) | allyl | 1388.68 | 1388.81 |
| DL5-o | (pa)-VcNACFHIWH (SEQ ID NO: 71) | ortho-xylene | 1410.68 | 1411.34 |
| LD5-o | (pa)-VCNAcFHIWH (SEQ ID NO: 72) | ortho-xylene | 1410.68 | 1411.12 |
| LL5-o | (pa)-VcNAcFHIWH (SEQ ID NO: 70) | ortho-xylene | 1410.68 | 1410.89 |
| DD6-m | (pa)-VcNATcHIWH (SEQ ID NO: 73) | meta-xylene | 1364.41 | 1363.90 |
| Ac-DD5-o | (acetyl)-VcNAcFHIWH (SEQ ID NO: 74) | ortho-xylene | 1326.56 | 1327.60 |
| H$_2$N-DD5-o | (free amine)-VcNAcFHIWH (SEQ ID NO: 75) | ortho-xylene | 1284.52 | 1284.08 |
| His10Ala | (pa)-VcNAcFHIWA (SEQ ID NO: 76) | ortho-xylene | 1345.60 | 1345.24 |

TABLE 1-continued

Peptide sequences and observed masses following HPLC purification.

| Name | (cap)-Sequence | Linker | Calculated [M + H+] | Observed [M + H+] |
|---|---|---|---|---|
| Trp9Ala | (pa)-VcNAcFHIAH (SEQ ID NO: 77) | ortho-xylene | 1296.53 | 1296.27 |
| Ile8Ala | (pa)-VcNAcFHAWH (SEQ ID NO: 78) | ortho-xylene | 1369.59 | 1369.46 |
| His7Ala | (pa)-VcNAcFAIWH (SEQ ID NO: 79) | ortho-xylene | 1345.60 | 1344.72 |
| Phe6Ala | (pa)-VcNAcAHIWH (SEQ ID NO: 80) | ortho-xylene | 1335.57 | 1334.99 |
| Asn3Ala | (pa)-VcAAcFHIWH (SEQ ID NO: 81) | ortho-xylene | 1368.64 | 1368.20 |
| Val1Ala | (pa)-AcNAcFHIWH (SEQ ID NO: 82) | ortho-xylene | 1383.61 | 1383.02 |
| HTag-DD5-o | (HTag)-VcNAcFHIWH (SEQ ID NO: 83) | ortho-xylene | 1636.40 | 1636.52 |
| HTag-DD5-neg | (HTag)-VcNAcFHIWH (SEQ ID NO: 83) | acetic acid | 1650.33 | 1649.41 |
| D6D10-o | (pa)-VWNATcHIWc (SEQ ID NO: 84) | ortho-xylene | 1413.68 | 1411.87 |
| D6D10-m | (pa)-VWNATcHIWc (SEQ ID NO: 84) | meta-xylene | 1413.68 | 1412.99 |
| D6L10-o | (pa)-VWNATcHIWC (SEQ ID NO: 85) | ortho-xylene | 1413.68 | 1413.22 |
| D6L10-m | (pa)-VWNATcHIWC (SEQ ID NO: 85) | meta-xylene | 1413.68 | 1412.41 |
| D6L10-allyl | (pa)-VWNATcHIWC (SEQ ID NO: 85) | allyl | 1391.68 | 1390.97 |
| D6D11-o | (pa)-VWNATFcIWHc (SEQ ID NO: 86) | ortho-xylene | 1560.86 | 1561.57 |
| D6D11-m | (pa)-VWNATFcIWHc (SEQ ID NO: 86) | meta-xylene | 1560.86 | 1562.01 |
| D6D11-allyl | (pa)-VWNATFcIWHc (SEQ ID NO: 86) | allyl | 1538.85 | 1539.10 |
| DD6-o | (pa)-VcNATcHIWH (SEQ ID NO: 73) | ortho-xylene | 1364.61 | 1363.88 |
| DD6-allyl | (pa)-VcNATcHIWH (SEQ ID NO: 73) | allyl | 1342.60 | 1342.72 |
| DD6-nap | (pa)-VcNATcHIWH (SEQ ID NO: 73) | 2,6-naphthlene | 1414.67 | 1415.00 |
| DD6-phe | (pa)-VcNATcHIWH (SEQ ID NO: 73) | 4,4-biphenyl | 1440.71 | 1440.09 |
| DL6-allyl | (pa)-VcNATcHIWH (SEQ ID NO: 73) | allyl | 1342.60 | 1341.93 |
| LD6-allyl | (pa)-VCNATcHIWH (SEQ ID NO: 87) | allyl | 1343.60 | 1342.14 |
| LL6-p | (pa)-VCNATCHIWH (SEQ ID NO: 17) | para-xylene | 1364.61 | 1363.57 |
| LL6-nap | (pa)-VCNATCHIWH (SEQ ID NO: 17) | 2,6-naphthlene | 1414.67 | 1412.51 |

TABLE 1-continued

Peptide sequences and observed masses following HPLC purification.

| Name | Peptide structure (cap)-Sequence | Linker | Calculated [M + H$^+$] | Observed [M + H$^+$] |
|---|---|---|---|---|
| LL6-phe | (pa)-VCNATCHIWH (SEQ ID NO: 17) | ortho-xylene | 1440.71 | 1441.18 |
| nicot-DD5-o | (nicot)-VcNAcFHIWH (SEQ ID NO: 88) | ortho-xylene | 1435.69 | 1436.22 |
| phenyl-DD5-o | (phenyl)-VcNAcFHIWH (SEQ ID NO: 89) | ortho-xylene | 1448.73 | 1449.61 |
| benzo-DD5-o | (benzo)-VcNAcFHIWH (SEQ ID NO: 90) | ortho-xylene | 1434.70 | 1433.77 |
| hexano-DD5-o | (hexano)-VcNAcFHIWH (SEQ ID NO: 91) | ortho-xylene | 1428.74 | 1428.63 |
| hexyno-DD5-o | (hexyno)-VcNAcFHIWH (SEQ ID NO: 92) | ortho-xylene | 1424.71 | 1424.32 |
| cyano-DD5-o | (cyano)-VcNAcFHIWH (SEQ ID NO: 93) | ortho-xylene | 1411.67 | 1411.58 |
| pentene-DD5-o | (pentene)-VcNAcFHIWH (SEQ ID NO: 94) | ortho-xylene | 1412.70 | 1412.59 |

Lowercase c denotes D-cysteine. Uppercase C denotes L-cysteine. Linker specifies the chemical group attached to the two cysteines via thioether bonds. Peptides with the allyl linker are unstapled, linear peptides in which both cysteines were alkylated using allyl bromide. Peptides were N-terminally capped with following caps: pa = pentynoic acid, acetyl = acetic acid, nicot = nicotinic acid, phenyl = phenylacetic acid, benzo = benzoic acid, hexano = hexanoic acid, hexyno = hexynoic acid, cyano = 3-cyanopropanoic acid, pentene = 4-pentenoic acid.

Our unique synthesis and screening strategy provided ample evidence that the activity of the stapled peptides was dependent on conformation. For instance, the ortho-xylene cross-linked DD5-o was active, whereas isomers of DD5-o that were cross-linked with meta- and para-xylene linkers (DD5-m and DD5-p) were not. This suggested that activity required not just the cyclic nature of the peptide, but the specific shape conferred by the ortho-xylene linker. Similarly, the meta-xylene cross-linked DD6-m was capable of inducing autophagy, while ortho- and para-xylene variants were not (FIG. 7). Activity was also dependent on the stereochemistry of the linker cysteines. Among stereoisomers of DD5-o, only the variant with two D-cysteines significantly increased autophagy. The L/D and D/L stereoisomers mildly increased autophagy and almost no increase was observed for the stereoisomer with two L-cysteines (FIG. 5, c; very mild activity is observed at 100 uM). The L/L stereoisomer (LL5-o) was thus used as a negative control in subsequent experiments. All together, these data showed that the activity of DD5-o depends on conformation, which in turn demonstrates the value of our conformation-varying approach to peptide stapling.

The activity of DD5-o was also dependent on the N-terminal cap. DD5-o was capped with 4-pentynoic acid, but when analogs with free or acetylated N-termini were tested, we observed no activity (FIG. 5, d). This led us to test a panel of alkyl and aryl N-terminal caps (FIG. 5, e and FIG. 8). Analogs with pentenyl, hexanyl, 3-cyanopropanyl, and hexynyl caps induced autophagy, but to a somewhat lesser extent than DD5-o (FIG. 8). Among peptides capped with aryl groups, an analog with a benzoic acid cap induced autophagy to a slightly lesser extent than DD5-o, but highly similar peptides with phenylacetic acid and nicotinic acid caps showed no activity.

An alanine scan was also performed on DD5-o to determine which residues are important for autophagy-inducing activity. Substituting Val1, Phe6, or Ile8 with Ala led to complete loss of activity (FIG. 9). Substituting Trp9 or His10 with Ala led to significantly decreased activity, while substituting Asn3 or His7 led to milder effects on activity. These data largely matched the alanine-scan data for Tat-11mer, demonstrating conservation of the hot spot residues and suggesting they share a common mechanism of action. The requirement for Val1 is, however, unique to DD5-o and suggests that Val1 and the N-terminal cap may together have direct effects on cell penetration.

Autophagy was measured in an additional assay to confirm the results obtained from immunoblotting, and to confirm that Tat-11mer and DD5-o truly induced autophagic flux (rather than blocking autophagosome maturation or lysosomal function). HeLa cells stably expressing GFP-LC3 were treated with peptide for 3 hours in serum-free media, and the number of GFP-LC3 puncta per cell were counted using fluorescence microscopy.[10] These experiments were also performed in the presence of bafilomycin A1 (Baf A1), which prevents the fusion of autophagosomes with lysosomes by inhibiting vacuolar ATPase (FIG. 1, a).[57] Autophagy induction causes an increase in numbers of autophagosomes per cell (quantifiable as GFP-LC3 puncta), which further increase when Baf A1 blocks lysosomal fusion.[58] Using this assay, we observed that DD5-o induced autophagy at 10 μM with nearly similar potency as Tat-Beclin 1, and Tat-11mer peptide showed roughly 4-fold more potent activation of autophagy (activity at 10 μM was similar to that of DD5-o at 40 μM, FIG. 5, f), All three peptides produced a further increase in GFP-LC3 puncta upon co-treatment with Baf A1. These results match the LC3 and p62 immunoblot data and are consistent with the previously published evidence that Beclin 1-derived peptides activate autophagy at the level of enhanced autophagosome formation.[10]

Immunoblot Assays.

Cells were treated with peptide in OPTI-MEM (Thermo Scientific) acidified with 0.15% (v/v) 6N HCl for 3 hour. Cells were rinsed with Dulbecco's phosphate buffered saline (PBS) and lysed in lysis buffer (20 mM HEPES, 150 mM NaCl, 1 mM EDTA, 1% Triton X-100, protease inhibitor cocktail (Roche) on ice for 1 hour. Cell lysates were centrifuged at 16,000 g for 10 min at 4° C. and analyzed by SDS-PAGE and transferred to PVDF membranes. The membranes were blocked 5% non-fat dry milk (NFDM) in PBST (PBS+0.05% Tween-20) for 1 hour, then incubated overnight at 4° C. with primary antibody in 5% NFDM in PBST. The blots were washed with PBST and incubated with HRP-conjugated secondary antibodies diluted in 5% NFDM in PBST for 1 hour at room temperature. Membranes were washed with PBST and visualized with SuperSignal West Pico Chemiluminescent Substrate (Thermo Scientific). Semi-quantitative results were obtained by noting the lowest concentration at which both p62 degradation and LC3-I to LC3-II conversion were observed.

Example 7: DD5-o Activates Autophagy In Vivo, and in a Huntington's Disease Model Despite its micromolar potency, the Tat-Beclin 1 peptide has been shown to be effective in several animal models of human disease. To show whether Tat-11mer and DD5-o have similar in vivo activity, we tested their ability to induce autophagy in GFP-LC3 transgenic mice[59] as described.[10] Peptides were delivered via intraperitoneal injection, and after 6 hours, muscle tissue was collected. GFP-LC3 puncta were imaged in thin sections and counted by an observer blinded to experimental condition (FIG. 10, a,b). We found that Tat-11mer produced the largest increase in autophagosome formation, while a control peptide with a Phe4 to Ser substitution had no effect on autophagy. Previous results showed that a retro inverso version of full-length Tat-Beclin 1 also possessed autophagy inducing activity in vivo.[10] Here, we tested a retro inverso version of Tat-11mer, and this D-amino acid peptide induced autophagy to a similar extent as the original Tat-Beclin 1 (FIG. 10, b). DD5-o induced autophagy at 15 and 30 mg/kg in a dose-dependent manner, while control peptide LL5-o had no effect (FIG. 10, a,b). In agreement with the in vitro data, at equimolar doses, DD5-o exhibits similar activity as full-length Tat-Beclin 1, while Tat-11mer is approximately 2- to 4-fold more potent.

Along with proteasomal degradation, autophagy is the major pathway by which aggregated proteins are removed from the cytoplasm. Increasing autophagy leads to the reduction of accumulated and aggregated protein, reversing a characteristic feature of polyglutamine disorders such as Huntington's disease (HD).[60] We thus tested whether our peptides would help clear protein aggregates from HeLa cells expressing a polyglutamine-expanded huntingtin exon 1 (htt103Q fused to CFP for imaging) from a doxycycline-repressible promoter.[10, 60] In this model of protein aggregation, autophagy has been shown to clear small aggregates, but not large (>1 μm) aggregates.[61] Treatment with 20 μM Tat-Beclin 1 previously was shown to decrease the number of small, but not large, htt103Q aggregates, consistent with autophagy-mediated protein turnover.[10] We found that treatment with 20 μM DD5-o or 10 μM Tat-11mer led to a significant decrease in the percentage of cells that have small aggregates, and in the number of small aggregates observed per cell (FIG. 10, c,d). Both peptides had potency greater than the full-length Tat-Beclin 1, which had no activity in this assay when tested at 12.5 μM, an equimolar concentration to active DD5-o or Tat-11mer. Control peptides Tat-11mer-scrambled and LL5-o produced no significant clearance of aggregates at equimolar concentrations.

GFP-LC3 In Vitro and In Vivo Experiments.

HeLa/GFP-LC3 cells generated as previously shown,[10] treated with peptides for 3 hour as described above. Cells were fixed with 2% paraformaldehyde (PFA) in PBS, GFP-LC3 puncta per cell were counted, and quantified as described.[86] To measure autophagy in mouse tissues, 6-week-old GFP-LC3 transgenic mice[59] (2 males and 2 females per experimental group) were injected i.p. with Tat-Beclin 1 (20 mg/kg), Tat-11mer (15 mg/kg), D-(Tat-11mer) (15 mg/kg), D-(Tat-11mer)_S (15 mg/kg), DD5-o (15, 30 mg/kg). After 6 h, mice were sacrificed and fixed by perfusion with 4% PFA in PBS. Tissues were fixed in 4% PFA overnight, 15% sucrose for 4 hours, and 30% sucrose overnight before frozen sections were prepared and used for fluorescence microscopy analysis as described.[16] GFP-LC3 puncta were quantified per 2500 μm² of tissue. Animal experiments were approved by the UTSW Institutional Animal Care Use Committee and performed in accordance with institutional guidelines.

Htt Aggregate Assay.

HeLa-htt103Q cells were cultured as described previously.[60] For the Htt103Q aggregate assay, cells were fixed with 2% PFA in PBS and CFP-positive aggregates <1 μm were counted via fluorescence microscopy by an observer blinded to experimental condition.

Example 8: Tat-Linked Linear Peptide Activity

Tat peptides have the following structure: YGRKKRRQRRRGG (SEQ ID NO: 16)-Sequence. In Table 2, bold amino acids show the mutation of WT (Tat-beclin-1). The N-terminus was capped with an acetyl group while the C terminus was capped with a —C(O)—NH₂ group. The activity reported is a summation of results from both the p62 degradation assay and the LC3 marker assay. The activity is recorded as follows:

-=activity not reported
0=decreased vs. WT
+=similar to WT
++=modest increase vs. WT
+++=significant increase vs. WT

TABLE 2

| Tat-Peptide | Sequence | Activity compared to wild-type WT |
|---|---|---|
| WT | VFNATFEIWHD (SEQ ID NO: 18) | |
| T1 | CFNATFEIWHD (SEQ ID NO: 19) | + |
| T2 | VWNATFEIWHD (SEQ ID NO: 21) | ++ |
| T3 | VFDATFEIWHD (SEQ ID NO: 22) | – |
| T4 | VFNSTFEIWHD (SEQ ID NO: 23) | – |

TABLE 2-continued

| Tat-Peptide | Sequence | Activity compared to wild-type WT |
|---|---|---|
| T5 | VFNACFEIWHD (SEQ ID NO: 24) | 0 |
| T6 | VFNATWEIWHD (SEQ ID NO: 28) | 0 |
| T7 | VFNATFDIWHD (SEQ ID NO: 29) | + |
| T8 | VFNATFELWHD (SEQ ID NO: 30) | ++ |
| T9 | VFNATFEIFHD (SEQ ID NO: 31) | + |
| T10 | VFNATFEIWYD (SEQ ID NO: 32) | + |
| T11 | VFNATFEIWHE (SEQ ID NO: 33) | + |
| T12 | VWNATFELWHD (SEQ ID NO: 34) | + |
| T13 | VYNATFEIWHD (SEQ ID NO: 35) | 0 |
| T14 | VFNATFEVWHD (SEQ ID NO: 36) | + |
| T15 | VLNATFEIWHD (SEQ ID NO: 37) | + |
| T16 | VFNATFEMWHD (SEQ ID NO: 38) | + |
| T17 | VWNATFHIWHD (SEQ ID NO: 5) | +++ |
| T18 | VFNATFEFWHD (SEQ ID NO: 39) | + |
| T19 | VFNATFEYWHD (SEQ ID NO: 40) | + |
| T20 | VFNATFERWHD (SEQ ID NO: 41) | + |
| T21 | FNATFEIWHD (SEQ ID NO: 42) | ++ |
| T22 | TFNATFEIWHD (SEQ ID NO: 43) | 0 |
| T23 | DFNATFEIWHD (SEQ ID NO: 44) | 0 |
| T24 | GFNATFEIWHD (SEQ ID NO: 45) | 0 |
| T25 | VFNATFEIWH (SEQ ID NO: 46) | ++ |
| T26 | VWNATFHYWHD (SEQ ID NO: 47) | +++ |
| T30 | FNATFEIWH (SEQ ID NO: 48) | + |
| T31 | FNATFHIWH (SEQ ID NO: 49) | + |
| T32 | WNATFHIWH (SEQ ID NO: 50) | ++ |
| T33 | VWNATFHIWH (SEQ ID NO: 7) | +++ |
| T34 | WNATFHIWHD (SEQ ID NO: 51) | +++ |
| T35 | WNATFHIW (SEQ ID NO: 52) | ++ |
| T36 | VWAATFHIWHD (SEQ ID NO: 53) | + |
| T37 | VWNAAFHIWHD (SEQ ID NO: 54) | ++ |
| T38 | VWNATAHIWHD (SEQ ID NO: 55) | - |
| T39 | VWNATFAIWHD (SEQ ID NO: 56) | +++ |
| T40 | VWNATFHAWHD (SEQ ID NO: 57) | - |
| T41 | VWNATFHIAHD (SEQ ID NO: 58) | + |
| T42 | VWNATFHIWAD (SEQ ID NO: 59) | +++ |
| T43 | VANATFHIWHD (SEQ ID NO: 60) | - |
| T44 | NATFHIW (SEQ ID NO: 61) | - |
| T45 | WNATFHI (SEQ ID NO: 62) | - |
| T46 | WNATFHIW (SEQ ID NO: 52) (no N-terminal Tat sequence) | - |

From the data above, FIG. 3 summarizes the effects of substituting one amino acid for another in the beclin-1 sequence. The top substitutions are given along with activity data (p62 degradation and LC3 marker assays) as to whether they were more, less, or about equal potency to Tat-beclin-1. The bottom substitutions indicate where alanine (A) was substituted for the given amino acid to determine the relative contribution that amino acid had to the overall peptide potency. For example, substituting T for A (and no other substitutions) resulted in a peptide that had greater activity that wild-type.

Example 9: Beclin-1 Analog Activity

Compounds 1-10 were evaluated using the assays described in Examples 4 and 5. Activity for each compound was measured in the p62 degradation assay and the LC3 marker assay as described herein. The activity at each concentration of peptide is given as, for example, (0/+) where 0 would be the p62/actin assay activity and + would be the LC3 assay activity. In some assays, the negative control was an inactive Tat-Beclin mutant, which does not induce autophagy. The results are shown in Tables 2-7 below.

TABLE 3

| | | | | | \multicolumn{4}{c}{Activity (µM)} | | | |
| --- | --- | --- | --- | --- | --- | --- | --- | --- |
| | | | | | \multicolumn{4}{c}{The control was vehicle.} | | | |
| Compound | Formula | Peptide | R₁ | Z | 10 | 20 | 50 | 100 |
| 1 | I | VCNATCHIWH (SEQ ID NO: 1) | A | MP | 0/0 | 0/0 | 0/0 | +++/+ |
| 2 | IIIa | VCNATCHIWH (SEQ ID NO: 1) | A | — | 0/0 | 0/0 | 0/0 | 0/0 |
| 3 | II | VCNACFHIWH (SEQ ID NO: 6) | A | OP | 0/0 | +/+++ | ++/+++ | +++/+++ |
| 4 | IIIb | VCNACFHIWH (SEQ ID NO: 6) | A | — | 0/0 | 0/0 | 0/0 | +++/+ |
| 5 | Non-cyclic peptide | VWNATFHIWH (SEQ ID NO: 7) | A | — | 0/0 | 0/0 | 0/+ | +/+ |
| 6 | Non-cyclic peptide | VWNATFHIWHD (SEQ ID NO: 5) | A | — | 0/0 | 0/0 | 0/0 | 0/0 |
| 7 | Non-cyclic peptide | YGRKKRRQRRR GGVWNATFHIWHD (SEQ ID NO: 63) | MeC(O) | — | 0/++* | +++/+++ | — | — |
| 8 | Non-cyclic peptide | YGRKKRRQRRR GGVWNATFHIWHD (SEQ ID NO: 63) | A | — | 0/+ | 0/++ | ++/+++ | — |
| 9 | II | VCNACFHIWH (SEQ ID NO: 6) | B | OP | 0/0 | 0/0 | 0/0 | — |
| 10 | II | VCNACFHIWH (SEQ ID NO: 6) | C | OP | 0/+ | 0/++ | 0/+++ | — |

TABLE 4

| | | | | | \multicolumn{4}{c}{Activity (µM)} | | | |
| --- | --- | --- | --- | --- | --- | --- | --- | --- |
| | | | | | \multicolumn{4}{c}{The control was an inactive Tat-Beclin mutant.} | | | |
| Compound | Formula | Peptide | R₁ | Z | 10 | 30 | 50 | 100 |
| 1 | I | VCNATCHIWH (SEQ ID NO: 1) | A | MP | 0/0 | 0/+ | 0/++ | 0/− |
| 3 | I | VCNATCHIWH (SEQ ID NO: 1) | A | OP | 0/++ | 0/+++ | 0/+ | 0/0 |
| Tat | Non-cyclic peptide | YGRKKRRQRRR (SEQ ID NO: 20) | H₂N | — | 0/0 | 0/0 | 0/+ | 0/0 |
| 1* | I | VCNATCHIWH (SEQ ID NO: 1) | A | MP | 0 | 0 | 0 | 0 |
| 3* | I | VCNATCHIWH (SEQ ID NO: 1) | A | OP | 0 | 0 | 0 | 0 |
| Tat* | Non-cyclic peptide | YGRKKRRQRRR (SEQ ID NO: 20) | H₂N | - | 0 | 0 | 0 | 0 |

TABLE 5

The control was compound T25.

| Compound | Formula | Peptide | $R_1$ | Z | Activity (μM) | | | |
|---|---|---|---|---|---|---|---|---|
| | | | | | 10 | 30 | 50 | 100 |
| 15 | I | VCNATCHIWH (SEQ ID NO: 2) | A | MP | 0/0 | +/+ | ++/++ | +++/+++ |
| 16 | I | VCNATCHIWH (SEQ ID NO: 2) | A | OP | 0/++ | 0/++ | 0/++ | 0/++ |
| 17 | I | VCNATCHIWH (SEQ ID NO: 2) | A | PP | +++/0 | ++/0 | ++/+ | ++/0 |
| 15* | I | VCNATCHIWH (SEQ ID NO: 2) | A | MP | 0 | + | +++ | +++ |
| 16* | I | VCNATCHIWH (SEQ ID NO: 2) | A | OP | 0 | + | ++ | ++ |
| 17* | I | VCNATCHIWH (SEQ ID NO: 2) | A | PP | 0 | ++ | +++ | +++ |

TABLE 6

The control was DMSO.

| Compound | Formula | Peptide | $R_1$ | Z | Activity (μM) | | | |
|---|---|---|---|---|---|---|---|---|
| | | | | | 10 | 30 | 50 | 100 |
| 18 | I | VCNATCHIWH (SEQ ID NO: 9) | A | OP | 0/0 | 0/0 | 0/0 | 0/0 |
| 19 | I | VCNATCHIWH (SEQ ID NO: 9) | A | MP | +/0 | ++/0 | ++/+ | +++/+ |
| 20 | I | VCNATCHIWH (SEQ ID NO: 9) | A | PP | ++/++ | +++/++ | +++/++ | +++/++ |
| T17 | Non-cyclic peptide | VWNATFHIWHD (SEQ ID NO: 5) | $H_2N$ | — | + | — | — | — |
| 21 | I | VCNATCHIWH (SEQ ID NO: 9) | A | PN | ++/0 | +++/0 | +++/0 | +++/0 |
| 22 | I | VCNATCHIWH (SEQ ID NO: 9) | A | PBP | +++/+ | +++/+ | +++/++ | +++/+ |
| 16 | I | VCNATCHIWH (SEQ ID NO: 2) | A | OP | ++/+ | +++/+ | +++/+ | +++/+ |
| 15 | I | VCNATCHIWH (SEQ ID NO: 2) | A | MP | ++/++ | +++/+ | +++/+ | +++/+ |
| 17 | I | VCNATCHIWH (SEQ ID NO: 2) | A | PP | +/++ | +++/++ | +++/++ | +++/+ |
| 23 | I | VCNATCHIWH (SEQ ID NO: 2) | A | PN | +/0 | ++/++ | +++/++ | +++/++ |
| 24 | I | VCNATCHIWH (SEQ ID NO: 2) | A | PBP | ++/++ | +++/++ | +++/++ | +++/++ |
| 25 | I | VCNATCHIWH (SEQ ID NO: 64) | A | OP | ++/++ | ++/++ | +++/+++ | +++/+++ |
| 26 | I | VCNATCHIWH (SEQ ID NO: 64) | A | MP | ++/+++ | +++/+++ | +++/+++ | +++/+++ |

TABLE 7

The control was compound T25.

| Compound | Formula | Peptide | $R_1$ | Z | Activity (μM) 30 | 50 | 100 |
|---|---|---|---|---|---|---|---|
| T25* | Non-cyclic peptide | VFNATFEIWH (SEQ ID NO: 46) | H₂N | – | +++ | – | – |
| 27 | I | VCNATCHIWH (SEQ ID NO: 1) | A | OP | 0/0 | 0/0 | 0/0 |
| 28 | I | VCNATCHIWH (SEQ ID NO: 1) | A | MP | 0/0 | 0/0 | +++/0 |
| 29 | I | VCNATCHIWH (SEQ ID NO: 1) | A | PP | 0/0 | +10 | ++/0 |
| 4 | IIIa | VCNATCHIWH (SEQ ID NO: 1) | A | – | 0/0 | ++/++ | +++/+++ |
| 30 | I | VCNATCHIWH (SEQ ID NO: 64) | A | PP | 0/0 | 0/0 | +/0 |
| 31 | I | VCNATCHIWH (SEQ ID NO: 64) | A | PN | 0/0 | 0/0 | 0/0 |
| 32 | I | VCNATCHIWH (SEQ ID NO: 64) | A | PBP | ++/0 | ++/0 | ++/0 |

*T25 at 5 μM is 0/++ and at 10 μM is +++/+++.

TABLE 8

The control was compound T25.

| Cmpd | Formula | Peptide | $R_1$ | Z | Activity (μM) 5 | 10 | 30 | 50 | 100 |
|---|---|---|---|---|---|---|---|---|---|
| T25* | Non-cyclic peptide | VFNATFEIWH (SEQ ID NO: 46) | H₂N | – | ++/+++ | ++/+++ | +++/+++* | – | – |
| 33 | I | VCNATCHIWH (SEQ ID NO: 1) | T | MP | 0/0 | 0/+ | +++/++ | +++/+++ | +++/+++ |
| 34 | IIIa | VCNATCHIWH (SEQ ID NO: 9) | T | – | 0/0 | 0/0 | +/++ | +++/+++ | +++/+++ |
| 35 | IIIa | VCNATCHIWH (SEQ ID NO: 1) | A | – | – | – | 0/0 | 0/+ | +++/++ | +++/++ |
| 36 | I | VCNATCHIWH (SEQ ID NO: 1) | H₂N | MP | – | – | – | 0/0 | 0/0 |
| 37 | I | VCNATCHIRIWH (SEQ ID NO: 65) | H₂N | MP | – | – | – | 0/0 | 0/0 |
| 38 | I | VCNATCHIWR (SEQ ID NO: 3) | H₂N | MP | – | – | – | 0/0 | 0/0 |
| 39 | IIIa | VCNATCHIWR (SEQ ID NO: 3) | H₂N | – | – | – | – | 0/0 | 0/0 |
| 40 | I | RCNARCRIWR (SEQ ID NO: 66) | H₂N | MP | – | – | – | 0/0 | 0/0 |
| 41 | IIIa | RCNARCRIWR (SEQ ID NO: 66) | H₂N | – | – | – | – | 0/0 | 0/0 |
| 42 | I | VCNATCRIWR (SEQ ID NO: 67) | H₂N | MP | – | – | – | 0/0 | 0/0 |
| 43 | IIIa | VCNATCRIWR (SEQ ID NO: 67) | H₂N | – | – | – | – | 0/0 | 0/0 |

TABLE 8-continued

The control was compound T25.

| Cmpd | Formula | Peptide | R₁ | Z | Activity (μM) 5 | 10 | 30 | 50 | 100 |
|---|---|---|---|---|---|---|---|---|---|
| 44 | I | VCNATCHIWH (SEQ ID NO: 1) | MeC(O)- | MP | — | — | — | 0/0 | 0/0 |
| 45 | I | VCNATCHIWR (SEQ ID NO: 3) | MeC(O)- | MP | — | — | — | 0/0 | 0/0 |
| 46 | I | VCNATCRIWR (SEQ ID NO: 67) | MeC(O)- | MP | — | — | — | 0/0 | 0/0 |
| 47 | I | VCNATCRIWR (SEQ ID NO: 67) | MeC(O)- | MP | — | — | — | 0/0 | 0/0 |
| 48 | IIIa | VCNATCHIWH (SEQ ID NO: 9) | T | — | — | — | — | +++/+++ | +++/+++ |
| 49 | I | VCNATCHIWH (SEQ ID NO: 1) | c(FΦRRRRE) (SEQ ID NO: 14)** | MP | — | — | — | +++/+++ | +++/+++ |
| 50 | IIIa | VCNATCHIWH (SEQ ID NO: 1) | c(FΦRRRRE) (SEQ ID NO: 14) | — | — | — | — | ++/+++ | ++/+++ |
| 51 | I | VCNATCHIWH (SEQ ID NO: 1) | FΦRRRRE (SEQ ID NO: 14) | MP | — | — | — | +++/+++ | +++/+++ |
| 3 | II | VCNACFHIWH (SEQ ID NO: 6) | A | OP | — | — | — | +++/+++ | +++/+++ |
| 52 | II | VCNACFHIWH (SEQ ID NO: 6) | A | MP | — | — | — | 0/+ | 0/+ |
| 53 | IIIb | VCNACFHIWH (SEQ ID NO: 6) | A | — | — | — | — | +++/++ | +++/++ |
| 54 | II | VCNACFHIWH (SEQ ID NO: 68) | A | OP | — | +/0 | ++/0 | ++/0 | — |
| 55 | II | VCNACFHIWH (SEQ ID NO: 68) | A | MP | — | 0/0 | ++/0 | +++/0 | — |
| 56 | IIIb | VCNACFHIWH (SEQ ID NO: 68) | A | — | — | 0/0 | +/0 | +/0 | — |
| 57 | IIIc | VCNACFHIWH (SEQ ID NO: 68) | C | — | — | 0/0 | +/0 | +/0 | — |
| 58 | V | VWNATCHIWC (SEQ ID NO: 11) | A | — | 0/0 | 0/0 | 0/0 | — | — |
| 59 c terminus | IV | VWNATCHIWC (SEQ ID NO: 69) | A | OP | 0/0 | 0/0 | 0/0 | — | — |
| 60 | IV | VWNATCHIWC (SEQ ID NO: 69) | A | MP | 0/0 | 0/0 | 0/0 | — | — |
| 61 | V | VWNATCHIWC (SEQ ID NO: 69) | A | — | 0/0 | 0/0 | 0/0 | — | — |
| 17 | Non-cyclic peptide | VWNATFHIWHD (SEQ ID NO: 5) | H2N | — | — | ++/+++ | +++/+++* | — | — |

TABLE 8-continued

The control was compound T25.

| Cmpd | Formula | Peptide | $R_1$ | Z | 5 | 10 | 30 | 50 | 100 |
|---|---|---|---|---|---|---|---|---|---|
| 62 | Non-cyclic peptide | VWNATFHIWHD (SEQ ID NO: 5) | c(FΦRRRRE) (SEQ ID NO: 14) | — | — | ++/+++ | +++/+++* | — | — |
| 63 | Non-cyclic peptide | VWNATFHIWHD (SEQ ID NO: 5) | A | — | — | 0/+ | 0/+++* | — | — |
| 64 | Non-cyclic peptide | VWNATFHIWH (SEQ ID NO: 7) | A | — | — | 0/0 | 0/0* | | |
| 65 | IV | VWNAT<u>C</u>HIWC (SEQ ID NO: 11) | A | OP | — | 0/0 | 0/0 | 0/0 | — |
| 66 | IV | VWNAT<u>C</u>HIWC (SEQ ID NO: 11) | A | MP | — | 0/0 | 0/0 | 0/0 | — |
| 67 | IV | VWNAT<u>C</u>HIW<u>C</u> (SEQ ID NO: 4) | A | OP | — | 0/0 | 0/0 | 0/0 | — |
| 68 | IV | VWNAT<u>C</u>HIW<u>C</u> (SEQ ID NO: 4) | A | MP | — | 0/0 | 0/0 | 0/0 | — |
| 1 | I | V<u>C</u>NAT<u>C</u>HIWH (SEQ ID NO: 1) | A | MP | — | 0/0* | 0/0 | 0/0 | +++/+ |
| 30 | IIIa | V<u>C</u>NAT<u>C</u>HIWH (SEQ ID NO: 1) | A | — | — | 0/0* | 0/0 | 0/0 | 0/0 |
| 3 | II | V<u>C</u>NA<u>C</u>FHIWH (SEQ ID NO: 6) | A | OP | — | — | — | — | +++/+++ |
| 6 | Non-cyclic peptide | VWNATFHIWHD (SEQ ID NO: 5) | A | — | — | — | — | — | 0/0 |
| 5 | Non-cyclic peptide | VWNATFHIWH (SEQ ID NO: 7) | A | — | — | — | — | — | 0/0 |
| 1 | I | V<u>C</u>NAT<u>C</u>HIWH (SEQ ID NO: 1) | A | MP | — | 0/+* | ++/+++ | +++/+++ | — |
| 2 | IIIa | V<u>C</u>NAT<u>C</u>HIWH (SEQ ID NO: 1) | A | — | — | 0/0* | 0/0 | 0/+ | — |
| 6 | Non-cyclic peptide | VWNATFHIWHD (SEQ ID NO: 5) | A | — | — | 0/0* | 0/0 | ++/0 | — |
| 5 | Non-cyclic peptide | VWNATFHIWH (SEQ ID NO: 7) | A | — | — | 0/0* | 0/0 | 0/0 | — |
| 3 | II | V<u>C</u>NA<u>C</u>FHIWH (SEQ ID NO: 6) | A | OP | — | 0/0* | 0/0 | +/0 | — |
| 69 | II | V<u>C</u>NA<u>C</u>FHIWH (SEQ ID NO: 6) | G | OP | — | 0/0* | 0/0 | ++/+++ | — |
| 70 | II | V<u>C</u>NA<u>C</u>FHIWH (SEQ ID NO: 6) | B | OP | — | 0/0* | 0/0 | 0/+ | — |
| 71 | II | V<u>C</u>NA<u>C</u>FHIWH (SEQ ID NO: 6) | C | OP | — | 0/+* | 0/++ | 0/+++ | — |

TABLE 8-continued

The control was compound T25.

| Cmpd | Formula | Peptide | $R_1$ | Z | \multicolumn{5}{c}{Activity (µM)} |
| | | | | | 5 | 10 | 30 | 50 | 100 |
| --- | --- | --- | --- | --- | --- | --- | --- | --- | --- |
| 72 | II | VCNACFHIWH (SEQ ID NO: 6) | E | OP | — | 0/0* | 0/0 | +/++ | — |
| 73 | II | VCNACFHIWH (SEQ ID NO: 6) | F | OP | — | 0/0* | 0/+ | +/+++ | — |
| 74 | II | VCNACFHIWH (SEQ ID NO: 6) | D | OP | — | 0/+* | 0/++ | +++/+++ | — |
| 75 | I | VCNATCHIWH (SEQ ID NO: 1) | T | MP | — | + | — | — | — |
| 76 | IIIa | VCNATCHIWH (SEQ ID NO: 1) | T | MP | — | + | — | — | — |

*Data taken at 20 instead of 30 µM.
**c(FΦRRRRE) (SEQ ID NO: 14) is a cyclic peptide where the F and E amino acids termini are bonded. Φ is L-2-naphthylalanine Example 10: Solution Structure of DD5-o The in vitro and in vivo data suggested that the stapled peptides required a specific 3D conformation. However, it was unclear what this conformation might be. The crystal structure of the ECD of Beclin 1 is composed of three consecutive and symmetrical β-sheet-α-helix autophagy-specific (BARA) motifs.[62] Published data have highlighted the importance of the ECD in the architecture of the autophagy initiation complex, though its role is not fully understood.[63, 64] The sequence of the ECD corresponding to the autophagy-inducing peptides is at the edge of the region that was crystallized, and shows no regular secondary structure (FIG. 1, b).[62] The amino acid composition and the relative positioning of hot spot residues were also not suggestive of a specific preferred secondary structure. Thus, it was unclear what structure this segment assumes in any relevant biological context.

We used 2D-NMR spectroscopy to determine the structure of DD5-o in methanol (FIG. 16). Specifically, all the NMR experiments were carried out using a Bruker 500 MHz spectrometer. Peptide DD5-o was dissolved in $CD_3OH$ at a concentration of roughly 2 mM. Complete resonance assignments were achieved using a combination of homonuclear $^1H$-$^1H$ COSY, TOCSY and ROESY experiments at 289 K. Standard pulse programs available in the Bruker library were used for all experiments. The residual methyl signal in $CD_3OH$ was used as an internal standard for chemical shift referencing.

NMR spectra were processed in Bruker Topspin software and imported into CcpNMR Analysis v2.4.2 for assignments and to generate distance constraints. A total of 114 NOEs were compiled, including 12 medium- and long-range NOEs. Three phi dihedral angle constraints, derived from $JN_H$-$C_{aH}$ coupling constants, were also compiled. These were used as constraints in simulated annealing experiments using CNS Solve version 1.3. Simulated annealing involved a high-temperature annealing stage of 1000 steps, followed by two slow-cooling stages, each 1000 steps, which was then followed by a 10 cycles of 200 steps of energy minimization. Structure calculations were iterated until the distance and dihedral violations were completely resolved. A total of 25-lowest energy structures with no NOE and dihedral angle violation greater than 0.1 Å and 5°, respectively, were then selected for further analysis.

The 1D proton spectrum was well-resolved with excellent dispersion among the amide protons (FIG. 11). Two-dimensional COSY, TOCSY, and ROESY were recorded (FIGS. 12-14), allowing complete assignment. Chemical shifts deviated from random coil values in a manner consistent with an overall helical structure (Table 9). NOEs between (i, i+1) amide protons were also observed from D-Cys2 to Trp9, consistent with an uninterrupted helical structure across nearly the entire length of the peptide. Medium-range and long-range NOEs also spanned the entire length of the peptide (FIG. 16, a). These data indicated a high degree of structure both in the N-terminal, stapled portion and in the C-terminal portion. An ensemble of the 25 lowest-energy structures from simulated annealing simulations (FIG. 16, b) showed tight agreement, with a well-structured, helical backbone (backbone RMSD=0.44 Å, all-heavy-atom RMSD=1.1 Å). Circular dichroism experiments revealed a helical signature (FIG. 15), confirming that DD5-o forms a robust α-helix in solution. Finally, molecular dynamics simulations of DD5-o in explicit water provided evidence that the NMR-derived structure is stable in aqueous solution. The complete 100 ns simulation, revealing dynamics of this new class of stapled helix, is shown in FIG. 18.

TABLE 9

$^1H$ chemical shifts for DD5-o at 289 K in $CD_3OH$.

| Residue | $H_N$ | $H_\alpha$ | $H_\beta$ | other protons |
| --- | --- | --- | --- | --- |
| Val2 | 8.54 | 3.86 | 2.10 | γ = 1.11, 1.10 |
| D-Cys3 | 8.82 | 4.63 | 3.06, 3.38 | — |
| Asn4 | 8.43 | 4.46 | 2.79, 2.92 | δ2 = 7.12, 7.74 |
| Ala5 | 8.32 | 4.07 | 1.45 | — |
| D-Cys6 | 7.87 | 3.65 | 2.92, 3.02 | — |
| Phe7 | 7.93 | 4.31 | 3.02, 3.18 | δ = 7.17; ε = 7.17; ζ = 7.16 |
| His8 | 8.15 | 4.42 | 3.29, 3.39 | δ2 = 7.48; ε1 = 8.81 |
| Ile9 | 7.84 | 3.96 | 1.84, 2.12 | γ1 = 1.16, 1.63; γ2 = 0.84; δ1 = 0.75 |
| Trp10 | 8.06 | 4.47 | 3.06, 3.16 | δ1 = 7.23; ε1 = 10.51; ε3 = 7.55; ζ2 = 7.34; ζ3 = 7.13; η2 = 7.01 |
| His11 | 7.94 | 4.59 | 2.82, 3.19 | δ2 = 7.16; ε1 = 8.68 |

Note:
for software compatibility purposes, the pentynoic acid cap was numbered residue 1, the first amino acid (Val) was numbered 2, etc.

TABLE 10

List of NOE-derived distance constraints and phi dihedral angle restraints used to calculate solution NMR structures of DD5-o.

Distance constraints:

assign ( resid 2 and name HN ) ( resid 2 and name HA ) 3.1 0.6 0.6
assign ( resid 2 and name HN ) ( resid 2 and name HB ) 3.0 0.6 0.6
assign ( resid 2 and name HN ) ( resid 2 and name HG2# ) 3.1 0.6 0.6
assign ( resid 2 and name HA ) ( resid 2 and name HB ) 3.0 0.6 0.6
assign ( resid 2 and name HA ) ( resid 2 and name HG2# ) 2.7 0.5 0.5
assign ( resid 2 and name HA ) ( resid 2 and name HG1# ) 2.7 0.5 0.5
assign ( resid 2 and name HA ) ( resid 3 and name HB1 ) 4.2 0.7 0.7
assign ( resid 2 and name HA ) ( resid 5 and name HB1 ) 3.8 0.8 0.8
assign ( resid 3 and name HN ) ( resid 2 and name HA ) 2.6 0.5 0.5
assign ( resid 3 and name HN ) ( resid 2 and name HB ) 4.3 0.9 0.9
assign ( resid 3 and name HN ) ( resid 2 and name HG2# ) 4.0 0.8 0.8
assign ( resid 3 and name HN ) ( resid 2 and name HG1# ) 4.0 0.8 0.8
assign ( resid 3 and name HN ) ( resid 3 and name HA ) 3.0 0.7 0.7
assign ( resid 3 and name HN ) ( resid 3 and name HB2 ) 3.9 0.8 0.8
assign ( resid 3 and name HN ) ( resid 3 and name HB1 ) 3.9 0.8 0.8
assign ( resid 3 and name HA ) ( resid 3 and name HB2 ) 3.1 0.6 0.6
assign ( resid 3 and name HA ) ( resid 3 and name HB1 ) 3.2 0.7 0.7
assign ( resid 3 and name HB1 ) ( resid 3 and name HB2 ) 2.3 0.5 0.5
assign ( resid 3 and name HN ) ( resid 4 and name HN ) 3.5 0.8 0.8
assign ( resid 4 and name HN ) ( resid 2 and name HA ) 4.1 0.8 0.8
assign ( resid 4 and name HN ) ( resid 3 and name HA ) 3.5 0.8 0.8
assign ( resid 4 and name HN ) ( resid 4 and name HA ) 3.0 0.6 0.6
assign ( resid 4 and name HN ) ( resid 4 and name HB1 ) 3.6 0.7 0.7
assign ( resid 4 and name HN ) ( resid 4 and name HB2 ) 2.9 0.6 0.6
assign ( resid 4 and name HD21 ) ( resid 4 and name HB1 ) 2.9 0.7 0.7
assign ( resid 4 and name HD21 ) ( resid 4 and name HB2 ) 3.3 0.7 0.7
assign ( resid 4 and name HA ) ( resid 4 and name HB2) 3.0 0.6 0.6
assign ( resid 4 and name HA ) ( resid 4 and name HB1 ) 2.8 0.6 0.6
assign ( resid 4 and name HD22 ) ( resid 4 and name HB1 ) 3.4 0.7 0.7
assign ( resid 4 and name HD21 ) ( resid 4 and name HA ) 4.2 0.8 0.8
assign ( resid 5 and name HN ) ( resid 2 and name HA ) 4.1 0.9 0.9
assign ( resid 5 and name HN ) ( resid 4 and name HA ) 3.8 0.8 0.8
assign ( resid 5 and name HN ) ( resid 4 and name HB1 ) 3.6 0.8 0.8
assign ( resid 5 and name HN ) ( resid 4 and name HB2 ) 4.1 0.8 0.8
assign ( resid 5 and name HN ) ( resid 4 and name HN ) 3.4 0.7 0.7
assign ( resid 5 and name HN ) ( resid 5 and name HA ) 2.9 0.6 0.6
assign ( resid 5 and name HN ) ( resid 5 and name HB1 ) 3.0 0.6 0.6
assign ( resid 5 and name HA ) ( resid 5 and name HB# ) 2.7 0.5 0.5
assign ( resid 5 and name HN ) ( resid 6 and name HN ) 3.1 0.7 0.7
assign ( resid 6 and name HN ) ( resid 2 and name HA ) 4.2 0.8 0.8
assign ( resid 6 and name HN ) ( resid 5 and name HA ) 3.9 0.8 0.8
assign ( resid 6 and name HN ) ( resid 5 and name HB# ) 3.5 0.7 0.7
assign ( resid 6 and name HN ) ( resid 6 and name HA ) 2.8 0.5 0.5
assign ( resid 6 and name HN ) ( resid 6 and name HB1 ) 3.9 0.8 0.8
assign ( resid 6 and name HN ) ( resid 7 and name HN ) 3.4 0.7 0.7
assign ( resid 7 and name HN ) ( resid 4 and name HA ) 3.3 0.6 0.6
assign ( resid 7 and name HN ) ( resid 6 and name HA ) 3.1 0.6 0.6
assign ( resid 7 and name HN ) ( resid 7 and name HA ) 3.1 0.6 0.6
assign ( resid 7 and name HA ) ( resid 7 and name HB2 ) 2.9 0.6 0.6
assign ( resid 7 and name HA ) ( resid 7 and name HB1 ) 2.9 0.6 0.6
assign ( resid 7 and name HN ) ( resid 7 and name HB1 ) 3.0 0.6 0.6
assign ( resid 7 and name HN ) ( resid 7 and name HB2 ) 3.1 0.7 0.7
assign ( resid 8 and name HN ) ( resid 5 and name HA ) 3.8 0.8 0.8
assign ( resid 8 and name HD2 ) ( resid 5 and name HA ) 3.6 0.7 0.7
assign ( resid 8 and name HN ) ( resid 7 and name HA ) 3.3 0.7 0.7
assign ( resid 8 and name HN ) ( resid 7 and name HB2 ) 3.6 0.7 0.7
assign ( resid 8 and name HN ) ( resid 7 and name HB1 ) 4.3 0.9 0.9
assign ( resid 8 and name HN ) ( resid 7 and name HN ) 3.3 0.7 0.7
assign ( resid 8 and name HN ) ( resid 8 and name HA ) 3.1 0.6 0.6
assign ( resid 8 and name HN ) ( resid 8 and name HB2 ) 3.0 0.6 0.6
assign ( resid 8 and name HN ) ( resid 8 and name HB1 ) 2.8 0.7 0.7
assign ( resid 8 and name HD2 ) ( resid 8 and name HB2 ) 3.6 0.7 0.7
assign ( resid 8 and name HD2 ) ( resid 8 and name HB1 ) 3.6 0.7 0.7
assign ( resid 8 and name HD2 ) ( resid 8 and name HA ) 3.8 0.7 0.7
assign ( resid 8 and name HD2 ) ( resid 8 and name HE1 ) 4.4 0.9 0.9
assign ( resid 8 and name HD2 ) ( resid 9 and name HA ) 4.4 0.9 0.9
assign ( resid 8 and name HN ) ( resid 9 and name HN ) 3.4 0.7 0.7
assign ( resid 9 and name HB ) ( resid 6 and name HB1 ) 3.5 0.7 0.7
assign ( resid 9 and name HN ) ( resid 8 and name HA ) 3.2 0.6 0.6
assign ( resid 9 and name HN ) ( resid 8 and name HB2 ) 4.1 0.8 0.8
assign ( resid 9 and name HN ) ( resid 8 and name HB1 ) 3.6 0.8 0.8
assign ( resid 9 and name HN ) ( resid 9 and name HA ) 3.2 0.6 0.6
assign ( resid 9 and name HN ) ( resid 9 and name HB ) 2.8 0.6 0.6
assign ( resid 9 and name HN ) ( resid 9 and name HG11 ) 3.8 0.7 0.7
assign ( resid 9 and name HN ) ( resid 9 and name HG12 ) 3.9 0.8 0.8

TABLE 10-continued

List of NOE-derived distance constraints and phi dihedral angle restraints used to calculate solution NMR structures of DD5-o.

assign ( resid 9 and name HA ) ( resid 9 and name HB ) 3.1 0.6 0.6
assign ( resid 9 and name HA ) ( resid 9 and name HG11 ) 3.3 0.7 0.7
assign ( resid 9 and name HA ) ( resid 9 and name HG12 ) 3.2 0.7 0.7
assign ( resid 9 and name HA ) ( resid 9 and name HG2# ) 3.2 0.7 0.7
assign ( resid 9 and name HG12 ) ( resid 9 and name HB ) 3.6 0.7 0.7
assign ( resid 9 and name HB ) ( resid 9 and name HD1# ) 2.9 0.6 0.6
assign ( resid 10 and name HN ) ( resid 7 and name HA ) 4.2 0.8 0.8
assign ( resid 10 and name HE3 ) ( resid 7 and name HA ) 4.2 0.8 0.8
assign ( resid 10 and name HD1 ) ( resid 7 and name HA ) 4.2 0.8 0.8
assign ( resid 10 and name HN ) ( resid 9 and name HN ) 3.6 0.8 0.8
assign ( resid 10 and name HN ) ( resid 9 and name HA ) 2.9 0.6 0.6
assign ( resid 10 and name HN ) ( resid 9 and name HB ) 3.8 0.7 0.7
assign ( resid 10 and name HD1 ) ( resid 9 and name HD1# ) 4.0 0.8 0.8
assign ( resid 10 and name HD1 ) ( resid 9 and name HB ) 4.0 0.8 0.8
assign ( resid 10 and name HN ) ( resid 10 and name HA ) 3.1 0.6 0.6
assign ( resid 10 and name HN ) ( resid 10 and name HB1 ) 3.0 0.6 0.6
assign ( resid 10 and name HN ) ( resid 10 and name HB2 ) 3.3 0.7 0.7
assign ( resid 10 and name HA ) ( resid 10 and name HB1 ) 3.0 0.7 0.7
assign ( resid 10 and name HA ) ( resid 10 and name HB2 ) 2.8 0.6 0.6
assign ( resid 10 and name HE3 ) ( resid 10 and name HB1 ) 3.2 0.8 0.8
assign ( resid 10 and name HE3 ) ( resid 10 and name HB2 ) 3.2 0.7 0.7
assign ( resid 10 and name HE3 ) ( resid 10 and name HA ) 3.8 0.6 0.6
assign ( resid 10 and name HD1 ) ( resid 10 and name HB2 ) 3.5 0.7 0.7
assign ( resid 10 and name HD1 ) ( resid 10 and name HB1 ) 3.3 0.7 0.7
assign ( resid 10 and name HD1 ) ( resid 10 and name HA ) 3.6 0.6 0.6
assign ( resid 10 and name HE1 ) ( resid 10 and name HD1 ) 3.0 0.6 0.6
assign ( resid 10 and name HE1 ) ( resid 10 and name HZ2 ) 3.5 0.7 0.7
assign ( resid 10 and name HN ) ( resid 10 and name HD1 ) 3.9 0.8 0.8
assign ( resid 11 and name HE1 ) ( resid 7 and name HA ) 4.3 0.9 0.9
assign ( resid 11 and name HN ) ( resid 10 and name HA ) 3.3 0.6 0.6
assign ( resid 11 and name HN ) ( resid 11 and name HA ) 3.0 0.7 0.7
assign ( resid 11 and name HA ) ( resid 11 and name HB1 ) 2.9 0.7 0.7
assign ( resid 11 and name HA ) ( resid 11 and name HB2 ) 2.8 0.6 0.6
assign ( resid 11 and name HN ) ( resid 11 and name HB1 ) 3.3 0.7 0.7
assign ( resid 11 and name HN ) ( resid 11 and name HA ) 3.5 0.7 0.7
assign ( resid 11 and name HD2 ) ( resid 11 and name HB2 ) 3.5 0.7 0.7
assign ( resid 11 and name HE1 ) ( resid 11 and name HD2 ) 4.1 0.8 0.8
assign ( resid 11 and name HB1 ) ( resid 11 and name HB2 ) 2.2 0.4 0.4
assign ( resid 11 and name HD2 ) ( resid 11 and name HE1 ) 4.2 0.8 0.8

Phi dihedral angle restraints:

assign ( resid 1 and name c ) ( resid 2 and name n )
    ( resid 2 and name ca ) ( resid 2 and name c ) 1.0 −60.0 30.0 2
assign ( resid 3 and name c ) ( resid 4 and name n )
    ( resid 4 and name ca ) ( resid 4 and name c ) 1.0 −60.0 30.0 2
assign ( resid 4 and name c ) ( resid 5 and name n )
    ( resid 5 and name ca ) ( resid 5 and name c ) 1.0 −60.0 30.0 2

TABLE 11

NMR structural data and refinement statistics for DD5-o.

| | DD5-o |
|---|---|
| NMR distance and dihedral constraints | |
| Distance constraints | |
| Total NOE | 114 |
| Intra-residue | 72 |
| Inter-residue | 42 |
| Sequential ($|i-j| = 1$) | 30 |
| Medium-range to long range ($|i-j| \geq 2$) | 12 |
| φ dihedral angle restraints | 3 |
| Structure statistics | |
| Violations | |
| Distance violations >0.1 (Å) | 0 |
| Dihedral angle violations >5 (°) | 0 |
| Deviations from idealized geometry | |
| Bond lengths (Å) | 0.0043 ± 0.00017 |
| Bond angles (°) | 0.4159 ± 0.0181 |
| Impropers (°) | 0.2210 ± 0.0167 |

TABLE 11-continued

NMR structural data and refinement statistics for DD5-o.

|  | DD5-o |
|---|---|
| Coordinate precision | |
| Heavy (Å) | 1.101 |
| Backbone (Å) | 0.449 |

Example 11: Molecular Dynamics Simulations of DD5-o in Explicit Water

Molecular dynamics (MD) simulations were performed with the Gromacs 4.6.7 engine in conjunction with the CHARMM22 force field with CMAP correction. The parameters for the D-Cys residue and the o-xyl linker were determined based on chemical similarity to already-defined atom types (see FIG. 17). The TTP3P water model was used for solvent molecules. The average NMR structure, as solved in methanol, was used as the input configuration for the simulation. In the MD simulation, the N-terminal 4-pentynoic acid cap was replaced by an acetyl group, and the double protonation state for the two His residues was used. After an energy minimization of 1000 steps in vacuum, the peptide was solvated in a cubic water box. The dimension of the water box was chosen such that the minimum distance between the peptide and the box edges was 10 Å. Two Cl⁻ ions were added to neutralize the net charge of the system. The solvated system was optimized for 5000 steps using the steepest descent algorithm to remove any bad contacts. With all peptide heavy atoms restrained to their initial positions, the minimized system was heated from 5K to 300K within 20 ps and relaxed for additional 30 ps. Before production, the system was further equilibrated for 100 ps with the peptide backbone atoms remain fixed.

The production simulation was performed in the NPT (isothermal-isobaric) ensemble at 300K/1 bar. The temperature was controlled using the Nosé-Hoover thermostat with a coupling constant of 1.0 ps. To alleviate the "hot-solvent/cold-solute" artifact, two separate thermostats were applied to both the peptide and the solvent molecules. The pressure of the system was maintained using an isotropic Berendsen barostat, with a coupling time of 2.0 ps and a compressibility of $4.5 \times 10^{-5}$ bar$^{-1}$. All bonds were constrained with the LINCS algorithm to enable the use of a 2 fs time step with the leap-frog algorithm. The non-bonded interactions (Lennard-Jones and Columbic) were truncated at 8 Å. Long-range Columbic interactions beyond the cut-off distance were treated using the Particle Mesh Ewald (PME) summation method. A long-range analytic dispersion correction was applied to both the energy and pressure to account for the truncation of Lennard-Jones interactions. The production simulation was performed for 100 ns. In the production simulation, the C-terminal residues underwent side-chain reorganization and formed a related (slightly more α-helical) structure in water. Once formed, the structure was relatively stable during the rest of the simulation. This behavior was observed in three independent runs, which each started from different initial velocities (FIG. 18).

Example 12: A New Assay for Measuring Relative Cytosolic Access

DD5-o has similar activity as Tat-Beclin 1, but is roughly one-third the size and does not require a polycationic transducing sequence. Extensive biological data support that these autophagy-inducing peptides act at the stage of autophagy initiation, during which a large Beclin 1-mediated complex must assemble in order to nucleate autophagosome formation.[10, 63] Since this complex is associated with the cytoplasmic surfaces of the endoplasmic reticulum and other organelles, it was critical to verify that DD5-o reaches the cytosol and to quantify the relative extent of cytosolic delivery without interference from endosomally trapped peptide.[48, 65-67] Due to the small size and relative hydrophobicity of the peptide, and due to the sensitivity of the SAR, we wanted to avoid using large perturbing tags such as fluorescent dyes. For these reasons, we developed a novel cell penetration assay to quantify the cytosolic delivery of DD5-o. The assay, called Chloroalkane Penetration Assay (CAPA), is inexpensive, quantitative, high-throughput, does not require labelling with large aromatic dyes, and can be adapted for measuring access to any cellular compartment (FIG. 19, a).

The Chloroalkane Penetration Assay is described in detail in U.S. Provisional Application No. 62/424,955, filed Nov. 21, 2016, and corresponding to U.S. Pat. No. 10,620,214, which is incorporated herein by reference in its entirety. Briefly, this assay uses a cell line that stably expresses a cytosolically-oriented protein as a fusion with GFP and Haloenzyme. Haloenzyme is a modified bacterial chloroalkane dehydrogenase that covalently labels itself with the small, otherwise inert Haloligand functional group.[68-70] If an exogenously added molecule bearing the Haloligand (a small chloroalkane) reaches the cytosol, it reacts exclusively with the Haloenzyme and blocks its active site. Following this incubation period, the amount of unreacted Haloenzyme was measured by chasing with a Haloligand-bearing dye (here, Htag-TAMRA). The relative amount of red cellular fluorescence after this chase was then quantified by flow cytometry. The red signal reports directly on the amount of free Haloenzyme, which is inversely proportional to the degree to which the added molecule accessed the cytoplasm during the incubation period. We evaluated CAPA with HTag-cTMP, a small molecule previously used as a tool for cytosolic protein localization.[71] As quantitated by flow cytometry, we observed inhibition of the HTag-TAMRA signal when cells were pre-incubated with HTag-cTMP, and this inhibition was dose-dependent with respect to amount of the HTag-cTMP used in the pre-incubation step. Fluorescence microscopy confirmed that the HTag-TAMRA colocalized with the cytosolically oriented GFP-Haloenzyme, and that pre-incubation with HTag-cTMP suppressed up to 90% of the HTag-TAMRA signal (FIG. 19, b). HTag-DD5-o, in which the DD5-o sequence is capped with the Haloligand, was synthesized, and LC3 and p62 immunoblot assays verified that it increased autophagy similarly to the original DD5-o (FIG. 21). In the Chloroalkane Penetration Assay, HTag-DD5-o produced dose-dependent suppression of the HTag-TAMRA signal (FIG. 19, b,c). Its dose-dependence curve was similar in shape to HTag-cTMP, but was shifted 100-fold higher in concentration, as expected for a peptide relative to a small molecule (FIG. 1c). We also tested a negatively charged, linear variant which exhibited cytosolic entry only at very high concentrations and at the limit of solubility (FIG. 19, c). Thus, the rapid, inexpensive Chloroalkane Penetration Assay confirmed the cytosolic localization of HTag-DD5-o at micromolar concentrations, which correlates with the concentrations at which it activates autophagy.

Chloroalkane Penetration Assay.

HaLo-GFP-Mito+mCherry-DHFR HeLa cells were obtained from the Chenoweth Lab.[71] Cells were cultured using DMEM+10% FBS+1% Pen/Strep+1 µg/mL puromycin. For experiments, cells were seeded in a 24-well plate the day before at $1.0 \times 10^5$ cells/well. Cells were rinsed 1× with PBS, then treated with peptides in acidified Opti-MEM (0.15% 6N HCl) for 4 hour. Media was aspirated and cells were washed for 30 min with phenol red-free DMEM+10% FBS+1% pen/strep. Cells were chased with 5 µM HTag-TAMRA (Promega) in phenol red-free DMEM+10% FBS+1% pen/strep for 30 min. Cells were washed for 15 min with phenol red-free DMEM+10% FBS+1% pen/strep. Cells were rinsed 1× with PBS, then trypsinized and transferred to eppys. Cells were pelleted and washed with PBS 2×. Cell pellet was resuspended in 250 µL of PBS and 200 µL were transferred to 96-well plate for flow cytometry analysis. Data was gated for live cells measuring 10,000 cells per sample. Mean fluorescence intensity was obtained in the Yellow channel for HTag-TAMRA, and data was normalized. Background yellow fluorescence was observed both by flow cytometry and microscopy due to the constituent expression of mCherry-DHFR, but the signal observed for HTag-TAMRA-treated cells was 10-fold higher than background.

Example 13: Additional Peptides

Additional peptide compounds (Table 12) are assayed for inducing autophagy in a p62 degradation assay and an LC3 marker assay as described above.

TABLE 12

| Sample # | Peptide name |
|---|---|
| 1 | paH10K(len)o |
| 2 | pa + 11K(len)o |
| 3 | isovalalDD5o |
| 4 | valalDD5o |
| 5 | heptalDD5o |
| 6 | paI8(nv)o |
| 7 | paI8(aep)o |
| 8 | paV1(aep)o |
| 9 | HTag-10mer |
| 10 | HTag-11mer |

Structures of the peptides in Table 12 are shown below.

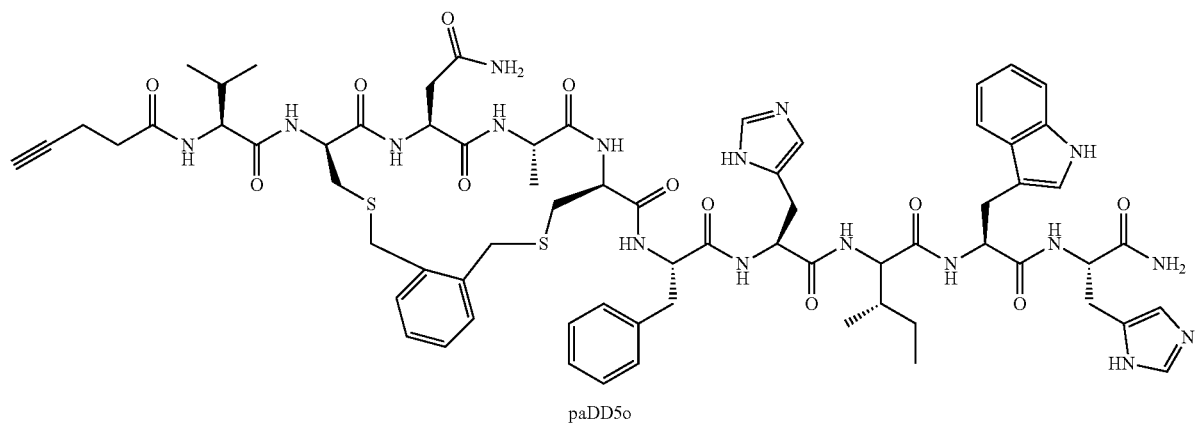

paDD5o

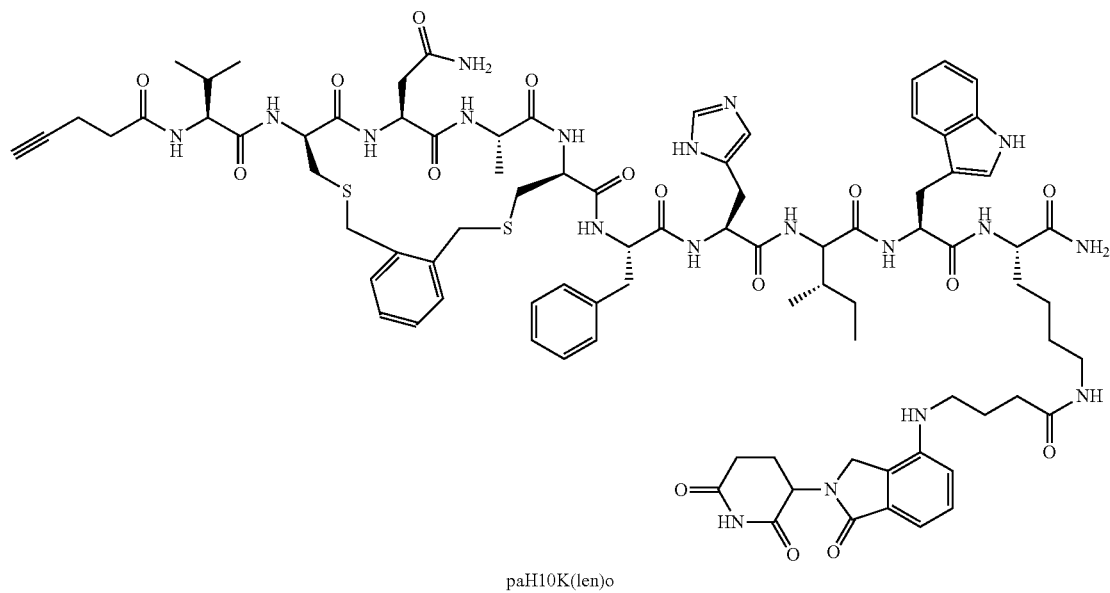

paH10K(len)o

-continued
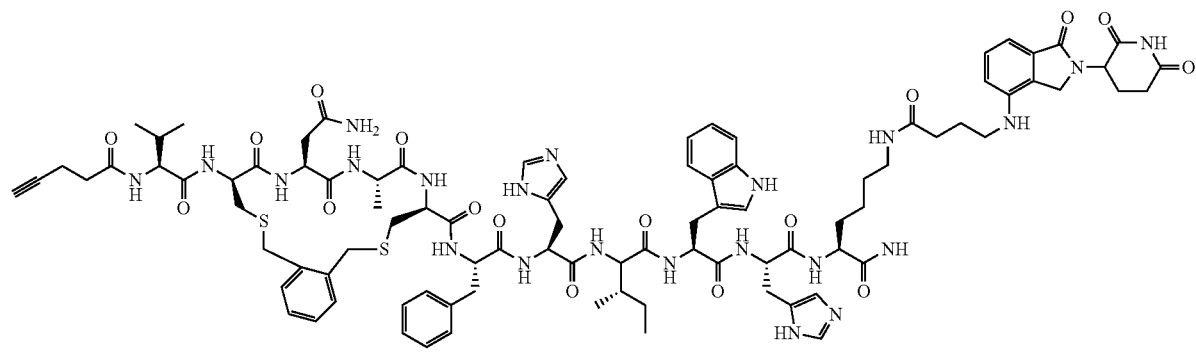
pa + 11K(len)o
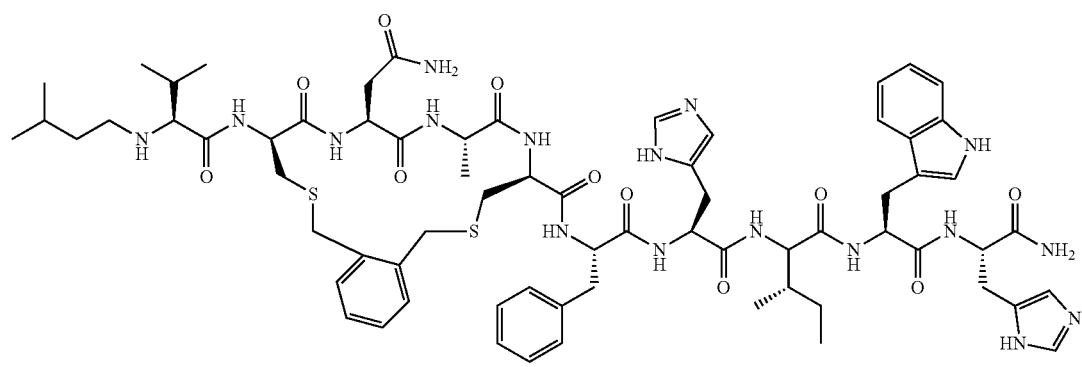
isovalalDD5o
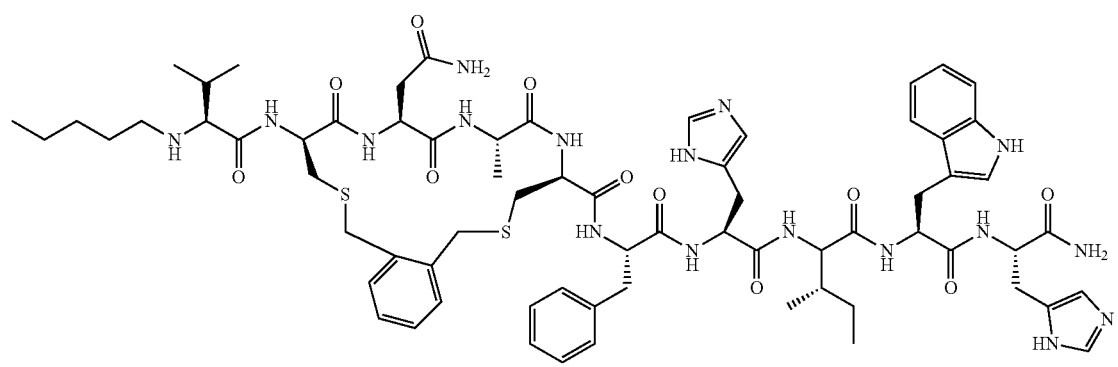
valalDD5o
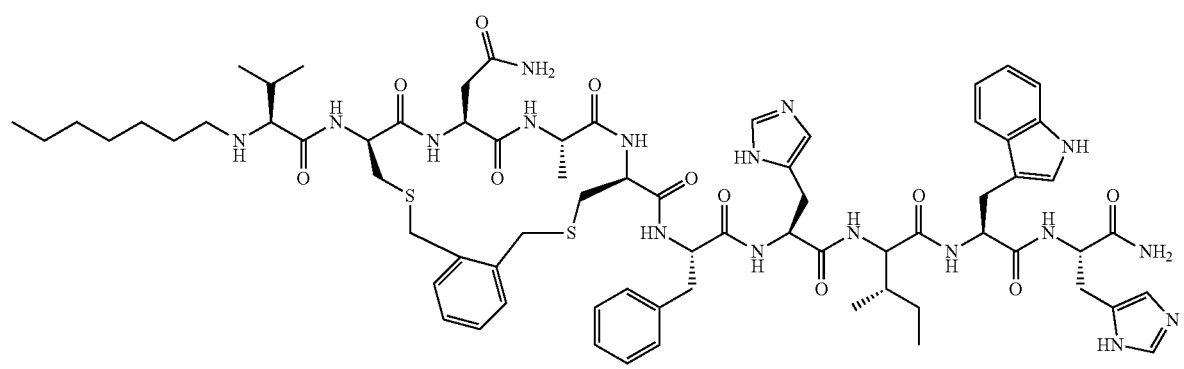
heptalDD5o

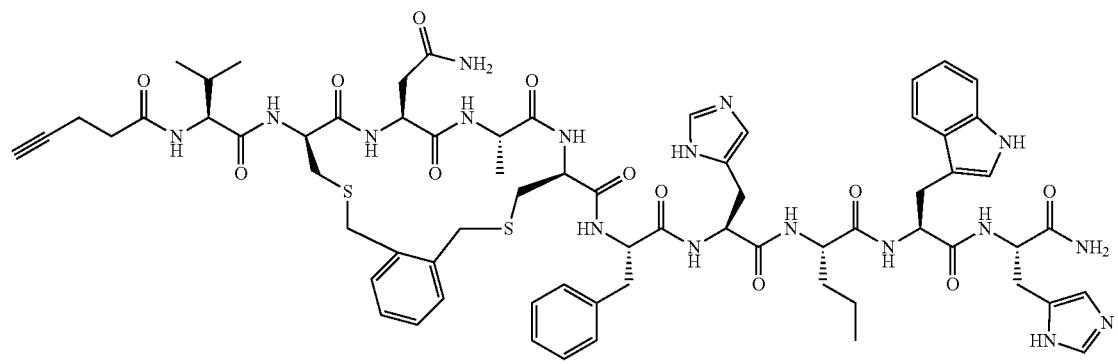
pal8(nv)o
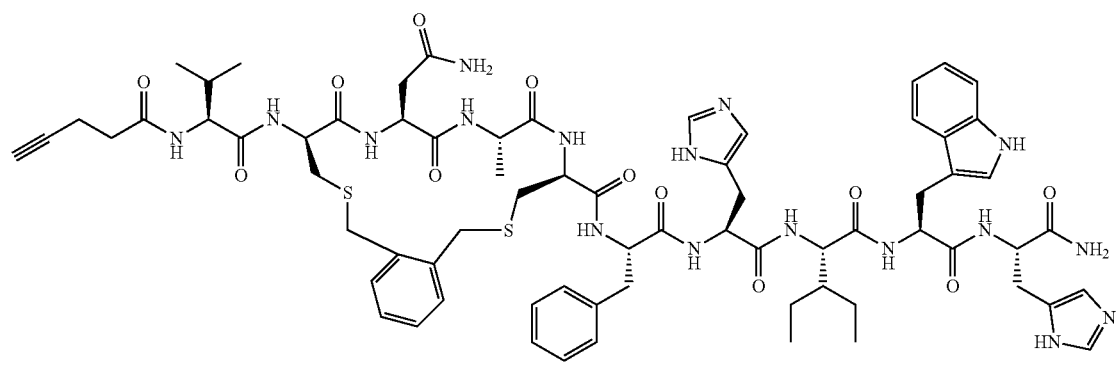
pal8(aep)o
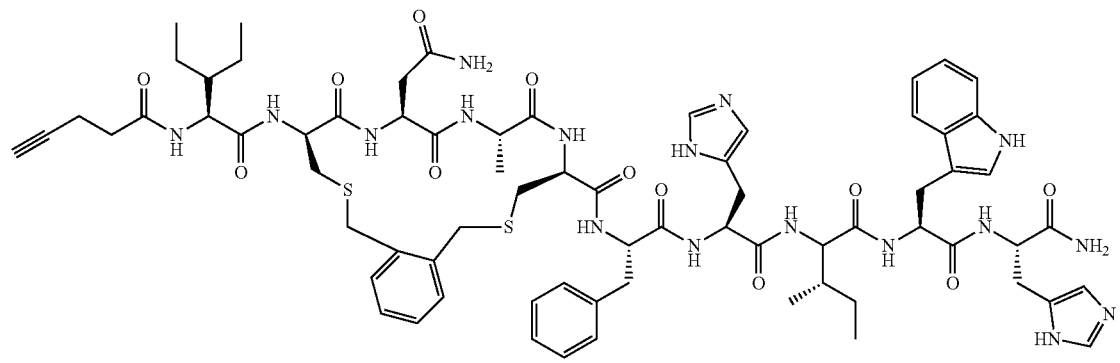
paV1(aep)o
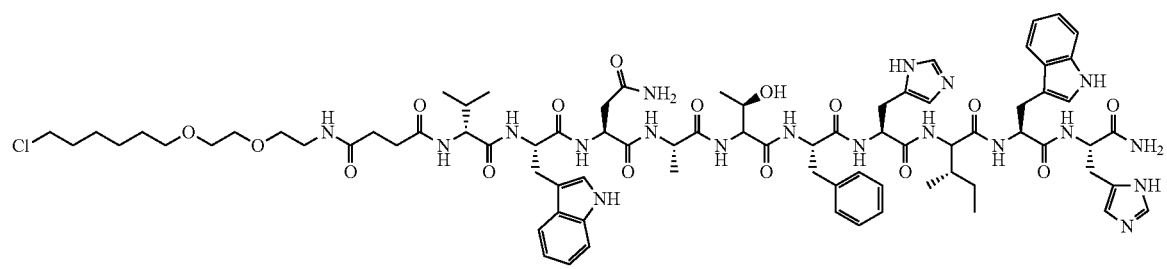
HTag-10mer -continued

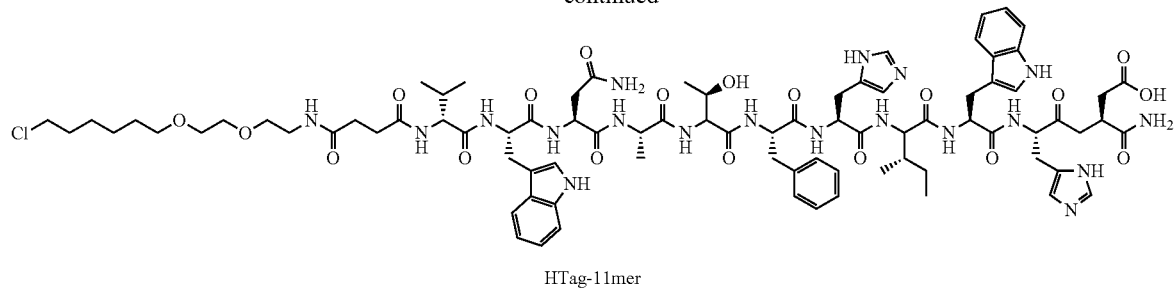

HTag-11mer

As shown in FIG. 23, peptides #2, #7 and #8 displayed significant p62 degradation. These peptides were tested again in a side-by-side comparison with Tat-11mer ("L17") and DD5-o, as shown in FIG. 24. Peptide #8 displayed stronger activity in p62 degradation than Tat-11mer, while peptide #7 is comparable to DD5-o.

DISCUSSION

First reported in 2013, the autophagy-inducing peptide Tat-Beclin 1 has become a critical tool for exploring the therapeutic potential of autophagy activation.[10] Here, we describe two new autophagy-inducing peptides based on Beclin 1-derived sequences. The first, Tat-11mer, has up to 4-fold greater potency than the original peptide, and the second, DD5-o, has nearly equal potency but does not require a large polycationic sequence for cell penetration. Extensive SAR revealed conserved residues among these Beclin 1-derived sequences, suggesting that they operate via the same mechanism. Notably, the conserved residue Trp2 in Tat-11mer is replaced by a cross-linked D-Cys in DD5-o, suggesting that the hydrophobic staple may functionally replace this part of the conserved Beclin 1-derived sequence. Going forward, these two compounds serve different applications. Tat-11mer is the more potent in vitro tool, while DD5-o is more promising for the development of peptide and small-molecule therapeutics.

DD5-o was developed using a novel stapling strategy that scans different structures by varying several aspects of staple position, length, and stereochemistry. Similar chemistry has been applied to phage display libraries and to the design of protein-protein interaction inhibitors, and can incorporate further diversity using alternative linkers or artificial thiol-containing amino acids.[52, 56, 72, 73] Here, we used this approach to convert a 10-mer peptide into a cell-penetrant stapled peptide with activity in vitro and in vivo. Previous work had shown that, in the context of a sequence with high helical propensity, bis-alkylation of L-cysteines at (i, i+4) positions using the meta-xylene linker will stabilize α-helical structure.[74] This matches the staple in DD6-m (FIG. 2b), and indicates that DD6-m is likely also helical in structure. The staple within DD5-o is an (i, i+3) staple that links two D-cysteines with an ortho-xylene group (FIG. 2b), which is a new staple geometry that was not suggested by prior helix-stapling chemistries and configurations.[53, 75-77] Another relevant feature of DD5-o is an extended hydrophobic surface of over 750 Å$^2$ which includes the aromatic staple and the required hot spot residues. This hydrophobic surface wraps around more than half of the helix (FIG. 5c). Having an extended hydrophobic surface was recently found to be critical for cell penetration of hydrocarbon-stapled helices. In fact, DD5-o matches all the biophysical criteria recently described for cell-penetrant stapled helices.[46, 78]

To directly measure cell penetration of DD5-o, we developed a novel, quantitative assay that can determine cytosolic localization using the small Haloligand as a chemical tag. The most common method currently used to judge cell penetration is to monitor the uptake of dye-labeled molecules by microscopy or flow cytometry. This method has difficulty distinguishing material that is trapped in endosomes from material in the cytosol, and it is prone to additional artifacts including leakage of peptide after fixation[79, 80] and light-induced redistribution from endosomes to the cytoplasm.[81] Several groups have developed alternative assays, including dye-mediated assays that produce signals based on changing chemical environment,[82, 83] transcriptional readouts using dexamethasone-tagged peptides,[84] and fluorescence correlation spectroscopy (FCS) for localizing signals in femtoliter volumes within the cell.[85] The Chloroalkane Penetration Assay does not require large, hydrophobic dyes, just a small chloroalkane tag. Because the HeLa cells stably express Haloenzyme fused to a cytosolically-oriented protein domain, any signal dependent on the Haloenzyme reports exclusively on cytoplasmic access of the Haloligand-bearing molecule. When the Haloligand-bearing molecule of interest enters the cell, it covalently reacts with cytoplasmic Haloenzyme and blocks subsequent reaction with the Haloligand-bearing dye in the next step. Control experiments revealed that up to 90% of the overall signal could be suppressed by pre-incubation with a cell-penetrant, Haloligand-conjugated small molecule. The remaining 10% is likely due to Haloenzyme expressed during the subsequent dye incubation and wash steps. The signal was measured using a benchtop flow cytometer. Other readouts are feasible, but flow cytometry provided high-quality, quantitative data in an inexpensive and high-throughput format.

CAPA allowed direct assessment of the dose-dependence of cell penetration for DD5-o. Importantly, this dose dependence closely matches the dose-dependence of autophagy induction. These data imply that potency is currently limited by cell penetration, and that improving cell penetration will improve overall activity. The ability to quantitate cell penetration in a high-throughput manner will greatly accelerate development of these and other potential peptide therapeutics. In fact, the CAPA method can be directly applied to any chemically tractable molecule, including small molecules, peptides, proteins, nucleic acids, antibodies, viral particles, and nanoparticles. Because the Haloenzyme is genetically introduced, it can be directed to any cellular compartment, enabling specific relative quantitation of access to any compartment or organelle. We also anticipate that this method will be directly applicable to whole-organism pharmacokinetics, enabling direct assessment of molecule distribution and subcellular compartmentalization throughout an entire organism.

Finally, the cumulative SAR of all the Beclin 1-derived peptides, the structure of DD5-o, and the activity of retro inverso variants of Tat-Beclin 1 and Tat-11mer provide multiple independent lines of evidence that Beclin 1-derived peptides are most active in helical conformations. This finding contrasts with the published structure of the Beclin 1 ECD and current models of Beclin 1 complexes. The importance of helical structure for Beclin 1-derived peptides raises new questions about the structure and function of the BARA domain of Beclin 1. Further studies on Beclin 1 will be necessary to determine whether this domain assumes a helical structure in its relevant multiprotein complexes, or whether it converts to a helical structure when binding autophagy-regulating Beclin 1 modulators. We expect these and other Beclin 1-derived peptides will continue to reveal molecular details of autophagy induction and regulation, and will continue to serve as potent tools and potential lead compounds for examining the effects of autophagy induction on human disease.

REFERENCES

1. Yoshimori, T. Autophagy: A regulated bulk degradation process inside cells. *Biochem. Biophys. Res. Commun.* 313, 453-458 (2004).
2. Reggiori, F., Komatsu, M., Finley, K. & Simonsen, A. Selective types of autophagy. *Init. J. Cell Biol.* (2012). doi:10.1155/2012/219625
3. Levine, B. & Klionsky, D. J. Development by self-digestion: molecular mechanisms and biological functions of autophagy. *Dev. Cell* 6, 463-477 (2004).
4. Yorimitsu, T. & Klionsky, D. J. Autophagy: molecular machinery for self-eating. *Cell Death Differ* 12, 1542-1552 (2005).
5. Levine, B. & Kroemer, G. Autophagy in the pathogenesis of disease. *Cell* 132, 27-42 (2008).
6. Galluzzi, L., Pietrocola, F., Levine, B. & Kroemer, G. Metabolic control of autophagy. *Cell* 159, 1263-1276 (2014).
7. Kihara, a, Kabeya, Y., Ohsumi, Y. & Yoshimori, T. Beclin-phosphatidylinositol 3-kinase complex functions at the trans-Golgi network. *EMBO Rep* 2, 330-335. (2001).
8. Levine, B., Liu, R., Dong, X. & Zhong, Q. Beclin orthologs: Integrative hubs of cell signaling, membrane trafficking, and physiology. *Trends Cell Biol.* 25, 533-544 (2015).
9. Kyei, G. B. et al. Autophagy pathway intersects with HIV-1 biosynthesis and regulates viral yields in macrophages. *J. Cell Biol.* 186, 255-68 (2009).
10. Shoji-Kawata, S. et al. Identification of a candidate therapeutic autophagy-inducing peptide. *Nature* 494, 201-6 (2013).
11. Liang, X. H. et al. Protection against fatal Sindbis Virus encephalitis by beclin, a novel Bcl-2-interacting protein. *J. Virol.* 72, 8586-8596 (1998).
12. Menzies, F. M., Fleming, A. & Rubinsztein, D. C. Compromised autophagy and neurodegenerative diseases. *Nat. Rev. Neurosci.* 16, 345-357 (2015).
13. Liang, X. H. et al. Induction of autophagy and inhibition of tumorigenesis by beclin 1. *Nature* 402, 672-6 (1999).
14. Yue, Z., Jin, S., Yang, C., Levine, A. J. & Heintz, N. Beclin 1, an autophagy gene essential for early embryonic development, is a haploinsufficient tumor suppressor. *Proc. Natl. Acad. Sci. U.S.A* 100, 15077-82 (2003).
15. Tang, H. et al. Decreased BECN1 mRNA Expression in Human Breast Cancer is Associated With Estrogen Receptor-Negative Subtypes and Poor Prognosis. *EBioMedicine* 2, 255-263 (2015).
16. Qu, X. et al. Promotion of tumorigenesis by heterozygous disruption of the beclin 1 autophagy gene. *J. Clin. Invest.* 112, 1809-1820 (2003).
17. Jiang, P. & Mizushima, N. Autophagy and human diseases. *Cell Res.* 24, 69-79 (2014).
18. Choi, A. M. K., Ryter, S. W. & Levine, B. Autophagy in Human Health and Disease. *The New England journal of medicine* 651-662 (2013). Available at: http://www.nejm.org/doi/full/10.1056/NEJMra1205406. (Accessed: 11 Jan. 2016)
19. Levine, B., Packer, M. & Codogno, P. Development of autophagy inducers in clinical medicine. *J. Clin. Invest.* 125, 14-24 (2015).
20. Mizushima, N. & Komatsu, M. Autophagy: Renovation of cells and tissues. *Cell* 147, 728-741 (2011).
21. Kim, K. H. & Lee, M.-S. Autophagy—a key player in cellular and body metabolism. *Nat. Rev. Endocrinol.* 10, 322-337 (2014).
22. Levine, B., Mizushima, N. & Virgin, H. W. Autophagy in immunity and inflammation. *Nature* 469, 323-35 (2011).
23. Rubinsztein, D. C., Marino, G. & Kroemer, G. Autophagy and aging. *Cell* 146, 682-695 (2011).
24. Mizushima, N., Levine, B., Cuervo, A. M. & Klionsky, D. J. Autophagy fights disease through cellular self-digestion. *Nature* 451, 1069-75 (2008).
25. Rubinsztein, D. C., Codogno, P. & Levine, B. Autophagy modulation as a potential therapeutic target for diverse diseases. *Nat. Rev. Drug Discov.* 11, 709-30 (2012).
26. Cheng, Y., Ren, X., Hait, W. N. & Yang, J. Therapeutic targeting of autophagy in disease: biology and pharmacology. *Pharmacol. Rev.* 65, 1162-1197 (2013).
27. Muciño, G., Castro-Obregón, S., Hernandez-Pando, R. & Del Rio, G. Autophagy as a target for therapeutic uses of multifunctional peptides. *IUBMB Life* n/a-n/a (2016). doi:10.1002/iub.1483
28. Zhong, Z., Sanchez-Lopez, E. & Karin, M. Autophagy, Inflammation, and Immunity: A Troika Governing Cancer and Its Treatment. *Cell* 166, 288-298 (2016).
29. Miao, Y., Li, G., Zhang, X., Xu, H. & Abraham, S. N. A TRP channel senses lysosome neutralization by pathogens to trigger their expulsion. *Cell* 161, 1306-1319 (2015).
30. Kobayashi, S. et al. Autophagy inhibits viral genome replication and gene expression stages in West Nile virus infection. *Virus Res.* 191, 83-91 (2014).
31. Hakata, Y. et al. A novel leucine zipper motif-based hybrid peptide delivers a functional peptide cargo inside cells. *Chem. Commun.* 51, 413-416 (2015).
32. Pietrocola, F. et al. Caloric restriction mimetics enhance anticancer immunosurveillance. *Cancer Cell* 30, 147-160 (2016).
33. Livingston, M. J. et al. Persistent activation of autophagy in kidney tubular cells promotes renal interstitial fibrosis during unilateral ureteral obstruction. *Autophagy* 8627, 1-23 (2016).
34. Liu, Y. et al. Autosis is a $Na^+,K^+$-ATPase-regulated form of cell death triggered by autophagy-inducing peptides, starvation, and hypoxia-ischemia. *Proc. Natl. Acad. Sci. U. S. A.* 110, 20364-71 (2013).

35. Wang, S., Livingston, M. J., Su, Y. & Dong, Z. Reciprocal regulation of cilia and autophagy via the MTOR and proteasome pathways. *Autophagy* 11, 607-616 (2015).
36. Sosulski, M. L. et al. Deregulation of selective autophagy during aging and pulmonary fibrosis: the role of TGFβ1. *Aging Cell* 14, 774-783 (2015).
37. Franco, L. H. et al. The ubiquiutin-ligase Smurf1 functions in selective autophagy of M. tuberculsosis and anti-tuberculous host defense. *Cell Host Microbe* (2016).
38. Goginashvili, A. et al. Insulin granules. Insulin secretory granules control autophagy in pancreatic β cells. *Science (80-.).* 347, 878-82 (2015).
39. Shirakabe, A. et al. Drp1-dependent mitochondrial autophagy plays a protective role against pressure overload-induced mitochondrial dysfunction and heart failure. *Circulation* 133, 1249-1263 (2016).
40. Cinque, L. et al. FGF signalling regulates bone growth through autophagy. *Nature* 528, 272-275 (2015).
41. Cardozo, A. K. el al. Cell-permeable peptides induce dose- and length-dependent cytotoxic effects. *Biochim. Biophys. Acta-Biomembr.* 1768, 2222-2234 (2007).
42. Kritzer, J. a. Stapled peptides: Magic bullets in nature's arsenal. *Nat. Chem. Biol.* 6, 566-567 (2010).
43. Hill, T. A., Shepherd, N. E., Diness, F. & Fairlie, D. P. Constraining Cyclic Peptides To Mimic Protein Structure Motifs. *Angew. Chemie Int. Ed.* 53, 13020-13041 (2014).
44. Mizushima, N., Yoshimori, T. & Levine, B. Methods in mammalian autophagy research. *Cell* 140, 313-26 (2010).
45. Quartararo, J. S. et al. A bicyclic peptide scaffold promotes phosphotyrosine mimicry and cellular uptake. *Bioorg. Med. Chem.* 22, 6387-91 (2014).
46. Chu, Q. et al. Towards understanding cell penetration by stapled peptides. *Medchemcomm* 6, 111-119 (2014).
47. Walensky, L. D. & Bird, G. H. Hydrocarbon-stapled peptides: principles, practice, and progress. *J. Med Chem.* 57, 6275-6288 (2014).
48. Milletti, F. Cell-penetrating peptides: Classes, origin, and current landscape. *Drug Discov. Today* 17, 850-860 (2012).
49. Lau, Y. H. et al. Functionalised staple linkages for modulating the cellular activity of stapled peptides. *Chem. Sci.* 5, 1804 (2014).
50. Gavenonis, J., Jonas, N. E. & Kritzer, J. A. Potential C-terminal-domain inhibitors of heat shock protein 90 derived from a C-terminal peptide helix. *Bioorganic Med Chem.* 22, 3989-3993 (2014).
51. Timmerman, P., Beld, J., Puijk, W. C. & Meloen, R. H. Rapid and quantitative cyclization of multiple peptide loops onto synthetic scaffolds for structural mimicry of protein surfaces. *Chembiochem* 6, 821-4 (2005).
52. Peraro, L., Siegert, T. R. & Kritzer, J. A. Conformational restriction of peptides using dithiol bis-alkylation. *Methods Enzymol.* 580, 303-332 (2016).
53. Jo, H. et al. Development of α-helical calpain probes by mimicking a natural protein-protein interaction. *J. Am. Chem. Soc.* 134, 17704-17713 (2012).
54. Todorova-Balvay, D., Stoilova, I., Gargova, S. & Vijay-alakshmi, M. a. An efficient two step purification and molecular characterization of beta-galactosidases from *Aspergillus oryzae*. *J. Mol. Recognit.* 19, 299-304 (2007).
55. Smeenk, L. E. J., Dailly, N., Hiemstra, H., van Maarseveen, J. H. & Timmerman, P. Synthesis of water-soluble scaffolds for peptide cyclization, labeling, and ligation. *Org. Lett.* 14, 1194-7 (2012).
56. Siegert, T. R., Bird, M. J., Makwana, K. M. & Kritzer, J. A. Analysis of loops that mediate protein-protein interactions and translation into sub-micromolar inhibitors. *J Am. Chem. Soc.* (2016). doi:10.1021/jacs.6b05656
57. Yamamoto, A. et al. Bafilomycin A1 prevents maturation of autophagic vacuoles by inhibiting fusion between autophagosomes and lysosomes in rat hepatoma cell line, H-4-II-E cells. *Cell Struct. Funct.* 23, 33-42 (1998).
58. He, C. & Klionsky, D. J. Regulation mechanisms and signaling pathways of autophagy. *Annu. Rev. Genet.* 43, 67-93 (2009).
59. Mizushima, N., Yamamoto, A., Matsui, M., Yoshimori, T. & Ohsumi, Y. In vivo analysis of autophagy in response to nutrient starvation using transgenic mice expressing a fluorescent autophagosome marker. *Mol. Biol. Cell* 15, 1101-1111 (2004).
60. Yamamoto, A., Cremona, M. L. & Rothman, J. E. Autophagy-mediated clearance of huntingtin aggregates triggered by the insulin-signaling pathway. *J. Cell Biol.* 172, 719-731 (2006).
61. Harris, H. & Rubinsztein, D. C. Control of autophagy as a therapy for neurodegenerative disease. *Nat. Rev. Neurol.* 8, 108-117 (2011).
62. Huang, W. et al. Crystal structure and biochemical analyses reveal Beclin 1 as a novel membrane binding protein. *Cell Res.* 22, 473-89 (2012).
63. Baskaran, S. et al. Architecture and dynamics of the autophagic phosphatidylinositol 3-kinase complex. *Elife* 3, 1-19 (2014).
64. Rostislavleva, K. et al. Structure and flexibility of the endosomal Vps34 complex reveals the basis of its function on membranes. *Science (80-.).* 350, aac7365-aac7365 (2015).
65. Madani, F., Lindberg, S., Langel, U., Futaki, S. & Gräslund, A. Mechanisms of cellular uptake of cell-penetrating peptides. J. Biophys. 2011, 414729 (2011).
66. Erazo-Oliveras, A., Muthukrishnan, N., Baker, R., Wang, T. Y. & Pellois, J. P. Improving the endosomal escape of cell-penetrating peptides and their cargos: Strategies and challenges. *Pharmaceuticals* 5, 1177-1209 (2012).
67. Bechara, C. & Sagan, S. Cell-penetrating peptides: 20 years later, where do we stand? *FEBS Lett.* 587, 1693-702 (2013).
68. Lang, C., Schulze, J., Mendel, R. R. & Hänsch, R. HaloTag™: A new versatile reporter gene system in plant cells. *J. Exp. Bot.* 57, 2985-2992 (2006).
69. Los, G. V. et al. HaloTag: A novel protein labeling technology for cell imaging and protein analysis. *ACS Chem. Biol.* 3, 373-382 (2008).
70. Friedman Ohana, R. et al. Deciphering the Cellular Targets of Bioactive Compounds Using a Chloroalkane Capture Tag. *ACS Chem. Biol.* 10, 2316-2324 (2015).
71. Ballister, E. R., Aonbangkhen, C., Mayo, A. M., Lampson, M. A. & Chenoweth, D. M. Localized light-induced protein dimerization in living cells using a photocaged dimerizer. *Nat. Common.* 5, 1-9 (2014).
72. Chen, S. et al. Dithiol amino acids can structurally shape and enhance the ligand-binding properties of polypeptides. *Nat. Chem.* 6, 1009-1016 (2014).
73. Wang, Y. & Chou, D. H.-C. A Thiol-Ene Coupling Approach to Native Peptide Stapling and Macrocyclization. *Angew. Chemie* Int. Ed. 1, n/a-n/a (2015).
74. Jo, H. et al. Development of α-helical calpain probes by mimicking a natural protein-protein interaction. *J. Am. Chem. Soc.* 134, 17704-13 (2012).
75. Muppidi, A. et al. Design of antiviral stapled peptides containing a biphenyl cross-linker. *Bioorg. Med. Chem. Lett.* 24, 1748-51 (2014).

76. Bird, G. H., Gavathiotis, E., Labelle, J. L., Katz, S. G. & Walensky, L. D. Distinct BimBH3 (BimSAHB) Stapled Peptides for Structural and Cellular Studies. *ACS Chem. Biol.* 3, (2014).
77. Walensky, L. D. et al. Activation of apoptosis in vivo by a hydrocarbon-stapled BH3 helix. *Science* 305, 1466-70 (2004).
78. Bird, G. H. et al. Biophysical determinants for cellular uptake of hydrocarbon-stapled peptide helices. *Nat. Chem. Biol.* 1-9 (2016). doi:10.1038/nchembio.2153
79. Richard, J. P. et al. Cell-penetrating peptides. A reevaluation of the mechanism of cellular uptake. *J. Biol. Chem.* 278, 585-590 (2003).
80. Belitsky, J. M., Leslie, S. J., Arora, P. S., Beerman, T. A. & Dervan, P. B. Cellular uptake of N-methylpyrrole/N-methylimidazole polyamide-dye conjugates. *Bioorganic Med. Chem.* 10, 3313-3318 (2002).
81. Maiolo, J. R., Ottinger, E. a & Ferrer, M. Specific redistribution of cell-penetrating peptides from endosomes to the cytoplasm and nucleus upon laser illumination. *J. Am. Chem. Soc.* 126, 15376-15377 (2004).
82. Mäger, I., Eiriksodottir, E., Langel, K., E L Andaloussi, S. & Langel, U. Assessing the uptake kinetics and internalization mechanisms of cell-penetrating peptides using a quenched fluorescence assay. *Biochim. Biophys. Acta—Biomembr.* 1798, 338-343 (2010).
83. Qian, Z., Dougherty, P. G. & Pei, D. Monitoring the cytosolic entry of cell-penetrating peptides using a pH-sensitive fluorophore. *Chem. Common.* 51, 2162-2165 (2015).
84. Yu, P., Liu, B. & Kodadek, T. A high-throughput assay for assessing the cell permeability of combinatorial libraries. *Nat. Biotechnol.* 23, 746-751 (2005).
85. Larochelle, J. R., Cobb, G. B., Steinauer, A., Rhoades, E. & Schepartz, A. Fluorescence correlation spectroscopy reveals highly efficient cytosolic delivery of certain penta-arg proteins and stapled peptides. *J. Am. Chem. Soc.* 137, 2536-2541 (2015).
86. Pattingre, S. et al. Bcl-2 antiapoptotic proteins inhibit Beclin 1-dependent autophagy. *Cell* 122, 927-39 (2005).

INCORPORATION BY REFERENCE

All publications, patents and patent applications cited herein are incorporated by reference herein in their entirety for all purposes to the same extent as if each individual publication or patent application were specifically indicated to be so incorporated by reference.

What is claimed is:
1. A compound selected from:
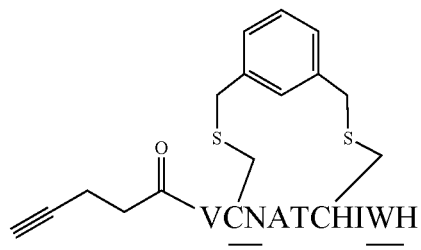
(DD6-m) (SEQ ID NO: 1)
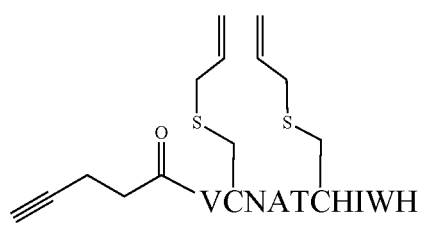
(DD6-allyl) (SEQ ID NO: 1)
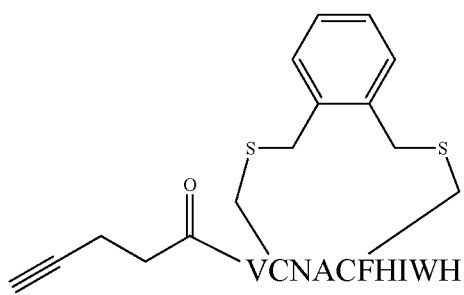
(DD5-o) (SEQ ID NO: 6)
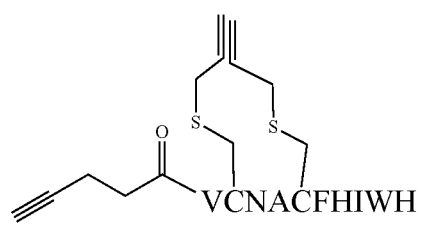
(DD5-allyl) (SEQ ID NO: 6)
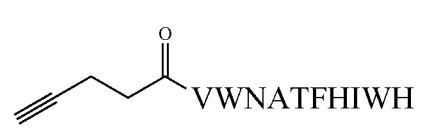
(pa-10mer) (SEQ ID NO: 7)
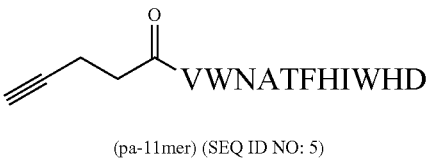
(pa-11mer) (SEQ ID NO: 5)
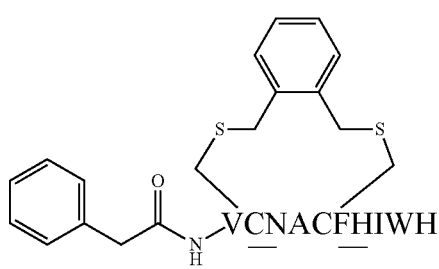
(phenyl-DD5-o) (SEQ ID NO: 6)
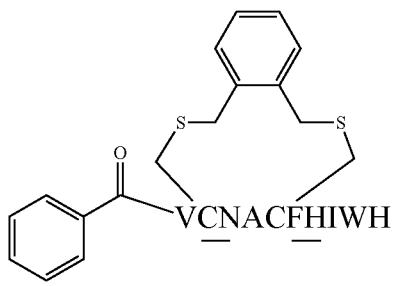
(benzo-DD5-o) (SEQ ID NO: 6)
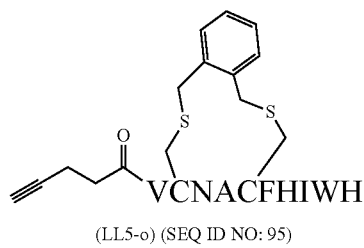
(LL5-o) (SEQ ID NO: 95)
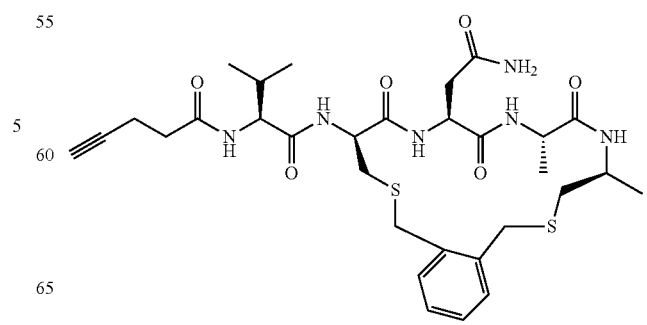

-continued

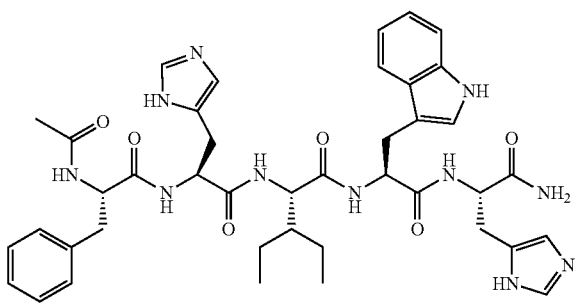

-continued

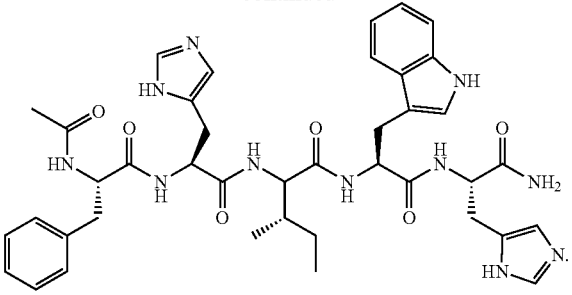

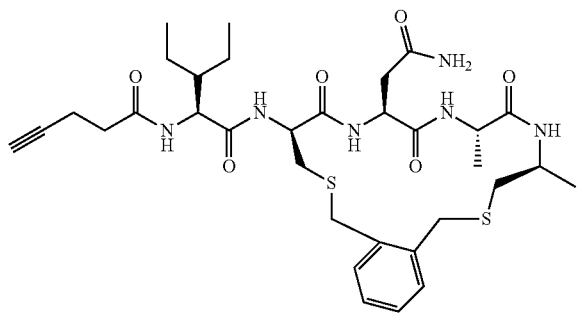

2. A method of inducing autophagy in a cell, the method comprising contacting the cell with an effective amount of the compound of claim 1.

3. A method of treating a disease or condition associated with impaired autophagy in a subject in need thereof, the method comprising: administering to the subject an effective amount of the compound of claim 1 to treat the disease or condition associated with impaired autophagy.

4. A pharmaceutical composition comprising the compound of claim 1.

5. The method of claim 3, wherein the disease or condition is selected from the group consisting of a neurodegenerative disorder, cancer, muscular disease, inflammatory bowel disease, autoimmune and/or inflammatory disorder, infectious disease, metabolic disorder, innate immune disorder, adaptive immune disorder, aging, hepatic insulin resistance, diabetes, lysosomal storage disorder, muscular dystrophy and cystic fibrosis.

* * * * *

SEQUENCE LISTING

```
<160> NUMBER OF SEQ ID NOS: 105

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (6)..(6)
<223> OTHER INFORMATION: D-Cys

<400> SEQUENCE: 1

Val Cys Asn Ala Thr Cys His Ile Trp His
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Cys

<400> SEQUENCE: 2

Val Cys Asn Ala Thr Cys His Ile Trp His
1               5                   10

<210> SEQ ID NO 3
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (6)..(6)
<223> OTHER INFORMATION: D-Cys

<400> SEQUENCE: 3

Val Cys Asn Ala Thr Cys His Ile Trp Arg
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Cys

<400> SEQUENCE: 4

Val Trp Asn Ala Thr Cys His Ile Trp Cys
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Val Trp Asn Ala Thr Phe His Ile Trp His Asp
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (5)..(5)
<223> OTHER INFORMATION: D-Cys

<400> SEQUENCE: 6

Val Cys Asn Ala Cys Phe His Ile Trp His
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 7

Val Trp Asn Ala Thr Phe His Ile Trp His
1               5                   10

<210> SEQ ID NO 8
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Tyr Gly Arg Lys Lys Arg Arg Gln Arg Arg Gly Gly Thr Asn Val
1               5                   10                  15

Phe Asn Ala Thr Phe Glu Ile Trp His Asp Gly Glu Phe Gly Thr
            20                  25                  30

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: D-Cys

<400> SEQUENCE: 9

Val Cys Asn Ala Thr Cys His Ile Trp His
1               5                   10

<210> SEQ ID NO 10
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Gly Arg Lys Lys Arg Arg Gln Arg Arg Gly Gly Val Phe Asn
1               5                   10                  15

Ala Thr Phe Glu Ile Trp His
            20

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: D-Cys

<400> SEQUENCE: 11

Val Trp Asn Ala Thr Cys His Ile Trp Cys
1               5                   10

<210> SEQ ID NO 12
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 12

Val Trp Asn Ala Thr Phe His Ile Trp His Asp
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Val Trp Asn Ala Thr Phe His Ile Trp His
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: L-2-naphthylalanine

<400> SEQUENCE: 14

Phe Ala Arg Arg Arg Arg Glu
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 15

His His His His His His
1               5

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr Gly Arg Lys Lys Arg Arg Gln Arg Arg Arg Gly Gly
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 17

Val Cys Asn Ala Thr Cys His Ile Trp His
1               5                   10

<210> SEQ ID NO 18
<211> LENGTH: 11
<212> TYPE: PRT
<213> ORGANISM: Homo sapiens

<400> SEQUENCE: 18

Val Phe Asn Ala Thr Phe Glu Ile Trp His Asp
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Cys Phe Asn Ala Thr Phe Glu Ile Trp His Asp
1               5                   10

<210> SEQ ID NO 20
<211> LENGTH: 11
<212> TYPE: PRT
<213> ORGANISM: Human immunodeficiency virus

<400> SEQUENCE: 20

Tyr Gly Arg Lys Lys Arg Arg Gln Arg Arg Arg
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Val Trp Asn Ala Thr Phe Glu Ile Trp His Asp
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Val Phe Asp Ala Thr Phe Glu Ile Trp His Asp
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23
```

Val Phe Asn Ser Thr Phe Glu Ile Trp His Asp
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Val Phe Asn Ala Cys Phe Glu Ile Trp His Asp
1               5                   10

<210> SEQ ID NO 25
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Tyr Gly Arg Lys Lys Arg Arg Gln Arg Arg Gly Gly Thr Asn Val
1               5                   10                  15

Phe Asn Ala Thr Phe His Ile Trp His Ser Gly Gln Phe Gly Thr
            20                  25                  30

<210> SEQ ID NO 26
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Tyr Gly Arg Lys Lys Arg Arg Gln Arg Arg Gly Gly Val Gly Asn
1               5                   10                  15

Asp Phe Phe Ile Asn His Glu Thr Thr Gly Phe Ala Thr Glu Trp
            20                  25                  30

<210> SEQ ID NO 27
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(31)
<223> OTHER INFORMATION: D-amino acid

<400> SEQUENCE: 27

Arg Arg Arg Gln Arg Arg Lys Lys Arg Gly Tyr Gly Gly Thr Gly Phe
1               5                   10                  15

Glu Gly Asp His Trp Ile Glu Phe Thr Ala Asn Phe Val Asn Thr
            20                  25                  30

<210> SEQ ID NO 28
<211> LENGTH: 11
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 28

Val Phe Asn Ala Thr Trp Glu Ile Trp His Asp
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Val Phe Asn Ala Thr Phe Asp Ile Trp His Asp
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Val Phe Asn Ala Thr Phe Glu Leu Trp His Asp
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Val Phe Asn Ala Thr Phe Glu Ile Phe His Asp
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Val Phe Asn Ala Thr Phe Glu Ile Trp Tyr Asp
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Val Phe Asn Ala Thr Phe Glu Ile Trp His Glu
1               5                   10

```
<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Val Trp Asn Ala Thr Phe Glu Leu Trp His Asp
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Val Tyr Asn Ala Thr Phe Glu Ile Trp His Asp
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Val Phe Asn Ala Thr Phe Glu Val Trp His Asp
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Val Leu Asn Ala Thr Phe Glu Ile Trp His Asp
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Val Phe Asn Ala Thr Phe Glu Met Trp His Asp
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39
```

Val Phe Asn Ala Thr Phe Glu Phe Trp His Asp
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Val Phe Asn Ala Thr Phe Glu Tyr Trp His Asp
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Val Phe Asn Ala Thr Phe Glu Arg Trp His Asp
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Phe Asn Ala Thr Phe Glu Ile Trp His Asp
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Thr Phe Asn Ala Thr Phe Glu Ile Trp His Asp
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Phe Asn Ala Thr Phe Glu Ile Trp His Asp
1               5                   10

<210> SEQ ID NO 45
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 45

Gly Phe Asn Ala Thr Phe Glu Ile Trp His Asp
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Val Phe Asn Ala Thr Phe Glu Ile Trp His
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Val Trp Asn Ala Thr Phe His Tyr Trp His Asp
1               5                   10

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Phe Asn Ala Thr Phe Glu Ile Trp His
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Phe Asn Ala Thr Phe His Ile Trp His
1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Trp Asn Ala Thr Phe His Ile Trp His
1               5
```

```
<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Trp Asn Ala Thr Phe His Ile Trp His Asp
1               5                   10

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Trp Asn Ala Thr Phe His Ile Trp
1               5

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Val Trp Ala Ala Thr Phe His Ile Trp His Asp
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Val Trp Asn Ala Ala Phe His Ile Trp His Asp
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Val Trp Asn Ala Thr Ala His Ile Trp His Asp
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 56

Val Trp Asn Ala Thr Phe Ala Ile Trp His Asp
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Val Trp Asn Ala Thr Phe His Ala Trp His Asp
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Val Trp Asn Ala Thr Phe His Ile Ala His Asp
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Val Trp Asn Ala Thr Phe His Ile Trp Ala Asp
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Val Ala Asn Ala Thr Phe His Ile Trp His Asp
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asn Ala Thr Phe His Ile Trp
1               5

<210> SEQ ID NO 62
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 62

Trp Asn Ala Thr Phe His Ile
1               5

<210> SEQ ID NO 63
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Tyr Gly Arg Lys Lys Arg Arg Gln Arg Arg Arg Gly Gly Val Trp Asn
1               5                   10                  15

Ala Thr Phe His Ile Trp His Asp
            20

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Val Cys Asn Ala Thr Cys His Ile Trp His
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (6)..(6)
<223> OTHER INFORMATION: D-Cys

<400> SEQUENCE: 65

Val Cys Asn Ala Thr Cys His Ile Arg Ile Trp His
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (6)..(6)
<223> OTHER INFORMATION: D-Cys
```

```
<400> SEQUENCE: 66

Arg Cys Asn Ala Arg Cys Arg Ile Trp Arg
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (6)..(6)
<223> OTHER INFORMATION: D-Cys

<400> SEQUENCE: 67

Val Cys Asn Ala Thr Cys Arg Ile Trp Arg
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: D-Cys

<400> SEQUENCE: 68

Val Cys Asn Ala Cys Phe His Ile Trp His
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: D-Cys
<220> FEATURE:
<221> NAME/KEY: MOD_RES
<222> LOCATION: (10)..(10)
<223> OTHER INFORMATION: D-Cys

<400> SEQUENCE: 69

Val Trp Asn Ala Thr Cys His Ile Trp Cys
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
```

<223> OTHER INFORMATION: D-Cys
<220> FEATURE:
<221> NAME/KEY: MOD_RES
<222> LOCATION: (5)..(5)
<223> OTHER INFORMATION: D-Cys

<400> SEQUENCE: 70

Val Cys Asn Ala Cys Phe His Ile Trp His
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Cys

<400> SEQUENCE: 71

Val Cys Asn Ala Cys Phe His Ile Trp His
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: D-Cys

<400> SEQUENCE: 72

Val Cys Asn Ala Cys Phe His Ile Trp His
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (6)..(6)
<223> OTHER INFORMATION: D-Cys

<400> SEQUENCE: 73

Val Cys Asn Ala Thr Cys His Ile Trp His
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (2)..(2)
<223> OTHER INFORMATION: D-Cys
<220> FEATURE:
<221> NAME/KEY: MOD_RES
<222> LOCATION: (5)..(5)
<223> OTHER INFORMATION: D-Cys

<400> SEQUENCE: 74

Val Cys Asn Ala Cys Phe His Ile Trp His
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (5)..(5)
<223> OTHER INFORMATION: D-Cys

<400> SEQUENCE: 75

Val Cys Asn Ala Cys Phe His Ile Trp His
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (5)..(5)
<223> OTHER INFORMATION: D-Cys

<400> SEQUENCE: 76

Val Cys Asn Ala Cys Phe His Ile Trp Ala
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (5)..(5)
<223> OTHER INFORMATION: D-Cys

<400> SEQUENCE: 77

Val Cys Asn Ala Cys Phe His Ile Ala His
1               5                   10
```

-continued

```
<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (5)..(5)
<223> OTHER INFORMATION: D-Cys

<400> SEQUENCE: 78

Val Cys Asn Ala Cys Phe His Ala Trp His
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (5)..(5)
<223> OTHER INFORMATION: D-Cys

<400> SEQUENCE: 79

Val Cys Asn Ala Cys Phe Ala Ile Trp His
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (5)..(5)
<223> OTHER INFORMATION: D-Cys

<400> SEQUENCE: 80

Val Cys Asn Ala Cys Ala His Ile Trp His
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
```

```
<222> LOCATION: (5)..(5)
<223> OTHER INFORMATION: D-Cys

<400> SEQUENCE: 81

Val Cys Ala Ala Cys Phe His Ile Trp His
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (5)..(5)
<223> OTHER INFORMATION: D-Cys

<400> SEQUENCE: 82

Ala Cys Asn Ala Cys Phe His Ile Trp His
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (5)..(5)
<223> OTHER INFORMATION: D-Cys

<400> SEQUENCE: 83

Val Cys Asn Ala Cys Phe His Ile Trp His
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: D-Cys
<220> FEATURE:
<221> NAME/KEY: MOD_RES
<222> LOCATION: (10)..(10)
<223> OTHER INFORMATION: D-Cys

<400> SEQUENCE: 84

Val Trp Asn Ala Thr Cys His Ile Trp Cys
1               5                   10

<210> SEQ ID NO 85
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: D-Cys

<400> SEQUENCE: 85

Val Trp Asn Ala Thr Cys His Ile Trp Cys
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: D-Cys
<220> FEATURE:
<221> NAME/KEY: MOD_RES
<222> LOCATION: (11)..(11)
<223> OTHER INFORMATION: D-Cys

<400> SEQUENCE: 86

Val Trp Asn Ala Thr Phe Cys Ile Trp His Cys
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: D-Cys

<400> SEQUENCE: 87

Val Cys Asn Ala Thr Cys His Ile Trp His
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (5)..(5)
<223> OTHER INFORMATION: D-Cys

<400> SEQUENCE: 88

Val Cys Asn Ala Cys Phe His Ile Trp His
1               5                   10

<210> SEQ ID NO 89
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (5)..(5)
<223> OTHER INFORMATION: D-Cys

<400> SEQUENCE: 89

Val Cys Asn Ala Cys Phe His Ile Trp His
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (5)..(5)
<223> OTHER INFORMATION: D-Cys

<400> SEQUENCE: 90

Val Cys Asn Ala Cys Phe His Ile Trp His
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (5)..(5)
<223> OTHER INFORMATION: D-Cys

<400> SEQUENCE: 91

Val Cys Asn Ala Cys Phe His Ile Trp His
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (5)..(5)
<223> OTHER INFORMATION: D-Cys
```

```
<400> SEQUENCE: 92

Val Cys Asn Ala Cys Phe His Ile Trp His
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (5)..(5)
<223> OTHER INFORMATION: D-Cys

<400> SEQUENCE: 93

Val Cys Asn Ala Cys Phe His Ile Trp His
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (5)..(5)
<223> OTHER INFORMATION: D-Cys

<400> SEQUENCE: 94

Val Cys Asn Ala Cys Phe His Ile Trp His
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Val Cys Asn Ala Cys Phe His Ile Trp His
1               5                   10

<210> SEQ ID NO 96
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Tyr Gly Arg Lys Lys Arg Arg Gln Arg Arg Gly Gly Val Trp Ala
1               5                   10                  15

Ala Thr Phe His Ile Trp His Asp
            20
```

<210> SEQ ID NO 97
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Tyr Gly Arg Lys Lys Arg Arg Gln Arg Arg Gly Gly Val Trp Asn
1               5                   10                  15

Ala Ala Phe His Ile Trp His Asp
            20

<210> SEQ ID NO 98
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Tyr Gly Arg Lys Lys Arg Arg Gln Arg Arg Gly Gly Val Trp Asn
1               5                   10                  15

Ala Thr Ala His Ile Trp His Asp
            20

<210> SEQ ID NO 99
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Tyr Gly Arg Lys Lys Arg Arg Gln Arg Arg Gly Gly Val Trp Asn
1               5                   10                  15

Ala Thr Phe Ala Ile Trp His Asp
            20

<210> SEQ ID NO 100
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Tyr Gly Arg Lys Lys Arg Arg Gln Arg Arg Gly Gly Val Trp Asn
1               5                   10                  15

Ala Thr Phe His Ala Trp His Asp
            20

<210> SEQ ID NO 101
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

```
Tyr Gly Arg Lys Lys Arg Arg Gln Arg Arg Gly Gly Val Trp Asn
1               5                   10                  15

Ala Thr Phe His Ile Ala His Asp
            20

<210> SEQ ID NO 102
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Tyr Gly Arg Lys Lys Arg Arg Gln Arg Arg Gly Gly Val Trp Asn
1               5                   10                  15

Ala Thr Phe His Ile Trp Ala Asp
            20

<210> SEQ ID NO 103
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Tyr Gly Arg Lys Lys Arg Arg Gln Arg Arg Gly Gly Val Ala Asn
1               5                   10                  15

Ala Thr Phe His Ile Trp His Asp
            20

<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Val Phe Asn Ala Thr Phe His Ile Trp His Ser
1               5                   10

<210> SEQ ID NO 105
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Tyr Gly Arg Lys Lys Arg Arg Gln Arg Arg Gly Gly Val Phe Asn
1               5                   10                  15

Ala Thr Phe Glu Ile Trp His Asp
            20
```